(12) United States Patent
Burns et al.

(10) Patent No.: US 11,864,909 B2
(45) Date of Patent: Jan. 9, 2024

(54) PERFUSION AND OXYGENATION MEASUREMENT

(71) Applicant: BBI Medical Innovations, LLC, Los Angeles, CA (US)

(72) Inventors: Martin F. Burns, Los Angeles, CA (US); Graham O. Ross, Oceanside, CA (US)

(73) Assignee: BBI Medical Innovations, LLC, Los Angeles, CA (US)

( * ) Notice: Subject to any disclaimer, the term of this patent is extended or adjusted under 35 U.S.C. 154(b) by 977 days.

(21) Appl. No.: 16/511,802

(22) Filed: Jul. 15, 2019

(65) Prior Publication Data
US 2020/0015735 A1 Jan. 16, 2020

Related U.S. Application Data

(60) Provisional application No. 62/849,700, filed on May 17, 2019, provisional application No. 62/698,684, filed on Jul. 16, 2018.

(51) Int. Cl.
*A61B 5/00* (2006.01)
*A61B 5/1455* (2006.01)
*A61B 5/026* (2006.01)

(52) U.S. Cl.
CPC ............ *A61B 5/445* (2013.01); *A61B 5/0064* (2013.01); *A61B 5/0075* (2013.01);
(Continued)

(58) Field of Classification Search
CPC ..... A61B 5/445; A61B 5/0064; A61B 5/0075; A61B 5/14552; A61B 5/0261; A61B 5/447; A61B 5/4836; A61B 5/6892; A61G 7/057
See application file for complete search history.

(56) References Cited

U.S. PATENT DOCUMENTS 4,416,285 A 11/1983 Shaw et al.
4,854,699 A 8/1989 Edgar, Jr.
(Continued)

FOREIGN PATENT DOCUMENTS

AT 413327 B 2/2006
CN 1830386 A 9/2006
(Continued)

OTHER PUBLICATIONS

Brem et al. "High Cost of Stage IV Pressure Ulcers," *Am. J. Surg.*, 200(4):473-477 (2010).
(Continued)

*Primary Examiner* — Jason M Sims
*Assistant Examiner* — Abid A Mustansir
(74) *Attorney, Agent, or Firm* — Arnold & Porter Kaye Scholer LLP

(57) ABSTRACT

The present disclosure provides methods and apparatus for evaluating the flow of blood in damaged or healing tissue. The present disclosure also provides methods of identifying a patient at the onset of risk of pressure ulcer or at risk of the onset of pressure ulcer, and treating the patient with anatomy-specific clinical intervention selected based on perfusion or blood oxygenation values, or a combination thereof. The present disclosure also provides methods of stratifying groups of patients based on risk of wound development and methods of reducing incidence of tissue damage in a care facility. The present disclosure also provides methods to analyze trends of perfusion or oxygenation measurements to detect tissue damage before it is visible, and methods to compare bisymmetric perfusion values to identify damaged tissue.

19 Claims, 27 Drawing Sheets

(52) U.S. Cl.
CPC ........ *A61B 5/14552* (2013.01); *A61B 5/0261* (2013.01); *A61B 5/447* (2013.01)

(56) References Cited

U.S. PATENT DOCUMENTS

| | | | |
|---|---|---|---|
| 5,007,423 A | 4/1991 | Branstetter et al. | |
| 5,054,487 A | 10/1991 | Clarke | |
| 5,088,493 A | 2/1992 | Giannini et al. | |
| 5,137,355 A | 8/1992 | Barbour et al. | |
| 5,203,329 A | 4/1993 | Takatani et al. | |
| 5,408,998 A | 4/1995 | Mersch | |
| 5,601,079 A | 2/1997 | Wong et al. | |
| 5,676,143 A | 10/1997 | Simonsen et al. | |
| 5,853,370 A | 12/1998 | Chance et al. | |
| 5,995,882 A | 11/1999 | Patterson et al. | |
| 6,023,541 A | 2/2000 | Merchant et al. | |
| 6,031,603 A | 2/2000 | Fine et al. | |
| 6,075,610 A | 6/2000 | Ueda et al. | |
| 6,223,069 B1 | 4/2001 | Pfeiffer et al. | |
| 6,259,936 B1 | 7/2001 | Boggett et al. | |
| 6,263,227 B1 | 7/2001 | Boggett et al. | |
| 6,272,363 B1 | 8/2001 | Casciani et al. | |
| 6,400,971 B1 | 6/2002 | Finarov et al. | |
| 6,587,701 B1 | 7/2003 | Stranc et al. | |
| 6,606,509 B2 | 8/2003 | Schmitt | |
| 6,615,065 B1 | 9/2003 | Barrett et al. | |
| 6,630,673 B2 | 10/2003 | Khalil et al. | |
| 6,640,130 B1 | 10/2003 | Freeman et al. | |
| 6,662,031 B1 | 12/2003 | Khalil et al. | |
| 6,662,033 B2 | 12/2003 | Casciani et al. | |
| 6,709,402 B2 | 3/2004 | Dekker | |
| 6,718,189 B2 | 4/2004 | Rohrscheib et al. | |
| 6,801,648 B2 | 10/2004 | Cheng | |
| 6,801,799 B2 | 10/2004 | Mendelson | |
| 6,802,812 B1 | 10/2004 | Walker et al. | |
| 6,859,658 B1 | 2/2005 | Krug | |
| 6,875,176 B2 | 4/2005 | Mourad et al. | |
| 6,907,279 B2 | 6/2005 | Sato et al. | |
| 6,987,993 B2 | 1/2006 | Steuer et al. | |
| 7,065,392 B2 | 6/2006 | Kato | |
| 7,130,672 B2 | 10/2006 | Pewzner et al. | |
| 7,184,809 B1 | 2/2007 | Sterling et al. | |
| 7,236,811 B2 | 6/2007 | Schmitt | |
| 7,254,427 B2 | 8/2007 | Cho et al. | |
| 7,400,918 B2 | 7/2008 | Parker et al. | |
| 7,463,916 B2 | 12/2008 | Kawasaki et al. | |
| 7,483,733 B2 | 1/2009 | Shani et al. | |
| 7,509,153 B2 | 3/2009 | Blank et al. | |
| 7,532,919 B2 | 5/2009 | Soyemi et al. | |
| 7,610,082 B2 | 10/2009 | Chance | |
| 7,613,504 B2 | 11/2009 | Rowe | |
| 7,729,747 B2 | 6/2010 | Stranc et al. | |
| 7,751,895 B2 | 7/2010 | Jones et al. | |
| 7,778,693 B2 | 8/2010 | Barbour et al. | |
| 7,787,947 B2 | 8/2010 | Bhunia et al. | |
| 7,796,247 B2 | 9/2010 | Mao et al. | |
| 7,817,256 B2 | 10/2010 | Fujii et al. | |
| 7,860,554 B2 | 12/2010 | Leonardi et al. | |
| 7,915,601 B2 | 3/2011 | Setlak et al. | |
| 7,930,015 B2 | 4/2011 | Mansour et al. | |
| 7,945,312 B2 | 5/2011 | Hular et al. | |
| 7,949,387 B2 | 5/2011 | Khoobehi et al. | |
| 7,983,740 B2 | 7/2011 | Culver et al. | |
| 8,038,626 B2 | 10/2011 | Cinbis et al. | |
| 8,050,744 B2 | 11/2011 | Maki et al. | |
| 8,086,302 B2 | 12/2011 | Kracker | |
| 8,100,834 B2 | 1/2012 | Shuler | |
| 8,199,322 B2 | 6/2012 | Kashyap et al. | |
| 8,285,353 B2 | 10/2012 | Choi et al. | |
| 8,315,681 B2 | 11/2012 | Kanayama et al. | |
| 8,346,327 B2 | 1/2013 | Campbell et al. | |
| 8,346,332 B2 | 1/2013 | Kuhn et al. | |
| 8,406,838 B2 | 3/2013 | Kato | |
| 8,406,865 B2 | 3/2013 | McKenna | |
| 8,417,310 B2 | 4/2013 | Haisley | |
| 8,457,705 B2 | 6/2013 | Shoureshi et al. | |
| 8,463,345 B2 | 6/2013 | Kuhn et al. | |
| 8,478,419 B2 | 7/2013 | Pless et al. | |
| 8,489,164 B2 | 7/2013 | Kuhn | |
| 8,512,254 B2 | 8/2013 | Donofrio | |
| 8,515,537 B2 | 8/2013 | Cinbis et al. | |
| 8,583,565 B2 | 11/2013 | Shoureshi et al. | |
| 8,606,342 B2 | 12/2013 | Diab | |
| 8,611,977 B2 | 12/2013 | Baker, Jr. | |
| 8,622,918 B1 | 1/2014 | Mao et al. | |
| 8,639,309 B2 | 1/2014 | Shuler | |
| 8,644,900 B2 | 2/2014 | Balberg et al. | |
| 8,652,060 B2 | 2/2014 | Al-Ali | |
| 8,768,424 B2 | 7/2014 | Crowe et al. | |
| 8,781,546 B2 | 7/2014 | Wider et al. | |
| 8,788,004 B2 | 7/2014 | Chen et al. | |
| 8,803,070 B2 | 8/2014 | Fujiwara | |
| 8,818,476 B2 | 8/2014 | Besko | |
| 8,838,211 B2 | 9/2014 | Melendez et al. | |
| 8,891,087 B2 | 11/2014 | Zuzak et al. | |
| 9,031,629 B2 | 5/2015 | Park et al. | |
| 9,211,072 B2 | 12/2015 | Kiani | |
| 9,211,091 B2 | 12/2015 | Cinbis et al. | |
| 9,226,661 B2 | 1/2016 | Thompson et al. | |
| 9,236,711 B2 | 1/2016 | Park | |
| 9,265,457 B2 | 2/2016 | Kudavelly et al. | |
| 9,271,658 B2 | 3/2016 | Ferguson, Jr. et al. | |
| 9,364,175 B2 | 6/2016 | Benni | |
| 9,364,176 B2 | 6/2016 | Bernreuter | |
| 9,420,967 B2 | 8/2016 | Zand et al. | |
| 9,480,425 B2 | 11/2016 | Culver et al. | |
| 9,498,157 B2 | 11/2016 | Bechtel et al. | |
| 9,498,158 B2 | 11/2016 | Isaacson | |
| 9,538,949 B2 | 1/2017 | Al-Ali et al. | |
| 9,662,051 B2 | 5/2017 | Masin et al. | |
| 9,668,661 B2 | 6/2017 | Melker et al. | |
| 9,675,250 B2 | 6/2017 | Tverskoy | |
| 9,687,162 B2 | 6/2017 | Vetter et al. | |
| 9,713,447 B2 | 7/2017 | Caduff et al. | |
| 9,763,585 B2 | 9/2017 | Addison et al. | |
| 9,795,310 B2 | 10/2017 | Al-Ali | |
| 9,801,556 B2 | 10/2017 | Kiani | |
| 9,820,691 B2 | 11/2017 | Kiani | |
| 9,854,993 B1 | 1/2018 | Lash et al. | |
| 9,942,110 B2 | 4/2018 | Malnati et al. | |
| 9,968,788 B2 | 5/2018 | Ecker et al. | |
| 9,980,650 B2 | 5/2018 | Bezemer | |
| 10,070,796 B2 | 9/2018 | Ostroverkhov et al. | |
| 10,092,200 B2 | 10/2018 | Al-Ali et al. | |
| 10,101,571 B2 | 10/2018 | Andre et al. | |
| 10,169,862 B2 | 1/2019 | Andre et al. | |
| 10,213,122 B2 | 2/2019 | Lee et al. | |
| 10,548,519 B2 | 2/2020 | Arias et al. | |
| 10,874,348 B1* | 12/2020 | Han | A61B 5/6843 |
| 2001/0051767 A1 | 12/2001 | Williams et al. | |
| 2003/0139667 A1 | 7/2003 | Hewko et al. | |
| 2004/0054290 A1 | 3/2004 | Chance | |
| 2005/0267346 A1 | 12/2005 | Faber et al. | |
| 2006/0149154 A1 | 7/2006 | Stephens et al. | |
| 2007/0043276 A1 | 2/2007 | Mannheimer et al. | |
| 2007/0078316 A1 | 4/2007 | Hoarau et al. | |
| 2007/0239215 A1 | 10/2007 | Bhunia et al. | |
| 2007/0270673 A1 | 11/2007 | Abrams et al. | |
| 2008/0009689 A1 | 1/2008 | Benaron et al. | |
| 2008/0076996 A1* | 3/2008 | Hoarau | A61B 5/7207 |
| | | | 600/323 |
| 2008/0146906 A1 | 6/2008 | Baker et al. | |
| 2008/0188760 A1* | 8/2008 | Al-Ali | A61B 5/02416 |
| | | | 600/507 |
| 2008/0208269 A1* | 8/2008 | Cinbis | A61B 5/363 |
| | | | 607/3 |
| 2008/0214943 A1 | 9/2008 | Kara et al. | |
| 2008/0234560 A1 | 9/2008 | Nomoto et al. | |
| 2009/0069674 A1 | 3/2009 | Masumura et al. | |
| 2009/0163787 A1 | 6/2009 | Mannheimer et al. | |
| 2009/0270702 A1 | 10/2009 | Zeng et al. | |
| 2009/0318908 A1 | 12/2009 | Van Pieterson et al. | |
| 2009/0326346 A1 | 12/2009 | Kracker et al. | |
| 2009/0326350 A1 | 12/2009 | Kracker | |

(56) References Cited

U.S. PATENT DOCUMENTS

| | | |
|---|---|---|
| 2010/0049007 A1 | 2/2010 | Sterling et al. |
| 2010/0076282 A1 | 3/2010 | Sandmore |
| 2010/0100160 A1 | 4/2010 | Edman et al. |
| 2010/0106220 A1 | 4/2010 | Ecker et al. |
| 2010/0210931 A1 | 8/2010 | Cuccia et al. |
| 2010/0241006 A1 | 9/2010 | Choi et al. |
| 2010/0249550 A1 | 9/2010 | Lovejoy |
| 2010/0256461 A1 | 10/2010 | Mohamedali et al. |
| 2011/0060197 A1 | 3/2011 | Zhang et al. |
| 2012/0253153 A1* | 10/2012 | Trumble ............ A61B 5/14551 600/324 |
| 2012/0277559 A1 | 11/2012 | Kohl-Bareis et al. |
| 2013/0018233 A1 | 1/2013 | Cinbis et al. |
| 2013/0169759 A1 | 7/2013 | Godavarty et al. |
| 2013/0184539 A1 | 7/2013 | Buchenrieder et al. |
| 2013/0289372 A1 | 10/2013 | Imran |
| 2013/0345560 A1 | 12/2013 | Ferguson, Jr. et al. |
| 2014/0128695 A1 | 5/2014 | Fang et al. |
| 2014/0180026 A1 | 6/2014 | Melker et al. |
| 2014/0243681 A1 | 8/2014 | Hielscher et al. |
| 2014/0275869 A1 | 9/2014 | Kintz et al. |
| 2014/0316224 A1 | 10/2014 | Sato |
| 2014/0343383 A1 | 11/2014 | Sato |
| 2014/0343384 A1 | 11/2014 | Floyd et al. |
| 2014/0378782 A1 | 12/2014 | Herken et al. |
| 2015/0080742 A1 | 3/2015 | Andre et al. |
| 2015/0099955 A1 | 4/2015 | Al-Ali et al. |
| 2015/0105810 A1 | 4/2015 | Leschinsky et al. |
| 2015/0119665 A1 | 4/2015 | Barbour et al. |
| 2015/0148624 A1 | 5/2015 | Benaron |
| 2015/0164347 A1 | 6/2015 | Pollonini et al. |
| 2015/0174355 A1 | 6/2015 | Willard et al. |
| 2015/0374276 A1 | 12/2015 | Farkas et al. |
| 2015/0374309 A1 | 12/2015 | Farkas et al. |
| 2016/0058312 A1 | 3/2016 | Han et al. |
| 2016/0081603 A1 | 3/2016 | Liu et al. |
| 2016/0180139 A1 | 6/2016 | Hung et al. |
| 2016/0242657 A1 | 8/2016 | Wang et al. |
| 2016/0249836 A1 | 9/2016 | Gulati et al. |
| 2016/0262723 A1 | 9/2016 | Zhu |
| 2016/0287181 A1 | 10/2016 | Han et al. |
| 2016/0310023 A1 | 10/2016 | Chachisvilis et al. |
| 2016/0360971 A1 | 12/2016 | Gross et al. |
| 2016/0361004 A1 | 12/2016 | Lange et al. |
| 2017/0014044 A1 | 1/2017 | Tonar et al. |
| 2017/0055896 A1 | 3/2017 | Al-Ali et al. |
| 2017/0202505 A1 | 7/2017 | Kirenko et al. |
| 2017/0274205 A1 | 9/2017 | Chen et al. |
| 2017/0303834 A1 | 10/2017 | Bechtel et al. |
| 2018/0020932 A1 | 1/2018 | Chen et al. |
| 2018/0092553 A1 | 4/2018 | Baumbach |
| 2018/0235484 A1 | 8/2018 | Mozdzierz |
| 2018/0317857 A1 | 11/2018 | Segman |
| 2019/0008387 A1 | 1/2019 | Godavarty |
| 2019/0059787 A1 | 2/2019 | Freeman et al. |
| 2019/0069835 A1 | 3/2019 | Xu et al. |
| 2020/0281529 A1* | 9/2020 | Grubb ................ A61F 13/0206 |

FOREIGN PATENT DOCUMENTS

| | | |
|---|---|---|
| CN | 101933071 A | 12/2010 |
| CN | 102920464 A | 2/2013 |
| CN | 103735273 A | 4/2014 |
| CN | 203524682 U | 4/2014 |
| CN | 103519826 B | 5/2015 |
| CN | 104856653 A | 8/2015 |
| CN | 103735274 B | 10/2015 |
| CN | 103610467 B | 8/2016 |
| DE | 102008002741 A1 | 12/2009 |
| EP | 2609854 A1 | 12/2012 |
| EP | 3434182 A1 | 1/2019 |
| JP | 7-506987 | 8/1995 |
| JP | 2000501974 A | 2/2000 |
| JP | 2003111750 | 4/2003 |
| JP | 2004337605 | 12/2004 |
| JP | 2006230657 | 9/2006 |
| JP | 2008237775 | 10/2008 |
| JP | 2010532699 | 10/2010 |
| JP | 2011206591 A | 10/2011 |
| KR | 10-2011-0004065 A | 4/2011 |
| WO | 1999/040842 A1 | 8/1999 |
| WO | 2002/017778 A1 | 3/2002 |
| WO | 2002/074162 A1 | 9/2002 |
| WO | 2002/075289 A2 | 9/2002 |
| WO | 2004/052195 A1 | 6/2004 |
| WO | 2007/067927 A2 | 6/2007 |
| WO | 2008/117338 A1 | 10/2008 |
| WO | 2009/117603 A2 | 9/2009 |
| WO | 2009/124076 A1 | 10/2009 |
| WO | 2010/044879 A2 | 4/2010 |
| WO | 2012/100090 A2 | 7/2012 |
| WO | 2014/073331 A1 | 5/2014 |
| WO | 2015/193306 A1 | 12/2015 |
| WO | 2017/189376 A1 | 11/2017 |
| WO | 2018/162728 A2 | 9/2018 |
| WO | 2018/175787 A1 | 9/2018 |

OTHER PUBLICATIONS

Diaz et al., "Pressure Injury Prediction Using Diffusely Scattered Light," *J. Biomed. Opt.*, 22(2):025003-1-025003-10 (2017).

Garcia-Fernandez et al., "Predictive Capacity of Risk Assessment Scales and Clinical Judgment for Pressure Ulcers: A Meta-Analysis," *Journal of Wound, Ostomy and Continence Nursing*, 41:24-34 (2014).

The National Institute for Health and Care Excellence (NICE), "Pressure Ulcers: Prevention and Management," Clinical Guideline 179 (available at www.nice.org.uk/guidance/cg179) (Apr. 23, 2014).

Pancorbo-Hidalgo et al., "Risk Assessment Scales for Pressure Ulcer Prevention: A Systematic Review," *Journal of Advanced Nursing*, 54:94-110 (2006).

Weingarten et al., "Diffuse Near-Infrared Spectroscopy Prediction of Healing in Diabetic Foot Ulcers: A Human Study and Cost Analysis," *Wound Rep. Reg.*, pp. 1-7 (2012).

* cited by examiner

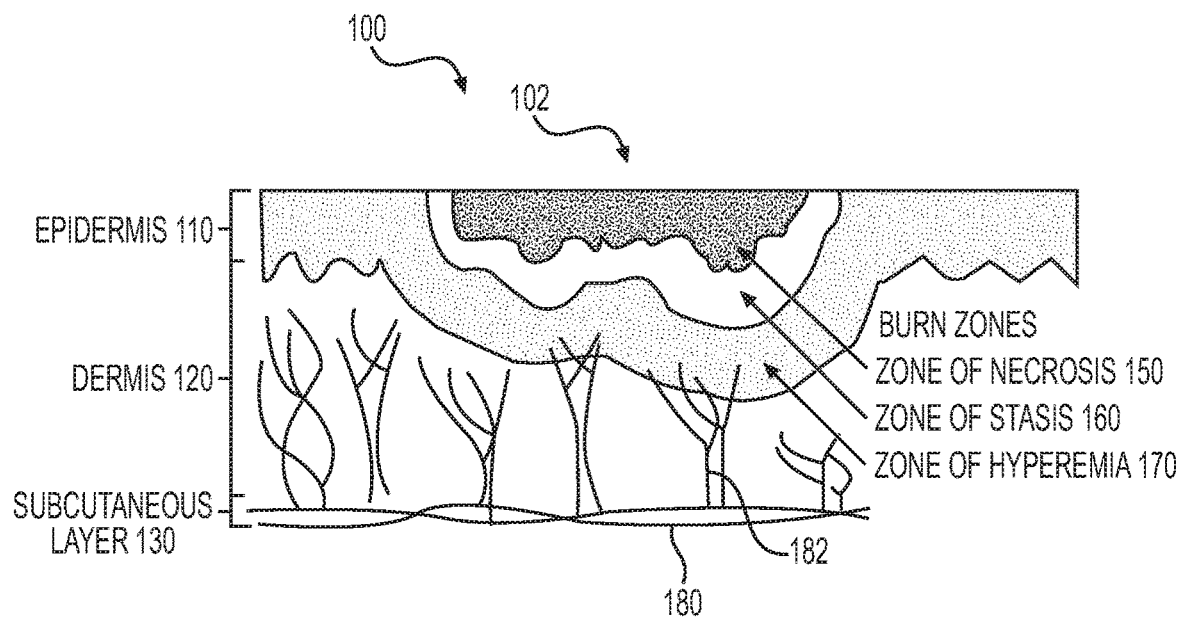
FIG. 1
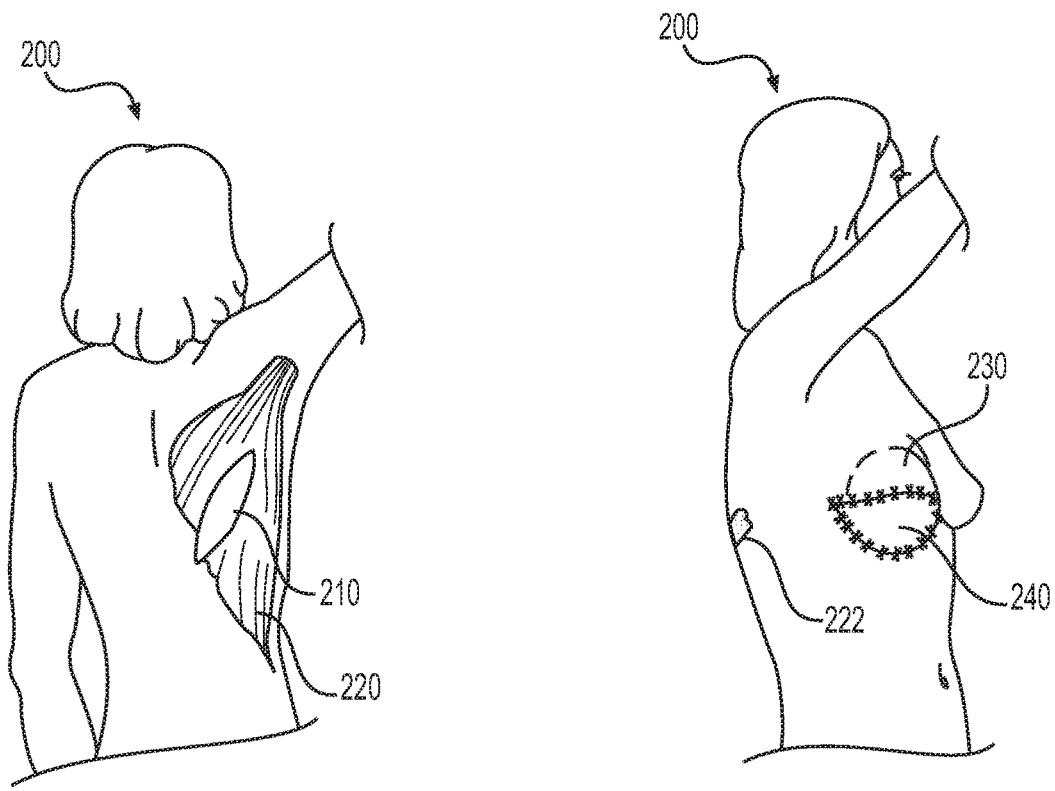
FIG. 2A  FIG. 2B

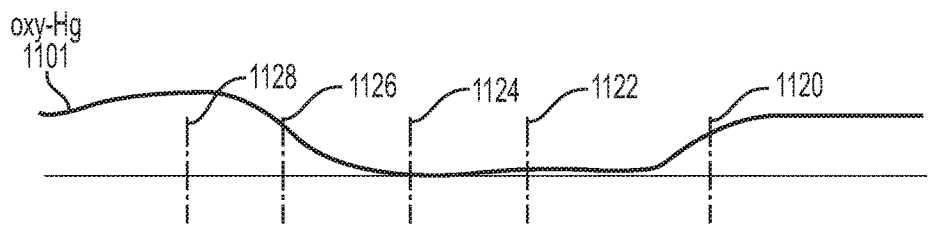
FIG. 11A
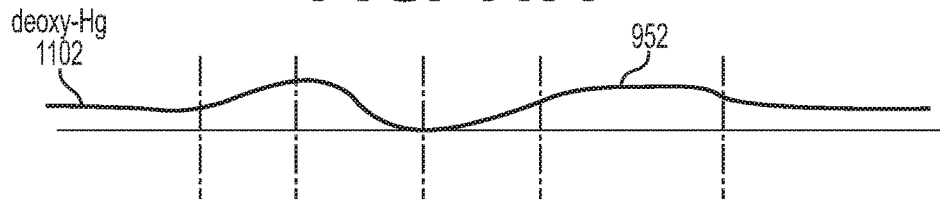
FIG. 11B
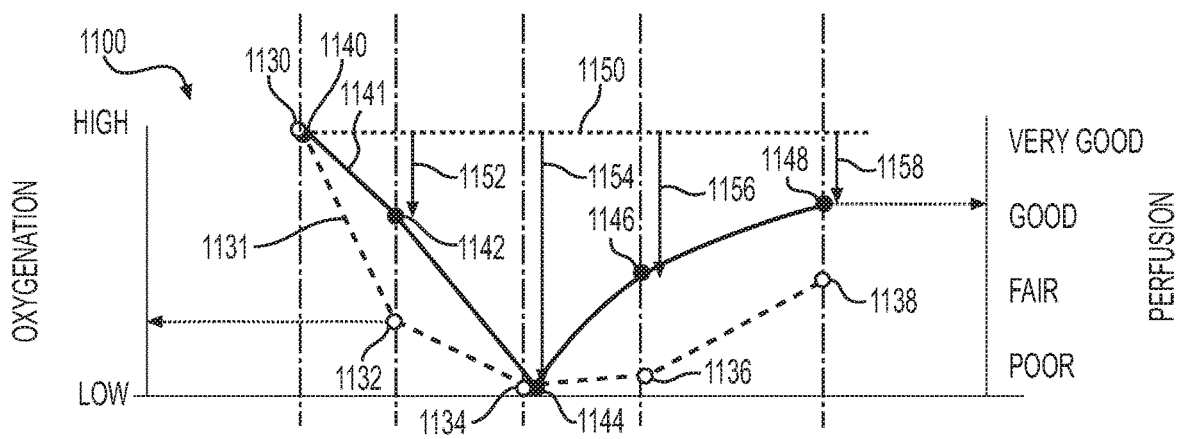
FIG. 11C
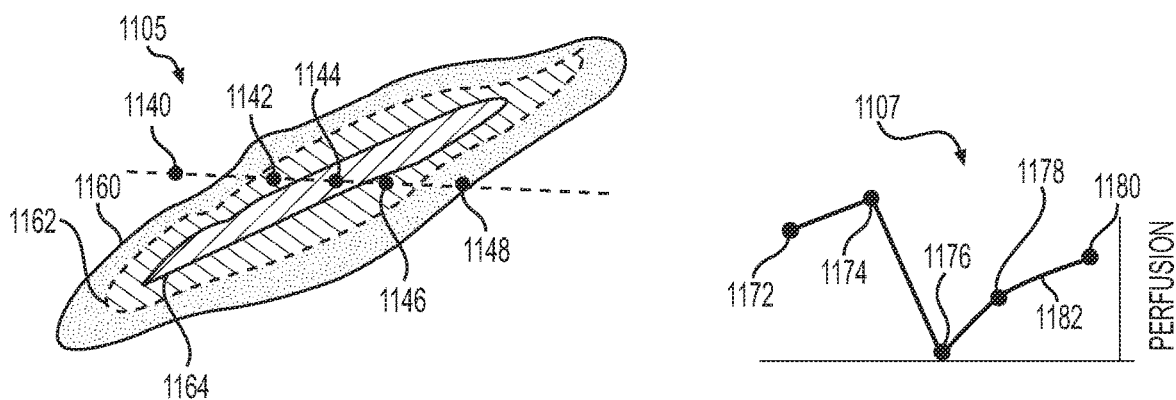
FIG. 11D  FIG. 11E

FIG. 16

| CURRENT LEVEL OF INTERVENTION | CURRENT "DELTA" VALUE (COMPARED TO THRESHOLD VALUE "T") | | | | | | |
|---|---|---|---|---|---|---|---|
| | 0 | <T | T+m | T+2m | T+3m | ... | ?T+S*m |
| 0 | 0 | 0 | 1 | 2 | 3 | ... | S |
| 1 | 0 | 1 | 2 | 3 | 4 | ... | S |
| 2 | 1 | 2 | 3 | 4 | 5 | ... | S |
| 3 | 2 | 3 | 4 | 5 | 6 | ... | S |
| 4 | 2 | 2 | 4 | 6 | 8 | ... | S |
| ... | ... | ... | ... | ... | ... | ... | ... |
| N | S-4 | S-2 | S-2 | S-1 | S | ... | S |

PERFUSION AND OXYGENATION MEASUREMENT

CROSS-REFERENCE TO RELATED APPLICATIONS

This application claims the benefit of priority of U.S. Provisional Application 62/698,684 filed Jul. 16, 2018, and U.S. Provisional Application 62/849,700 filed May 17, 2019, each of which is herein incorporated by reference in its entirety.

FIELD

The present disclosure provides methods and apparatus for evaluating the flow of blood in damaged or healing tissue. The present disclosure also provides methods of identifying a patient at the onset of risk of pressure ulcer or at risk of the onset of pressure ulcer, and treating the patient with anatomy-specific clinical intervention selected based on measurements of blood perfusion or oxygenation values, or a combination thereof. The present disclosure also provides methods of stratifying groups of patients based on the risk of wound development, and methods of reducing the incidence or severity of tissue damage in patients admitted to a care facility. The present disclosure also provides apparatuses and computer readable media for measuring blood perfusion in patients to identify damaged tissue for anatomy-specific clinical intervention, and methods for identifying damaged tissue. The present disclosure also provides methods of detecting tissue damage before the tissue damage is visible on a patient's skin.

BACKGROUND

The skin is the largest organ in the human body. It is readily exposed to different kinds of damages and injuries. Skin damage and injury may result when the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer. In the presence of other damage, such as the neuropathy and peripheral tissue weakening that can be induced by diabetes, even periodic exposure to moderate levels of pressure and stress may lead to an ulcer, for example a foot ulcer.

Pressure ulcers are developed by approximately 2.5 million people a year in the United States and an equivalent number in the European Union. In long-term and critical-care settings, up to 25% of elderly and immobile patients develop pressure ulcers. Approximately 60,000 U.S. patients die per year due to infection and other complications from pressure ulcers.

Most pressure ulcers occur over bony prominences, where there is less tissue for compression and the pressure gradient within the vascular network is altered. Pressure ulcers are categorized in one of six stages, ranging from the earliest stage currently recognized, in which the skin remains intact but may appear red over a bony prominence (Stage 1), to a stage where tissue is broken and bone, tendon or muscle is exposed (Stage 4), to deep tissue pressure injury showing non-blanchable deep red, maroon, or purple discoloration, and to a stage where there is obscured full-thickness skin and tissue loss (unstageable). Detecting pressure ulcers before the skin breaks and treating them to avoid progression to later stages is a goal of policy makers and care providers in major economies. Most pressure ulcers are preventable, and if identified before the first stage of ulceration, deterioration of the underlying tissue can be halted.

Detecting tissue damage before the skin breaks and intervening with the appropriate therapy to avoid further deterioration of the underlying tissue is desirable not only for the patient but society. The average cost of treating pressure-induced damage at the earliest visible sign (a Stage 1 ulcer) is only $2,000 but this rises to $129,000 when the ulcer is deep enough to expose muscle or bone (a Stage 4 ulcer). See, e.g., Brem, H. et al. (2010). High Cost of Stave IV Pressure Ulcers. *Am. J. Surg.* October; 200(4):473-477. Currently, patients normally receive universal prevention of pressure ulcers, meaning that the prevention does not target to any particular anatomical sites. Patients only receive a targeted, localized, treatment of ulcer after the pressure ulcer is developed to the point that it can be identified by a visual assessment. The current standard to detect pressure ulcers is by visual inspection, which is subjective, unreliable, untimely, and lacks specificity. See, e.g., Pancorbo-Hidalgo P. et al. (2006). Risk assessment scales for pressure ulcer prevention: a systematic review. *Journal of Advanced Nursing*, 54, 94-110; Garcia-Fernandez, F. P. (2014). Predictive Capacity of Risk Assessment Scales and Clinical Judgment for Pressure Ulcers: A Meta-analysis. *Journal of wound, Ostomy and Continence Nursing* 41, 24-34. Therefore, even when a patient is experiencing inflammation of the skin, a precursor of ulcer development, he or she would not be receiving a targeted, localized treatment for the developing ulcer. Instead, the inflammation would continue to develop into a full-blown ulcer.

Skin damage and injury may also result from certain types of surgical procedures, for example reconstructive surgery involving skin flaps, will sever blood vessels in or around the area of surgery. Healing of damaged or separated tissue is dependent upon re-establishment of adequate blood flow throughout the damaged area. Determining whether an area of tissue is healing, i.e. that blood flow through the tissue is increasing to a normal level, is difficult to do via visual inspection. Existing equipment can measure certain attributes, such as the oxygenation level of the blood, that are at best indirect measures of blood flow.

Fluorescein has been used for over 40 years to clinically assess flap vascularity. Fluorescein will emit a yellow-green (510-600 nm) fluorescence when excited by ultraviolet (UV) light. Tissue with good blood flow will appear bright yellow while areas without blood flow appear dark blue. Fluorescein is usually given in a bolus injection of 500-1000 mg. After waiting 20-30 min, the tissue can be assessed with a UV lamp. This method takes 30 minutes to implement and can only be used every 8 hours.

Near infrared spectroscopy (NIRS) is used to determine the ratio of oxygenated to de-oxygenated hemoglobin by proving specific wavelengths of light (760 nm and 830 nm) and measuring the amount of reflected or transmitted light. There are devices available now that provide images showing the local oxygenation of the skin surface. While this is an important piece of clinical information, it does not reveal the actual perfusion level of the tissue nor does it separate the condition of the surface tissue from the condition of the deeper layers of the tissue.

Two types of Doppler instruments are currently in clinical use. The first is the ultrasound Doppler, which senses the phase shift of reflected sound to measure the velocity of moving elements, presumed to be the red blood cells in a blood vessel. The second is the laser Doppler, which senses the phase shift of reflected light to detect the velocity of the red blood cells. These methods are limited to assessing the blood flow in the larger blood vessels and cannot assess perfusion in the finer arterioles and capillaries.

SUMMARY

Systematic methods using non-invasive, objective measurements to identify the onset of the risk of pressure ulcer before visible skin damages, followed by administering individualized intervention at specific anatomy are provided. Systematic methods using non-invasive, objective measurements to identify the onset of a pressure ulcer before visible skin damages, followed by administering individualized intervention at specific anatomy are also provided. Methods for monitoring progression of wound healing and consistency of intervention compliance are further provided.

In an aspect, the present disclosure provides for, and includes, an apparatus for assessing perfusion of blood in tissue below a patient's skin. The apparatus includes an emitter configured to emit light at a first wavelength and a second wavelength when activated, a first receiver configured to measure a first intensity of received light at the first wavelength and a second intensity of received light at the second wavelength and provide a first signal comprising information about the first and second intensities of the received light, a substrate coupled to the emitter and the first receiver and configured such that the emitter and first receiver can be placed in simultaneous contact with the patient's skin, and a processor coupled to the first receiver. The processor is configured to receive the first signal, determine a first summation value of the first and second intensities of the received light, and determine a level of perfusion of the tissue from the first summation value.

In an aspect, the present disclosure provides for, and includes, a method of assessing perfusion of blood in tissue below a patient's skin. The method includes the step of emitting light into the patient's skin at a first location on the patient's skin. The light has a first wavelength and a second wavelength. The method also includes the steps of receiving a portion of the emitted light that has been reflected from the tissue, measuring a first intensity of received light at the first wavelength and a second intensity of received light at the second wavelength, determining a first summation value of the first and second intensities of the received light.

In an aspect, the present disclosure provides for, and includes, an apparatus for assessing perfusion of blood in tissue below a patient's skin. The apparatus includes an emitter configured to selectably emit light at a first wavelength or emit light at a second wavelength, a camera configured to form a first image of reflected light at the first wavelength and a second image of reflected light at the second wavelength, and a substrate coupled to the emitter and the camera. The substrate can be placed such that the light emitted by the emitter illuminates a portion of the skin of the patient that is within a field of view of the camera. The apparatus also includes a display and a processor that is coupled to the camera and the display and configured to receive the first and second images, form a third image that is a summation of the first and second images, and provide the third image on the display.

In an aspect, the present disclosure provides for, and includes, a method of reducing the incidence of wound development in patients admitted to a care facility, the method comprising the steps of: evaluating a patient for a risk of tissue damage upon admission to the care facility, where the evaluating step comprises making a first plurality of perfusion measurements in the patient at one or more body locations at risk of wound development, calculating a first delta value from a portion of the first plurality of perfusion measurements, determining whether the first delta value exceeds a first threshold, administering a first intervention of level-0 if the first delta value does not exceed the first threshold, and administering an intervention of level-N if the first delta value exceeds the first threshold, where N is an integer and N has a value of 1 or greater. In one aspect, one or more body locations at risk of wound development are selected from the group consisting of a sternum, a sacrum, a heel, a scapula, an elbow, an ear, and other fleshy tissues over a bony prominence of a patient. In an aspect, one or more body locations at risk of wound development comprise one or more anatomical sites in long-term contact with a medical device, and are selected from the group consisting of a cheek, a nose, a chest, a stomach, and a lower abdomen area.

In an aspect, the present disclosure provides for, and includes, a method of reducing the incidence of wound development in patients admitted to a care facility, the method comprising the steps of: evaluating a patient for a risk of tissue damage upon admission to the care facility, where the evaluating step comprises making a first plurality of $SpO_2$ measurements in the patient at one or more body locations at risk of wound development, determining whether any of the first plurality of $SpO_2$ measurements is below a first threshold, administering a first intervention of level-0 if the first plurality of $SpO_2$ measurements are above or equal to the first threshold, and administering an intervention of level-N if any of the first plurality of $SpO_2$ measurements is below a first threshold, where N is an integer and N has a value of 1 or greater. In one aspect, one or more body locations at risk of wound development are selected from the group consisting of a sternum, a sacrum, a heel, a scapula, an elbow, an ear, and other fleshy tissues over a bony prominence of a patient. In an aspect, one or more body locations at risk of wound development comprise one or more anatomical sites in long-term contact with a medical device, and are selected from the group consisting of a cheek, a nose, a chest, a stomach, and a lower abdomen area.

In an aspect, the present disclosure provides for, and includes, a method of stratifying groups of patients in a care facility based on the risk of wound development, the method comprising the steps of: making a plurality of perfusion measurements in each of the patients at one or more body locations selected for monitoring, calculating a delta value from a portion of the plurality of perfusion measurements for each of the patients, determining whether each delta value exceeds any values in a set of threshold values corresponding to N care levels and assigning a care level to each of the patients, and rearranging the group of patients based on each of the patient's assigned care levels. In one aspect, one or more body locations for monitoring are selected from the group consisting of a sternum, a sacrum, a heel, a scapula, an elbow, an ear, and other fleshy tissues over a bony prominence of a patient. In an aspect, one or more body locations for monitoring comprise one or more anatomical sites in long-term contact with a medical device, and are selected from the group consisting of a cheek, a nose, a chest, a stomach, and a lower abdomen area.

In an aspect, the present disclosure provides for, and includes, a method of stratifying groups of patients in a care facility based on the risk of wound development, the method comprising the steps of: making a plurality of $SpO_2$ measurements in each of the patients at one or more body locations selected for monitoring, determining whether each of the plurality of $SpO_2$ measurements is below any values in a set of threshold values corresponding to N care levels and assigning a care level to each of the patients, and rearranging the group of patients based on each of the patient's assigned care levels. In one aspect, one or more body locations for monitoring are selected from the group consisting of a sternum, a sacrum, a heel, a scapula, an elbow, an ear, and other fleshy tissues over a bony prominence of a patient. In an aspect, one or more body locations for monitoring comprise one or more anatomical sites in long-term contact with a medical device, and are selected from the group consisting of a cheek, a nose, a chest, a stomach, and a lower abdomen area.

In an aspect, the present disclosure provides for, and includes, a method of identifying and providing an appropriate level of care to a patient based on a plurality of blood perfusion measurements of tissue below a patient's skin. In an aspect, a patient is provided with anatomy-specific intervention based on a plurality of blood perfusion measurements of tissue below a patient's skin. In an aspect, a patient is provided with increasingly intensive therapeutic interventions based on changes in perfusion measurements. In an aspect, a patient is given less intensive therapeutic interventions based on changes in perfusion measurements.

In an aspect, the present disclosure provides for, and includes, a method of identifying and providing an appropriate level of care to a patient based on a plurality of blood oxygenation ($SpO_2$) measurements of tissue below a patient's skin. In an aspect, a patient is provided with anatomy-specific intervention based on a plurality of $SpO_2$ measurements of tissue below a patient's skin. In an aspect, a patient is provided with increasingly intensive therapeutic interventions based on changes in $SpO_2$ measurements. In an aspect, a patient is given less intensive therapeutic interventions based on changes in $SpO_2$ measurements.

In an aspect, the present disclosure provides for, and includes, a method of assessing a patient, the method comprising the steps of: performing initial blood perfusion measurements of a location of the body selected for monitoring, and assigning the patient to a risk category selected from a group comprising a plurality of risk categories, where the assigning is based partially on the initial perfusion measurements of the body location.

In an aspect, the present disclosure provides for, and includes, a method of assessing a patient, the method comprising the steps of: performing initial $SpO_2$ measurements of a location of the body selected for monitoring, and assigning the patient to a risk category selected from a group comprising a plurality of risk categories, where the assigning is based partially on the initial $SpO_2$ measurements of the body location.

In an aspect, the present disclosure provides for, and includes, a method of managing care of a patient, the method comprising the steps of: performing an initial evaluation of the patient and taking an initial set of perfusion measurements at all body locations selected for monitoring upon admission to a care facility, calculating an initial delta value for each body location selected for monitoring, determining that a patient's measurements are abnormal and setting an intervention level to N=1 if any initial delta value is greater than or equal to a first threshold, implementing a level-N intervention for each body location having a delta value that is greater than or equal to the first threshold, and performing blood perfusion measurements of all body locations at a level-N frequency and calculating new delta values. In one aspect, one or more body locations for monitoring are selected from the group consisting of a sternum, a sacrum, a heel, a scapula, an elbow, an ear, and other fleshy tissues over a bony prominence of a patient. In an aspect, one or more body locations for monitoring comprise one or more anatomical sites in long-term contact with a medical device, and are selected from the group consisting of a cheek, a nose, a chest, a stomach, and a lower abdomen area.

In an aspect, the present disclosure provides for, and includes, a method of managing care of a patient, the method comprising the steps of: performing an initial evaluation of the patient and taking an initial set of $SpO_2$ measurements at all body locations selected for monitoring upon admission to a care facility, determining that a patient's measurements are abnormal and setting an intervention level to N=1 if any initial $SpO_2$ measurements is less than a first threshold, implementing a level-N intervention for each body location having a $SpO_2$ measurement that is less than the first threshold, and performing $SpO_2$ measurements of all body locations at a level-N frequency.

In an aspect, the present disclosure provides for, and includes, a method of identifying and treating a patient at risk of tissue damage, the method comprising the steps of: evaluating a patient for a risk of tissue damage upon admission to a care facility, where the evaluating step comprises making a first plurality of perfusion measurements in the patient, calculating a first delta value from a portion of the first plurality of perfusion measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater. In a further aspect, the present disclosure provides for, and includes, making a second plurality of perfusion measurements in the patient at a first pre-determined frequency corresponding to the administered intervention level, calculating a second delta value from a portion of the second plurality of perfusion measurements, determining whether the second delta value exceeds a second threshold, continuing to administer the first intervention if the second delta value does not exceed the second threshold, continuing to make a plurality of perfusion measurements at the first pre-determined frequency if the second delta value does not exceed the second threshold, administering a second intervention of level-M if the second delta value exceeds the second threshold, where M is an integer and M is greater than N, and making a plurality of perfusion measurements at a second pre-determined frequency corresponding to level-M if the second delta value exceeds the second threshold. In yet a further aspect, the present disclosure provides for, and includes, determining whether the second delta value is less than a third threshold, administering a level-(N−1) intervention if the second delta value is less than the third threshold and if the first intervention is not of level-0, and making a plurality of perfusion measurements at a pre-determined frequency corresponding to level-(N−1) if the second delta value is less than the third threshold.

In an aspect, the present disclosure provides for, and includes, a method of identifying and treating a patient at risk of tissue damage, the method comprising the steps of: evaluating a patient for a risk of tissue damage upon admission to a care facility, where the evaluating step comprises making a first plurality of $SpO_2$ measurements in the patient, determining whether any of the first plurality of $SpO_2$ measurements is below a first threshold, administering a first intervention of level-0 if the first plurality of $SpO_2$ measurements is greater than or equal to the first threshold, and administering a first intervention of level-N if any of the first plurality of $SpO_2$ measurements is below the first threshold, where N is an integer and N has a value of 1 or greater. In a further aspect, the present disclosure provides for, and includes, making a second plurality of $SpO_2$ measurements in the patient at a first pre-determined frequency corresponding to the administered intervention level, calculating a time delta value based on the differences between the first plurality and the second plurality of $SpO_2$ measurements, determining whether the time delta value is a decrease exceeding a second threshold, continuing to administer the first intervention if the time delta value does not exceed the second threshold, continuing to make a plurality of perfusion measurements at the first pre-determined frequency if the time delta value does not exceed the second threshold, administering a second intervention of level-M if the time delta value is a decrease exceeding the second threshold, where M is an integer and M is greater than N, and making a plurality of $SpO_2$ measurements at a second pre-determined frequency corresponding to level-M if the time delta value is a decrease exceeding the second threshold. In yet a further aspect, the present disclosure provides for, and includes, determining whether the time delta value is an increase exceeding a third threshold, administering a level-(N−1) intervention if the time delta value is an increase exceeding the third threshold and if the first intervention is not of level-0, and making a plurality of $SpO_2$ measurements at a pre-determined frequency corresponding to level-(N−1) if the time delta value is an increase exceeding the third threshold.

In an aspect, the present disclosure provides for, and includes, a method of slowing the progression of skin and tissue damage in a patient in need thereof, the method comprising the steps of: identifying a current intervention of level-K received by the patient, making a plurality of perfusion measurements in the patient, calculating a delta value from a portion of the plurality of perfusion measurements, determining whether the delta value exceeds a first threshold, continuing to administer the current intervention if the delta value does not exceed the first threshold, continuing to make a plurality of perfusion measurements at a pre-determined frequency corresponding to level-K if the delta value does not exceed the first threshold, administering a new intervention of level-N if the delta value exceeds the first threshold, where N has a value greater than K, and making a plurality of perfusion measurements at a pre-determined frequency corresponding to level-N if the delta value exceeds the first threshold. In a further aspect, the present disclosure provides for, and includes, determining whether the delta value is less than a second threshold, administering a level-L intervention if the delta value is less than the second threshold, where L has a non-negative value less than K, and making a plurality of perfusion measurements at a pre-determined frequency corresponding to level-L if the delta value is less than the second threshold.

In an aspect, the present disclosure provides for, and includes, a method of slowing the progression of skin and tissue damage in a patient in need thereof, the method comprising the steps of: identifying a current intervention of level-K received by the patient, making a plurality of $SpO_2$ measurements in the patient, determining whether any of the a plurality of $SpO_2$ measurements exceeds a first threshold, continuing to administer the current intervention if the plurality of $SpO_2$ measurements are within a threshold range corresponding to level-K, continuing to make a plurality of perfusion measurements at a pre-determined frequency corresponding to level-K if the delta value are within a threshold range corresponding to level-K, administering a new intervention of level-N if any of the plurality of $SpO_2$ measurements is below the first threshold range, where N has a value greater than K, and making a plurality of perfusion measurements at a pre-determined frequency corresponding to level-N if any of the plurality of $SpO_2$ measurements is below the first threshold range. In a further aspect, the present disclosure provides for, and includes, determining whether any of the plurality of $SpO_2$ measurements is above the threshold range corresponding to level-K, administering a level-L intervention if any of the plurality of $SpO_2$ measurements is above the threshold range corresponding to level-K, where L has a non-negative value less than K, and making a plurality of $SpO_2$ measurements at a pre-determined frequency corresponding to level-L if any of the plurality of $SpO_2$ measurements is above the threshold range corresponding to level-K.

In an aspect, the present disclosure provides for, and includes, a method of identifying and treating a patient in need of application of a barrier cream to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a barrier cream to the patient's heel if the delta value exceeds the threshold, and making a plurality of perfusion measurements every two hours if the delta value exceeds the threshold.

In an aspect, the present disclosure provides for, and includes, a method of identifying and treating a patient in need of application of a barrier cream to the patient's heel, the method comprising the steps of: making a plurality of $SpO_2$ measurements at the patient's heel, determining whether any of the plurality of $SpO_2$ measurements is below a threshold corresponding to level N, where N is greater than or equal to 2, administering a barrier cream to the patient's heel if any of the plurality of $SpO_2$ measurements is below the threshold, and making a plurality of $SpO_2$ measurements every two hours if any of the plurality of $SpO_2$ measurements is below the threshold.

In one aspect, the present disclosure provides for, and includes, a method of identifying and treating a patient in need of application of a neuro-muscular stimulation to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a neuro-muscular stimulation to the patient's heel if the delta value exceeds the threshold, and making a plurality of perfusion measurements every hour if the delta value exceeds the threshold.

In an aspect, the present disclosure provides for, and includes, a method of identifying and treating a patient in need of application of a neuro-muscular stimulation to the patient's heel, the method comprising the steps of: making a plurality of $SpO_2$ measurements at the patient's heel, determining whether any of the plurality of $SpO_2$ measurements is below a threshold corresponding to level N, where N is greater than or equal to 2, administering a neuro-muscular stimulation to the patient's heel if any of the plurality of $SpO_2$ measurements is below the threshold, and making a plurality of $SpO_2$ measurements every hour if any of the plurality of $SpO_2$ measurements is below the threshold.

In an aspect, the present disclosure provides for, and includes, a method of identifying and treating a patient in need of application of a topical cream to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a topical cream to the patient's heel if the delta value exceeds the threshold, and making a plurality of perfusion measurements every half an hour if the delta value exceeds the threshold.

In an aspect, the present disclosure provides for, and includes, a method of identifying and treating a patient in need of application of a topical cream to the patient's heel, the method comprising the steps of: making a plurality of $SpO_2$ measurements at the patient's heel, determining whether any of the plurality of $SpO_2$ measurements is below a threshold corresponding to level N, where N is greater than or equal to 2, administering a topical cream to the patient's heel if any of the plurality of $SpO_2$ measurements is below the threshold, and making a plurality of $SpO_2$ measurements every half an hour if any of the plurality of $SpO_2$ measurements is below the threshold.

In an aspect, the present disclosure provides for, and includes, a method of identifying and treating a patient in need of application of a heel boot to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a heel boot to the patient's heel if the delta value exceeds the threshold, and making a plurality of perfusion measurements every half an hour if the delta value exceeds the threshold.

In an aspect, the present disclosure provides for, and includes, a method of identifying and treating a patient in need of application of a heel boot to the patient's heel, the method comprising the steps of: making a plurality of $SpO_2$ measurements at the patient's heel, determining whether any of the plurality of $SpO_2$ measurements is below a threshold corresponding to level N, where N is greater than or equal to 2, administering a heel boot to the patient's heel if any of the plurality of $SpO_2$ measurements is below the threshold, and making a plurality of $SpO_2$ measurements every half an hour if any of the plurality of $SpO_2$ measurements is below the threshold.

In one aspect, the present disclosure provides for, and includes, a method of identifying and treating a patient in need of application of a barrier cream to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a barrier cream to the patient's sacrum if the delta value exceeds the threshold, and making a plurality of perfusion measurements every six hours if the delta value exceeds the threshold.

In an aspect, the present disclosure provides for, and includes, a method of identifying and treating a patient in need of application of a barrier cream to the patient's sacrum, the method comprising the steps of: making a plurality of $SpO_2$ measurements at the patient's sacrum, determining whether any of the plurality of $SpO_2$ measurements is below a threshold corresponding to level N, where N is greater than or equal to 2, administering a barrier cream to the patient's sacrum if any of the plurality of $SpO_2$ measurements is below the threshold, and making a plurality of $SpO_2$ measurements every six hours if any of the plurality of $SpO_2$ measurements is below the threshold.

In an aspect, the present disclosure provides for, and includes, a method of identifying and treating a patient in need of application of a neuro-muscular stimulation to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a neuro-muscular stimulation to the patient's sacrum if the delta value exceeds the threshold, and making a plurality of perfusion measurements every four hours if the delta value exceeds the threshold.

In an aspect, the present disclosure provides for, and includes, a method of identifying and treating a patient in need of application of a neuro-muscular stimulation to the patient's sacrum, the method comprising the steps of: making a plurality of $SpO_2$ measurements at the patient's sacrum, determining whether any of the plurality of $SpO_2$ measurements is below a threshold corresponding to level N, where N is greater than or equal to 2, administering a neuro-muscular stimulation to the patient's sacrum if any of the plurality of $SpO_2$ measurements is below the threshold, and making a plurality of $SpO_2$ measurements every four hours if any of the plurality of $SpO_2$ measurements is below the threshold.

In one aspect, the present disclosure provides for, and includes, a method of identifying and treating a patient in need of application of a topical cream to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a topical cream to the patient's sacrum if the delta value exceeds the threshold, and making a plurality of perfusion measurements every two hours if the delta value exceeds the threshold.

In an aspect, the present disclosure provides for, and includes, a method of identifying and treating a patient in need of application of a topical cream to the patient's sacrum, the method comprising the steps of: making a plurality of $SpO_2$ measurements at the patient's sacrum, determining whether any of the plurality of $SpO_2$ measurements is below a threshold corresponding to level N, where N is greater than or equal to 2, administering a topical cream to the patient's sacrum if any of the plurality of $SpO_2$ measurements is below the threshold, and making a plurality of $SpO_2$ measurements every two hours if any of the plurality of $SpO_2$ measurements is below the threshold.

In one aspect, the present disclosure provides for, and includes, a method of identifying and treating a patient in need of application of therapeutic ultrasound, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering therapeutic ultrasound to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of therapeutic ultrasound, the method comprising the steps of: making a plurality of $SpO_2$ measurements at an anatomic site of the patient, determining whether any of the plurality of $SpO_2$ measurements is below a threshold corresponding to level N, where N is greater than or equal to 2, administering therapeutic ultrasound to the anatomic site if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of application of shockwave therapy, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering shockwave therapy to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient. In one aspect, shockwave therapy is provided via electromagnetic pulse or pressurized air.

In an aspect, the present disclosure provides for, and includes, a method of identifying and treating a patient in need of application of shockwave therapy, the method comprising the steps of: making a plurality of $SpO_2$ measurements at an anatomic site of the patient, determining whether any of the plurality of $SpO_2$ measurements is below a threshold corresponding to level N, where N is greater than or equal to 2, administering shockwave therapy to the anatomic site if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient. In one aspect, shockwave therapy is provided via electromagnetic pulse or pressurized air.

In one aspect, the present disclosure provides for, and includes, a method of identifying and treating a patient in need of application of a 30-degree wedge, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering a 30-degree wedge to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a 30-degree wedge, the method comprising the steps of: making a plurality of $SpO_2$ measurements at an anatomic site of the patient, determining whether any of the plurality of $SpO_2$ measurements is below a threshold corresponding to level N, where N is greater than or equal to 2, administering a 30-degree wedge to the anatomic site if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of application of a composite dressing, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering a composite dressing to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a composite dressing, the method comprising the steps of: making a plurality of $SpO_2$ measurements at an anatomic site of the patient, determining whether any of the plurality of $SpO_2$ measurements is below a threshold corresponding to level N, where N is greater than or equal to 2, administering a composite dressing to the anatomic site if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of a hybrid mattress, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, providing a hybrid mattress to support the patient if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a hybrid mattress, the method comprising the steps of: making a plurality of $SpO_2$ measurements at an anatomic site of the patient, determining whether any of the plurality of $SpO_2$ measurements is below a threshold corresponding to level N, where N is greater than or equal to 2, providing a hybrid mattress to support the patient if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of a dynamic mattress, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, providing a dynamic mattress to support the patient if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a dynamic mattress, the method comprising the steps of: making a plurality of $SpO_2$ measurements at an anatomic site of the patient, determining whether any of the plurality of $SpO_2$ measurements is below a threshold corresponding to level N, where N is greater than or equal to 2, providing a dynamic mattress to support the patient if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, an apparatus for identifying damaged tissue, the apparatus comprising: a perfusion measurement device of the present disclosure for assessing perfusion of blood in tissue below a patient's skin; a processor electronically coupled to the perfusion measurement device and configured to receive the information from the perfusion measurement device and convert the information regarding the measured reflected light into a perfusion value; and a non-transitory computer-readable medium electronically coupled to the processor and comprising instructions stored thereon that, when executed on the processor, perform the step of: determining a difference between a first perfusion value corresponding to a measurement taken at a first location on the patient's skin and a second perfusion value corresponding to a measurement taken at a second location on the patient's skin, where the second location is bisymmetric relative to the first location.

In an aspect, an apparatus for identifying damaged tissue is provided by the present disclosure, the apparatus comprising: a substrate configured to be placed against a surface of a patient's skin; a perfusion measurement device of the present disclosure for assessing perfusion of blood in tissue below a patient's skin, comprising a plurality of emitters and a plurality of receivers that are disposed on the substrate a respective plurality of positions; a processor electronically coupled to the perfusion measurement device and configured to receive information regarding the reflected light measurements from the plurality of receivers and convert the information into a respective plurality of perfusion values; and a non-transitory computer-readable medium electronically coupled to the processor and comprising instructions stored thereon that, when executed on the processor, perform the steps of: identifying from the plurality of perfusion values a first receiver and a second receiver that are located at first and second positions that are bisymmetric to one another with respect to the patient's skin, and comparing a first perfusion value that is associated with the first receiver with a second perfusion value that is associated with the second receiver.

In an aspect, an apparatus for identifying damaged tissue is provided by the present disclosure, the apparatus comprising: an apparatus body; at least one emitter; a first receiver and a second receiver, where the two receivers are disposed on the apparatus body to allow simultaneous positioning of the first receiver on a first location on a patient's skin and the second receiver on a second location bisymmetric relative to the first location; a processor electronically coupled to the two receivers and configured to receive a first reflected light measurement from a first location and a second reflected light measurement from a second location, and to convert the first reflected light measurement to a first perfusion value and the second reflected light measurement into a second perfusion value; a non-transitory computer-readable medium electronically coupled to the processor and contains instructions that, when executed on the processor, perform the step of determining a difference between the first perfusion value and the second perfusion value.

In an aspect, a method for identifying damaged tissue is provided by the present disclosure, the method comprising: obtaining a first perfusion value from a first location on a patient's skin; obtaining a second perfusion value from a second location that is bisymmetric relative to the first location; determining a difference between a first perfusion value and a second perfusion value.

In an aspect, the present disclosure provides for, and includes, a method of detecting tissue damage before it is visible on a patient's skin, comprising: measuring a plurality of perfusion values at a single location at incremental times, calculating a slope between the latest perfusion value and the immediately prior perfusion value, comparing this slope to a threshold value, and determining that there is tissue damage if the slope exceeds the threshold value.

In an aspect, the present disclosure provides for, and includes, a method of detecting tissue damage before it is visible on a patient's skin, comprising: measuring a plurality of perfusion values at a plurality of locations at incremental times, calculating a delta value for the plurality of perfusion values for each time, calculating a slope between the latest delta value and the immediately prior delta value, comparing this slope to a threshold value, and determining that there is tissue damage if the slope exceeds the threshold value.

In an aspect, the present disclosure provides for, and includes, a method of detecting tissue damage before it is visible on a patient's skin, comprising: measuring a plurality of perfusion values at a plurality of locations at incremental times, calculating a delta value for the plurality of perfusion values for each time, calculating a derivative between the latest delta value and the immediately prior delta value, comparing this derivative to a threshold value, and determining that there is tissue damage if the derivative exceeds the threshold value.

In an aspect, the present disclosure provides for, and includes, a method of detecting tissue damage before it is visible on a patient's skin, comprising: measuring a plurality of perfusion values at a single location at each of a plurality of incremental times, calculating a perfusion delta value for each incremental time, fitting a curve to a predetermined number of the most-recent perfusion delta values, calculating a curvature of the fitted curve, comparing this curvature to a threshold value, and determining that there is tissue damage if the curvature exceeds the threshold value.

In an aspect, the present disclosure provides for, and includes, a method of detecting tissue damage before it is visible on a patient's skin, comprising: measuring a plurality of $SpO_2$ values at a single location at incremental times, calculating a slope between the latest $SpO_2$ value and the immediately prior $SpO_2$ value, comparing this slope to a threshold value, and determining that there is tissue damage if the slope exceeds the threshold value.

In an aspect, the present disclosure provides for, and includes, a method of detecting tissue damage before it is visible on a patient's skin, comprising: measuring a plurality of $SpO_2$ values at a single location at incremental times, calculating a derivative between the latest $SpO_2$ value and the immediately prior $SpO_2$ value, comparing this derivative to a threshold value, and determining that there is tissue damage if the derivative exceeds the threshold value.

In an aspect, the present disclosure provides for, and includes, a method of detecting tissue damage before it is visible on a patient's skin, comprising: measuring a plurality of $SpO_2$ values at a single location at each of a plurality of incremental times, calculating an average value for each incremental time, fitting a curve to a predetermined number of the most-recent $SpO_2$ average values, calculating a curvature of the fitted curve, comparing this curvature to a threshold value, and determining that there is tissue damage if the curvature exceeds the threshold value.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

FIG. 1 depicts the tissue around a burn.

FIGS. 2A and 2B depict a skin flap created as part of breast reconstruction surgery.

FIGS. 11A and 11B depict the detected signals of light reflected from oxygenated and de-oxygenated hemoglobin along a line across a wound, in accordance with the present disclosure.

FIG. 11C is a plot of comparative points of the curves of FIGS. 11A and 11B, in accordance with the present disclosure.

FIG. 11D depict an example wound and an exemplary map of the line of measurements of the plot of FIG. 11C, in accordance with the present disclosure system.

FIG. 11E depicts an example plot of perfusion summation values taken across a different wound, in accordance with the present disclosure.

FIG. 16 is an example of a workflow guidance matrix where the current level of intervention and the new delta value are used to select the new level of intervention in accordance with the present disclosure.

DETAILED DESCRIPTION

Figure 3:
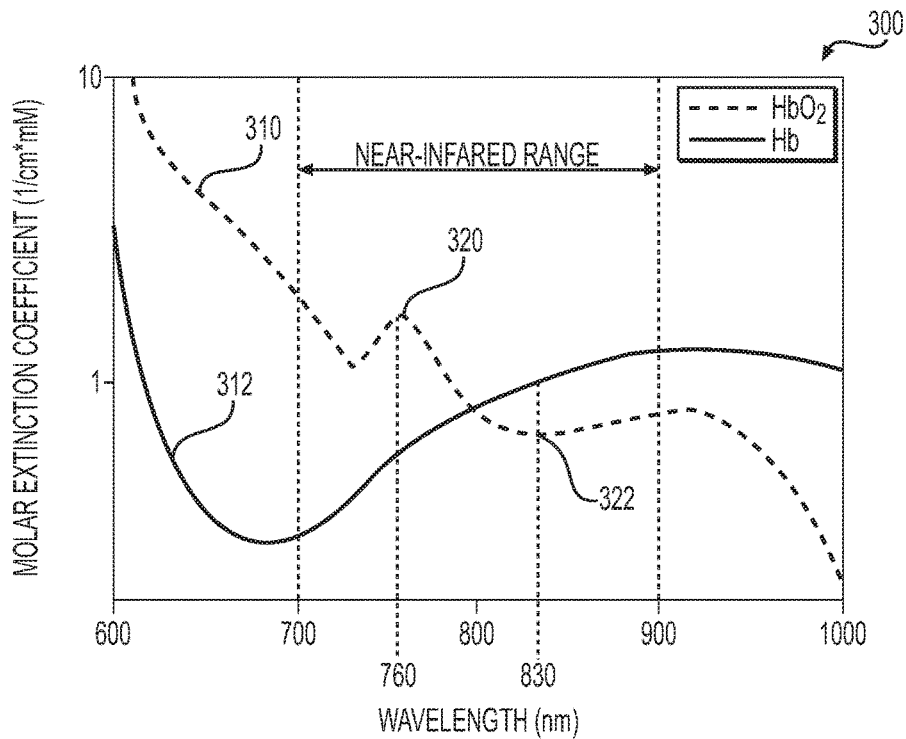
FIG. 3 is a representative plot of the absorption spectrum of oxygenated and de-oxygenated hemoglobin.

This description is not intended to be a detailed catalog of all the different ways in which the disclosure may be implemented, or all the features that may be added to the instant disclosure. For example, features illustrated with respect to one embodiment may be incorporated into other embodiment, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a perfusion value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "exemplary" is used to mean serving as an example, instance, or illustration. Any embodiment or aspect described as "exemplary" is not necessarily to be construed as preferred or advantageous over other embodiments or aspects, nor is it meant to preclude equivalent structures and techniques known to those of ordinary skill in the art. Rather, use of the word exemplary is intended to present concepts in a concrete fashion, and the disclosed subject matter is not limited by such examples.

As used herein, the term "patient" comprises both human and animal subjects.

As used herein, the term "skin" indicates the surface of a patient's body.

As used herein, the term "tissue" includes a plurality of layers of the patient's body starting from the stratum corneum and including additional deeper structures such as the epidermis, the dermis, and a portion of deeper tissue that includes blood vessels. In an aspect, tissue does not include the outermost surface of a patient's body.

As used herein, the term "wound" refers to damaged or injured tissue, which may or may not be visible on the surface of the skin. A wound may be open or closed. A wound may arise from a surgical procedure. A wound may be a burn wound. In an aspect, a wound is a pressure ulcer. In a further aspect, the pressure ulcer is subcutaneous. In one aspect, a pressure ulcer is a pressure ulcer resulting from an extended period of use of a medical device such as, for example, a mask, a tubing, or a strap. In an aspect, a wound is a diabetic foot ulcer. In an aspect, a wound is a vascular ulcer.

As used herein, the term "delta" refers to a calculated difference between two values derived from measurements obtained approximately the same time from a subject. In an aspect, each of the values is a summation value calculated from measurements obtained approximately the same time. In an aspect, measurements are obtained approximately the same time when they are taken within about one hour, such as less than about 30 minutes, less than about 20 minutes, less than about 10 minutes, less than about 5 minutes, less than about 4 minutes, less than about 3 minutes, less than about 2 minutes, less than about 1 minute, or less than about 30 seconds.

As used herein, the term "time delta" refers to a calculated difference between two values derived from measurements obtained at different time from a subject. In an aspect, each of the values is an average value calculated from measurements obtained approximately the same time. In an aspect, each of the values is a summation value calculated from measurements obtained approximately the same time. In an aspect, measurements are obtained approximately the same time when they are taken apart by more than about one hour, such as more than about 2 hours, such as more than about 3 hours, such as more than about 4 hours, such as more than about 5 hours, such as more than about 6 hours, such as more than about 8 hours, or such as more than about 10 hours.

As used herein, the variables "K," "L," "M," and "N" are non-negative integers.

As used herein, the term "anatomy-specific" refers to the application of clinical interventions to the same locations where certain perfusion or $SpO_2$ measurements are taken.

As used herein, a "system" may be a collection of devices in wired or wireless communication with each other.

As used herein, "bisymmetric" refers to a pair of locations that are approximately equidistant from a line of symmetry.

As used herein, the term "camera" comprises any device that captures independent information about a plurality of points distributed across a two-dimensional area without contacting the points.

As used herein, the term "light" means electromagnetic energy having a wavelength within the range of 1 picometer to 1 meter. In an aspect, this range is 1 nanometer to 1 millimeter, encompassing "ultraviolet," "visible," and "infrared" light. In an aspect, this range is 10-390 nanometers, which is commonly understood to be "ultraviolet" light. In an aspect, this range is 390-700 nanometers, which is commonly understood to be "visible" light. In an aspect, this range is 700 nanometers to 1 millimeter, which is commonly understood to be "infrared" radiation. In an aspect, this range is 700-900 nanometers, which is commonly understood to be "near infrared" radiation. In an aspect, this light may be a narrow band of wavelengths about a particular wavelength. In an aspect, the particular wavelength is 760 and/or 830 nanometers.

Within this document, identification of light as having a certain wavelength has the same meaning as identifying the light as having a certain frequency, as the wavelength and frequency of light are uniquely related. Reference to a frequency of light is considered equivalent and interchangeable with a reference to the wavelength of the same light.

As used herein, the term "method" comprises a sequence of activities, e.g. steps. In certain embodiments, the steps must be performed in a particular order while, in other embodiments, the sequence of activities may be interchanged. A "method" is considered equivalent to and interchangeable with a "process." In certain embodiments, one or more disclosed steps are omitted.

Perfusion and Oxygenation Measurements

FIG. 1 depicts the tissue around a burn 102 in tissue 100 of a patient. Tissue 100 has a surface epidermis layer 110, a layer of dermis 120, and a subcutaneous layer 130. Blood vessels 180 in layer 130 connect to arterioles 182 that penetrate layers 120 and 110.

Burn 102 has a central region 150 that is a "zone of necrosis," which is primarily dead tissue with a low moisture content. Surrounding region 150 is a region 160 that is a "zone of stasis," which is tissue that is characterized by decreased tissue perfusion. The tissue in region 160 is potentially salvageable and is of particular interest to a clinician as this is the area of focus in treating a burn. The next region 170 is a zone of hyperemia wherein tissue perfusion is increased because local production of inflammatory mediators in region 170 causes dilatation of blood vessels.

FIGS. 2A and 2B depict a skin flap 240 created as part of breast reconstruction surgery. In this example, a section of skin 210 is removed from the back over the latissimus dorsi muscle 220 as shown in FIG. 2A. Skin 210 is placed in location 240 to provide additional surface to cover the implant 230 as shown in FIG. 2B. Location 222 in FIG. 2B indicates the location from which flap 210 was removed.

FIG. 3 is a representative plot 300 of the absorption spectrum of oxygenated hemoglobin 310 and de-oxygenated hemoglobin 312. Oxygenated curve 310 has a local peak 320 at 760 nanometers, which creates a difference between the local maximum of curve 310 and curve 312 at this wavelength. At 830 nanometers, curve 310 has a local minimum 322 that also creates a local maximum in the difference between curves 310 and 312. Lasers are commonly available that emit light having a wavelength in the range of 760-830 nanometers.

Figure 4:
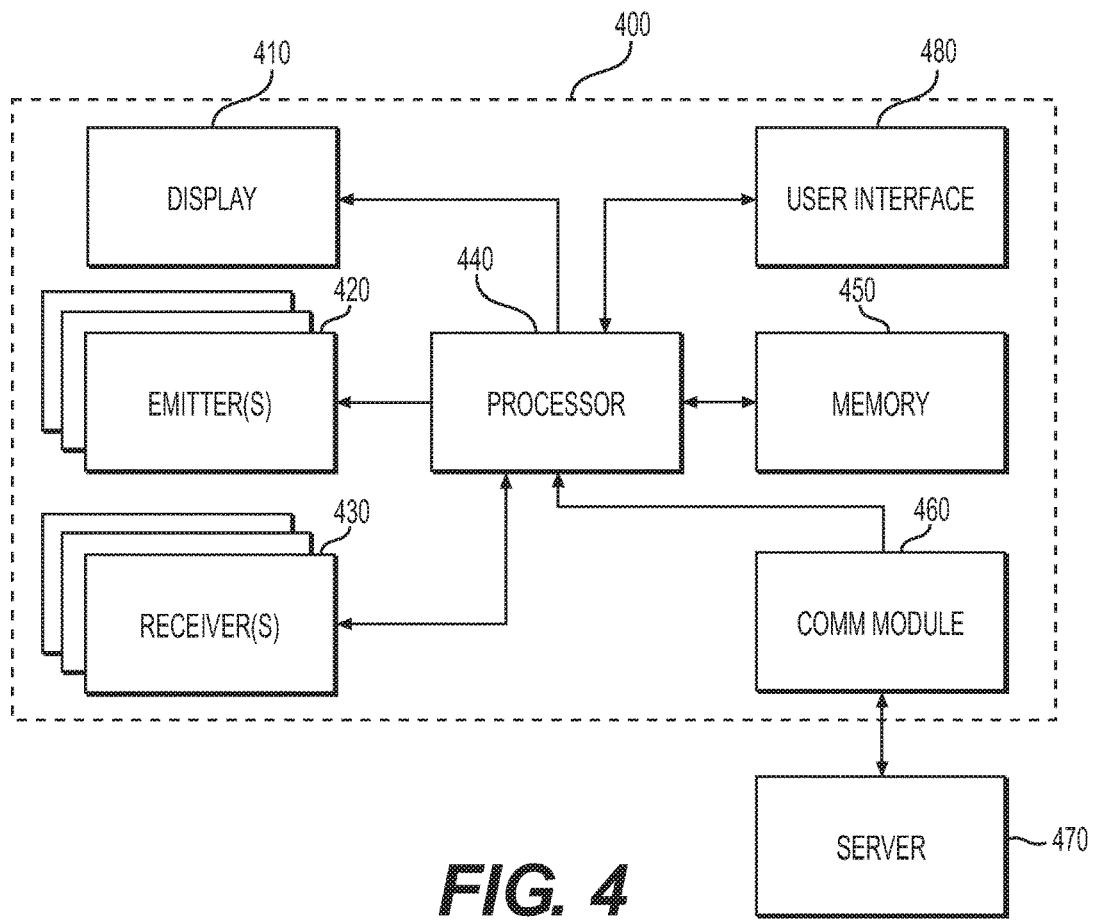
FIG. 4 depicts a block diagram of an example perfusion measurement device, in accordance with the present disclosure.

FIG. 4 depicts a block diagram of an example perfusion measurement device 400, in accordance with the present disclosure. Device 400 comprises a processor 440 that is connected to a display 410 and user interface 480. Processor 440 is also coupled to a memory 450, a communication module 460, an emitter 420, and a receiver 430.

In an aspect, memory 450 is nonvolatile and contains instructions that, when loaded into and executed on processor 440, cause processor 440 to execute one or more steps of a process.

In an aspect, emitter 420 is configured to emit light and receiver 430 is configured to detect light. In an aspect, receiver 430 provides a signal to the processor 440 that comprising information about the received light. In one aspect, this information comprises one or more data selected from the group consisting of a value of the intensity of the detected light, a wavelength of the detected light, a timing of the detected light, and a duration of the detected light.

In an aspect, emitter 420 and/or receiver 430 comprise a filter (not visible in FIG. 4) that passes only light having a wavelength within one or more defined ranges. In an aspect, there are multiple emitters 420 and/or multiple receivers 430 that emit and detect light at a common wavelength or at different frequencies. For example, a first emitter 420 emits light at 760 nanometers while a second emitter 420 emits light at 830 nanometers. In an aspect, a single emitter 420 emits light at both 760 and 830 nanometers. For example, a first receiver 430 detects light at 760 nanometers while a second receiver 430 detects light at 830 nanometers. In an aspect, a single receiver detects light at both 760 and 830 nanometers.

Figure 5:
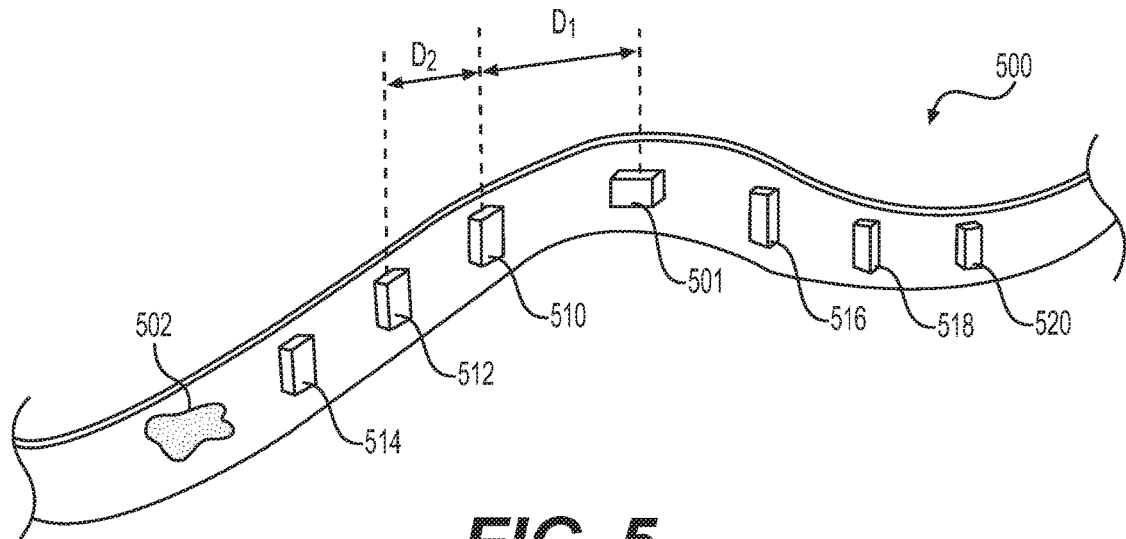
FIG. 5 depicts an exemplary configuration of a perfusion measurement device, in accordance with the present disclosure.

FIG. 5 depicts an exemplary configuration of a perfusion measurement device 500, in accordance with the present disclosure. Device 500 comprises a substrate 502 to which are attached an emitter 501 and a plurality of receivers 510, 512, 514, 516, 518, and 520. Receiver 510 is spaced apart from emitter 501 by a first distance D1 while receivers 510 and 512 are spaced apart by a second distance D2. In an aspect, substrate 502 is flexible as shown in FIG. 5. In another aspect, substrate 502 is rigid and/or comprises a rigid element.

Figure 6:
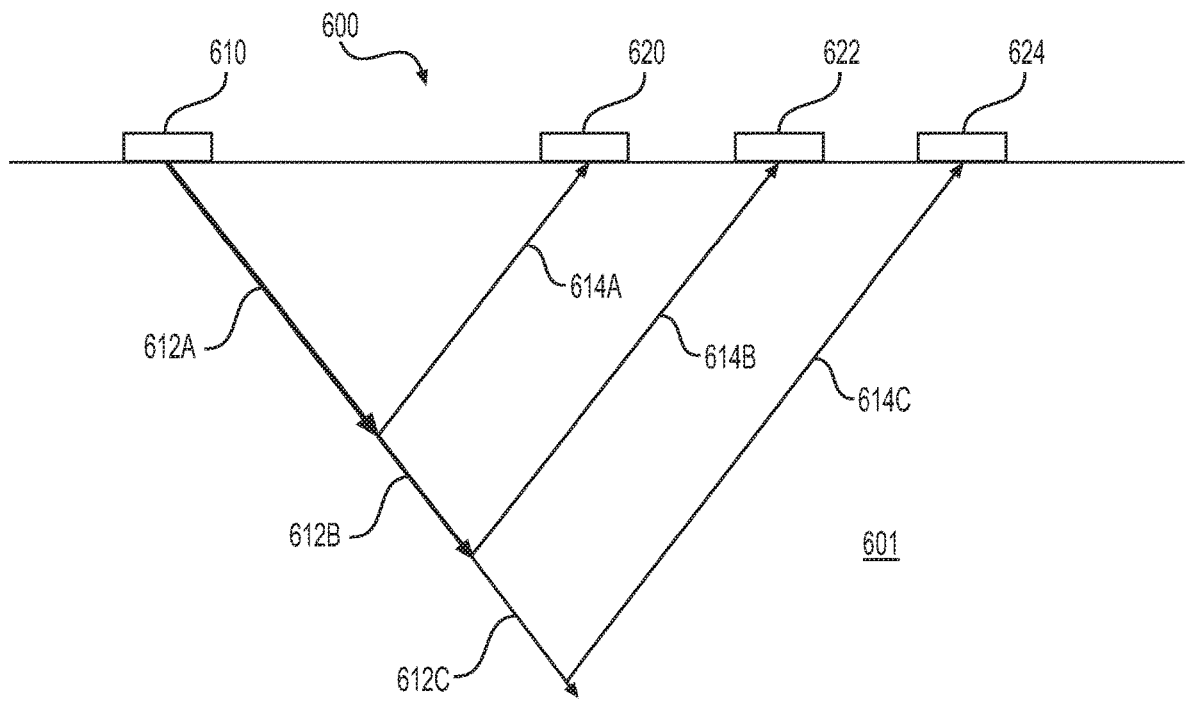
FIG. 6 depicts a cross-section of tissue showing how emitted light is reflected by the tissue, in accordance with the present disclosure.

FIG. 6 depicts a schematic cross-section of tissue 601 showing how light emitted by emitter 610 is reflected by the tissue 601, in accordance with the present disclosure. The light 612A is emitted at a first intensity. Part of light 612A is reflected at a first depth as light 614A while the remainder continues as light 612B. Similarly, part of light 612B is reflected a second depth as light 614B while the remainder continues as light 612C. In this example, a portion of light 612C is reflected as light 614C while the remainder is lost in the deeper tissue 601.

Still referring to FIG. 6, receivers 620, 622, and 624 are placed at distances from emitter 610 such that they respectively receive light 614A, 614B, and 614C. The intensity of each light 614A, 614B, and 614C comprises information about the tissue along the entire respective path from the emitter 610 to the particular receiver. In an aspect, information about the portion of the path of light 612B that is below light 612A and above light 612C is extracted by comparing the information about the light detected by receiver 622 to one or both of the light 614A and 614C that are received by receivers 620 and 624. In an aspect, this comparison is made by subtraction of the intensity of the light received by receiver 620 from the intensity of the light received by receiver 622. In an aspect, the information to be compared comprises intensities of one or more of light 614A, 614B, and 614C.

Figure 7:
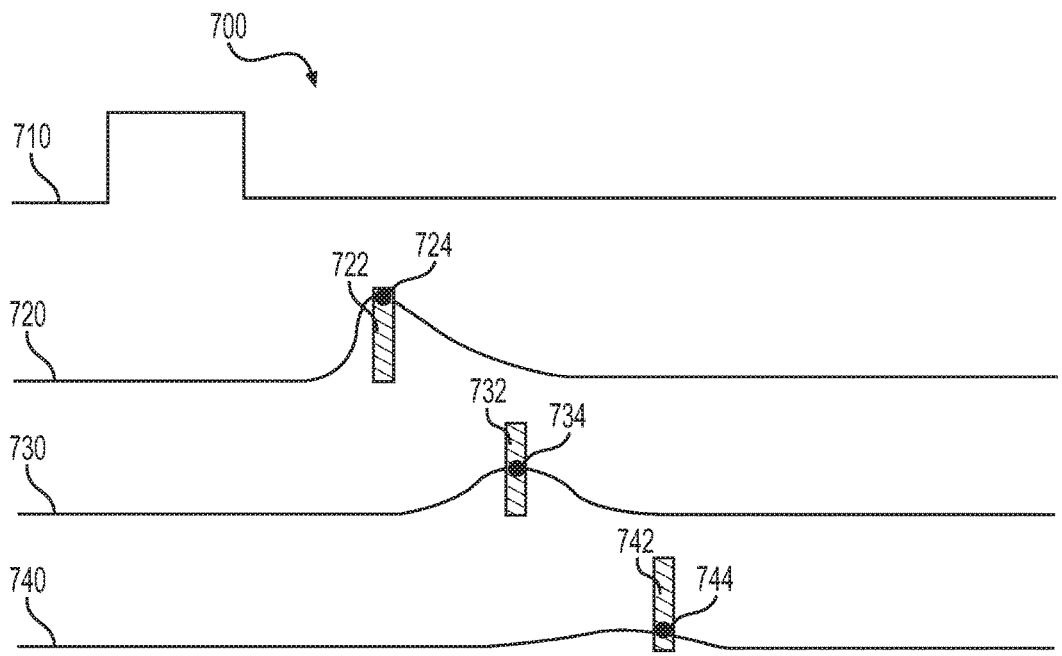
FIG. 7 depicts the emitted and detected signals of an example system, in accordance with the present disclosure.

FIG. 7 depicts the emitted signal 710 and detected signals 720, 730, and 740 of an example system 700, in accordance with the present disclosure. In this example, signal 720 is detected by a first receiver and has peak value 724, signal 730 is detected by a second receiver and has peak value 734, and signal 740 is detected by a third receiver and has peak value 744. As shown in FIG. 7, peak values 724, 734, and 744 are time-shifted from the emitted pulse in relation to the path length of the light from the emitter to the respective receiver. In this example, waveforms of signals 720, 730, and 740 have shapes that reflect detection of light that has traveled on multiple different paths from the emitter to the respective receiver.

In an aspect, time windows 722, 732, and 742 are imposed on the signals 720, 730, and 740 to detect only light that has traveled along a defined path from the emitter to the receiver. In one aspect, multiple time windows (not shown in FIG. 7) are imposed on a single signal to capture information about light that has traveled on different paths.

Figure 8:
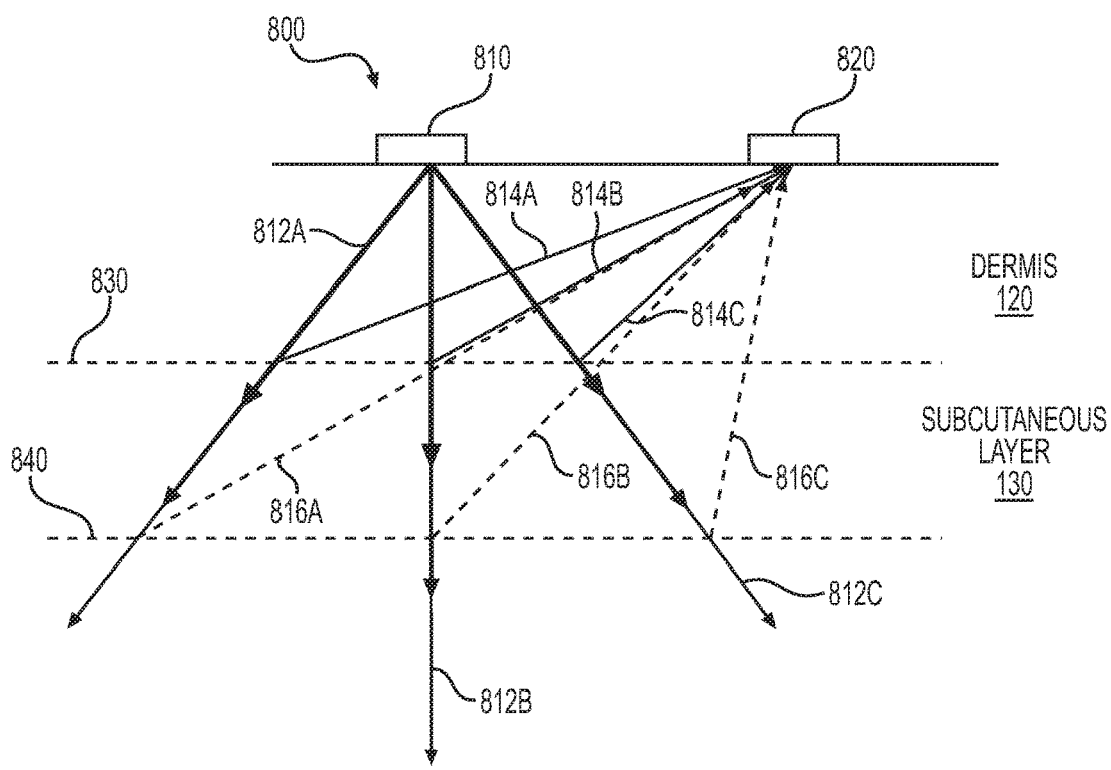
FIG. 8 depicts the paths of reflected light with a wide-angle source, in accordance with the present disclosure.

FIG. 8 depicts example paths 812A, 812B, and 812C of reflected light with a wide-angle source in emitter 810, in accordance with the present disclosure. A wide-angle source emits light over a solid angle, for example a 30 degree cone. In an aspect, this cone may be oriented vertically, i.e. perpendicular to the skin, while in another aspect the cone may be at an angle to the skin. In one aspect, the emitted light may be non-symmetric about an axis.

Beams of light 812A, 812B, and 812C are each emitted at different angles. At an example depth 830, for example at the bottom of the dermis layer 120, light beams 814A,814B, and 814C are reflected in a diffuse manner from the respective beams 812A, 912B, and 812C toward a common receiver 820. Similarly at depth 840, for example at the bottom of subcutaneous layer 130, beams 816A, 816B, and 816C are reflected toward the same receiver 820. The light detected by receiver 820 contains time and intensity information about light that has followed multiple paths from the emitter 810.

Figure 9:
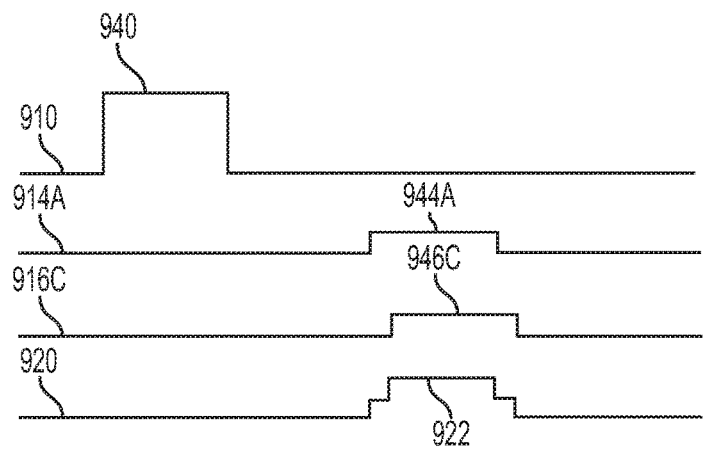
FIG. 9 depicts the emitted signal and detected signals of a system similar to that of FIG. 8, in accordance with the present disclosure.

FIG. 9 depicts emitted signal 910 and detected signals 914A and 916C of a system similar to that of FIG. 8, in accordance with the present disclosure. In this example, the emitter emits a pulse of light 940 that comprises light at two frequencies. Light at the first wavelength 914A is detected as pulse 944A and light at the second wavelength is detected as pulse 946C. In an aspect, the timing of pulses 944A and 946A are adjusted before being summed together. In another aspect, the timing of pulses 944A and 946A are not adjusted before being summed together.

In an aspect, signals 914A and 916C are added together to form signal 920 that represents the timing and intensity of light reflected from both oxygenated and de-oxygenated hemoglobin.

Figure 10A:
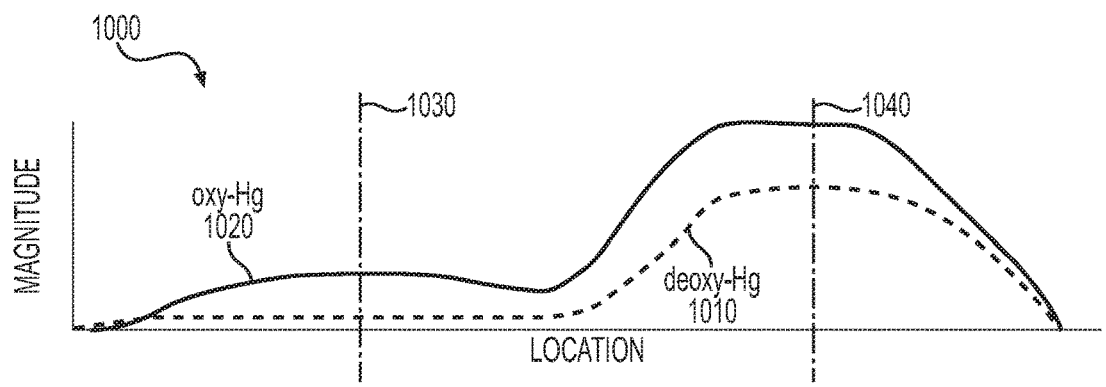
FIGS. 10A and 10B depict the detected signals of light reflected from oxygenated and de-oxygenated hemoglobin, in accordance with the present disclosure.
Figure 10B:
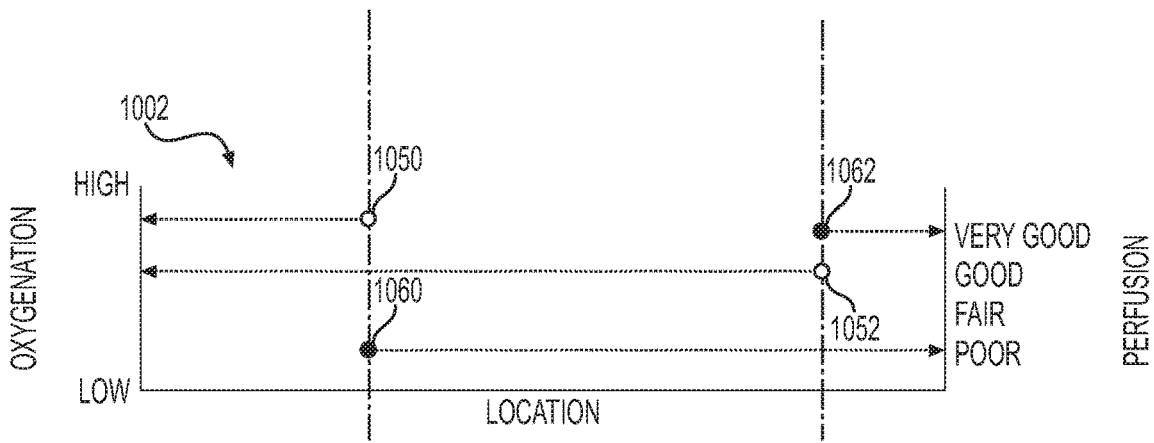

FIGS. 10A and 10B depict the detected signals of light reflected at various points located across a wound from oxygenated hemoglobin 1020 and de-oxygenated hemoglobin 1010, in accordance with the present disclosure. FIG. 10A is a representation of a true continuous signal while FIG. 10B is a representation of calculations made with measurements made at discrete points along the same line.

In FIG. 10B, at location 1030, the white dot 1050 is the ratio of the intensities of the oxygenated to the de-oxygenated wavelengths and is plotted with reference to the left scale "oxygenation." In an aspect, a ratio of the intensities of the oxygenated to the de-oxygenated wavelengths can be converted into an $SpO_2$ value, indicating the percentage of oxygenated blood at a local site. At the same location 1030, the black dot 1060 is the summation of the intensities of the two wavelengths and is plotted with reference to the right scale "perfusion." The information provided by the summation 1060, which suggests fair-to-poor perfusion at location 1030, gives a different perspective than the ratio 1050, which suggests a high level of oxygenation. In practice using existing ratio methodology, a high level of oxygenation is often regarded as a sign of good perfusion, and vice versa. However, in this example, data obtained using the method of the present disclosure shows that the area of high level of oxygenation is actually poorly perfused, and the area of low level of oxygenation is actually very well perfused.

Still referring to FIG. 10B, at location 1040, the oxygenation ratio 1052 suggests that oxygenation levels are lower than optimal, while the perfusion summation 1062, which is the summation of the intensities of the two wavelengths, suggest that perfusion is good. Again, the provision of information on the total amount of both oxygenated and de-oxygenated hemoglobin gives a different perspective than the simple ratio of one to the other.

FIGS. 11A and 11B depict the detected signals of light reflected from oxygenated hemoglobin 1101 and de-oxygenated hemoglobin 1102 along a line across a wound, in accordance with the present disclosure. Points 1120, 1122, 1124, 1126, and 1128 are five locations identified along the line. In an aspect, a line across a wound may be drawn in any direction. In an aspect, any number of locations may be identified along the line for measurement, for example, up to 100 locations, such as up to 95 locations, up to 90 locations, up to 85 locations, up to 80 locations, up to 75 locations, up to 70 locations, up to 65 locations, up to 60 locations, up to 55 locations, up to 50 locations, up to 45 locations, up to 40 locations, up to 35 locations, up to 30 locations, up to 25 locations, up to 20 locations, up to 15 locations, up to 10 locations, up to 9 locations, up to 8 locations, up to 7 locations, up to 6 locations, up to 5 locations, up to 4 locations, up to 3 locations, up to 2 locations, or 1 location. In an aspect, locations identified along a line may be spaced approximately equidistance apart. In an aspect, locations identified along a line may be spaced unevenly apart. In an aspect, a subgroup of locations identified along a line may be spaced approximately equidistance apart. In an aspect, a subgroup of locations identified along a line may be unevenly spaced apart. In an aspect, multiple lines across a wound may be drawn for measurements. In an aspect, up to 100 lines may be drawn for measurements, such as up to 95 lines, up to 90 lines, up to 85 lines, up to 80 lines, up to 75 lines, up to 70 lines, up to 65 lines, up to 60 lines, up to 55 lines, up to 50 lines, up to 45 lines, up to 40 lines, up to 35 lines, up to 30 lines, up to 25 lines, up to 20 lines, up to 15 lines, up to 10 lines, up to 9 lines, up to 8 lines, up to 7 lines, up to 6 lines, up to 5 lines, up to 4 lines, up to 3 lines, up to 2 lines, or 1 line. In an aspect, lines drawn across the wound may have approximately the same angles between them. In an aspect, lines drawn across the wound may have different angles between them. In an aspect, a subgroup of lines drawn across the wound may have approximately the same angles between them. In an aspect, a subgroup of lines drawn across the wound may have different angles between them.

FIG. 11C is a plot 1100 of comparative points 1120, 1122, 1124, 1126, and 1128 of the curves 1101 and 1102 of FIGS. 11A and 11B, in accordance with the present disclosure. The white dots 1130, 1132, 1134, 1136, and 1138 connected by reference line 1131 are the oxygenation ratio (ratio of the value in curve 1101 to curve 1102 at the specified location point) and are plotted with reference to the left vertical axis "oxygenation." The black dots 1140, 1142, 1144, 1146, and 1148 connected by reference line 1141 are the summation values of curves 1101 and 1102 and are plotted with reference to the right vertical axis "perfusion."

In an aspect, in evaluating the state of a wound by inspection of the lines 1131 and 1141, a clinician could come to different assessments of the size and condition of the wound based on the shape of the lines 1131 and 1141. In this example, the perfusion information of line 1141 suggests a smaller, narrower wound, compared to line 1131. If the clinician were to proceed to attempt to remove the necrotic tissue of zone 150, with reference to FIG. 1, the clinician can remove more tissue if guided by line 1131 than if guided by line 1141. This may result in the unintended removal of some of the tissue in the zone of stasis 160, which may increase the healing and final state of the wound.

In this example, the outermost measurement point, shown as 1140 in FIG. 11D, is outside the affected area of the wound and none of the other measurements are larger than the value of measurement 1140, indicating that no measurement was taken in the zone of hyperemia. Referring to FIG. 11C, line 1150 represents the value of the largest summation value of the measurements at the two frequencies in this example, which in this example is the summation value 1140. If the line of measurement points is extended beyond the visible area of wound damage, the outermost measurement point is likely to be over healthy unaffected tissue. The measurement at a point over healthy tissue forms a baseline value to which measurements in the affected areas may be compared. Similarly, a summation value of measurements made at two frequencies at a point over healthy tissue forms a baseline summation value. As damaged tissue inherently has perfusion that varies from the normal, either increased perfusion in the zone of hyperemia or reduced perfusion in the zones of stasis or necrosis, comparison of the summation value at a point in the affected area around a wound to a summation value of healthy tissue improves the accuracy of the assessment. Comparison of two summation values taken at approximately the same time by the same person using the same equipment removes "common mode" factors that would affect all measurements such as whether the patient is active or in-active, dehydrated, or suffering from general blood loss. Comparing the affected area to a healthy are gives a better picture of the degree of damage.

A delta value 1152 exists between this largest summation value and the summation value 1142. Other delta values 1154, 1156, and 1158 exist between the largest summation value 1150 and the individual summation values 1144, 1146, and 1148.

FIG. 11E depicts an example plot 1107 of perfusion summation values taken across a different wound (not shown), in accordance with the present disclosure. Summation value 1172 has been taken over known healthy tissue. Summation value 1174 has been taken nearer to the wound and the increase in value, compared to the value of 1174, is an indication that this location is in the zone of hyperemia. The near-zero value of summation value 1176 indicates that this is likely in the zone of necrosis. The values of 1178 and 1180, being lower than 1172 while higher than 1176, indicate that these may in the zone of stasis. The shape of the curve 1182 provides guidance to a clinician as to the nature of the underlying tissue at and between the points of measurement.

If a measurement location is within the zone of hyperemia, the summation value may be higher than the summation value of healthy tissue. In this case, the "baseline" value of line 1150 in FIG. 11C may be selected as the outermost point, such as location 1140 in FIG. 11D, or from a point specifically selected as a location over healthy unaffected tissue. In an aspect, the baseline value to which other summation values are compared is the value associated with known healthy tissue, which may not the largest summation value.

In an aspect, a user may take repeated measurements to map the zone of hyperemia as indicated by the summation value, e.g. the perfusion, being higher than a baseline value taken over known healthy tissue. The locations may be captured via a manual method, e.g. marking on a drawing or picture of the wound, or via a location sensing system, e.g. using a 3D accelerometer-based location determination system. Alternately, the perfusion measurement device may incorporate a marking capability such that a user may trigger a mark to be applied to the skin. The user may do this manually. In an aspect, the perfusion measurement device may automatically apply the mark when the summation value exceeds a threshold. The threshold may be set while taking a perfusion measurement over known healthy tissue. In an aspect, the threshold may be entered directly by the user.

In the example of FIG. 11E, the baseline value would be chosen to be the value 1172 and delta values would be calculated for summation values 1174, 1176, 1178, and 1180. In an aspect, the delta values would be reported as positive values for point 1174 and negative values for points 1176, 1178, and 1180. In an aspect, the polarity of the delta values would be reversed. In one aspect, only absolute values of the delta are reported.

In an aspect, multiple measurements are taken at a chosen location at each selected wavelength. In an aspect, multiple measurements taken at a chosen location at each selected wavelength are averaged together before summation according to the present disclosure. In an aspect, each set of measurements consisting of measurements taken at a chosen location at all the selected wavelengths are first summed together, and then an average summation value is determined by averaging the sum obtained from each set of measurements.

In an aspect, a delta value is determined by subtraction of a summation value from a baseline value. In an aspect, a baseline value is selected in accordance with the method of the description provided herein. In an aspect, a baseline value is calculated by an average of summation values obtained at locations outside a wound. In an expect, a baseline value is calculated by an average of all the summation values obtained both inside and outside a wound. In an aspect, a delta value is determined by subtraction of an average summation value at a site from a baseline value. In an aspect, a delta value is determined by subtraction of the minimum summation value at a site from the baseline value. In an aspect, a delta value is determined by subtraction of the minimum summation value at a site from the maximum summation value. In an aspect, a percentage value for each summation value relative to a largest summation value in the series of summation values is further determined.

FIG. 11D depict an example wound 1105 and an exemplary map of the line of measurements of the plot of FIG. 11C, in accordance with the present disclosure system. The dots 1140, 1142, 1144, 1146, and 148 correspond to the locations 1120, 1122, 1124, 1126, and 1128 of FIGS. 11A and 11B. The zone of necrosis 1164 and the zone of hyperemia 1160 reflect the information provided by line 1141. The zone 1162 schematically illustrates a comparative zone of necrosis associated with the oxygenation line 1131, which is larger and wider than the perfusion-guided zone 1164.

FIGS. 12A, 12B, 12C, and 12D depict examples of the disclosed apparatus, in accordance with the present disclosure.

Figure 12A:
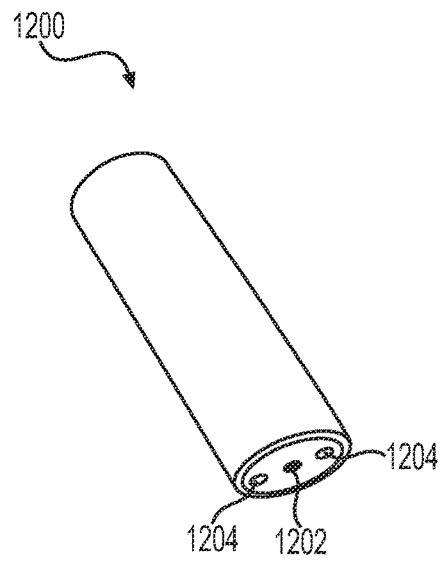
FIGS. 12A, 12B, 12C, and 12D depict examples of the disclosed apparatuses, in accordance with the present disclosure.

FIG. 12A is an example handheld device 1200 having a single emitter 1202 and two receivers 1204 disposed, in this example on opposite sides of the emitter 1202. The emitter 1202 and receivers 1204 are mounted on a rigid substrate.

Figure 12B:
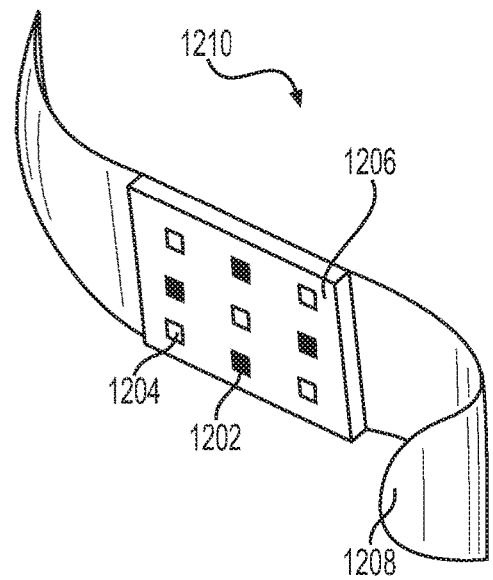

FIG. 12B depicts an example bandage 1210 wherein emitters 1202 and receivers 1204 are disposed on a flexible absorbent pad 1206 with an adhesive backing 1208 intended to retain the bandage on the skin of a patient in a fixed location. Repeated measurements of the reflected light by the receivers 1204 over time enables tracking of the condition of the wound.

Figure 12C:
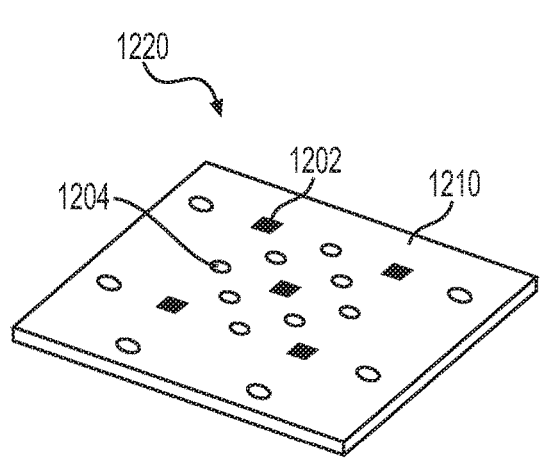

FIG. 12C depicts a substrate 1210 with an array of emitters 1202 and receivers 1204 arranged in a grid. In an aspect, a single emitter 1202 is activated while one or more of the surrounding receivers 1204 sense the reflected light. In an aspect, different emitters 1202 emit different wavelengths of light.

Figure 12D:
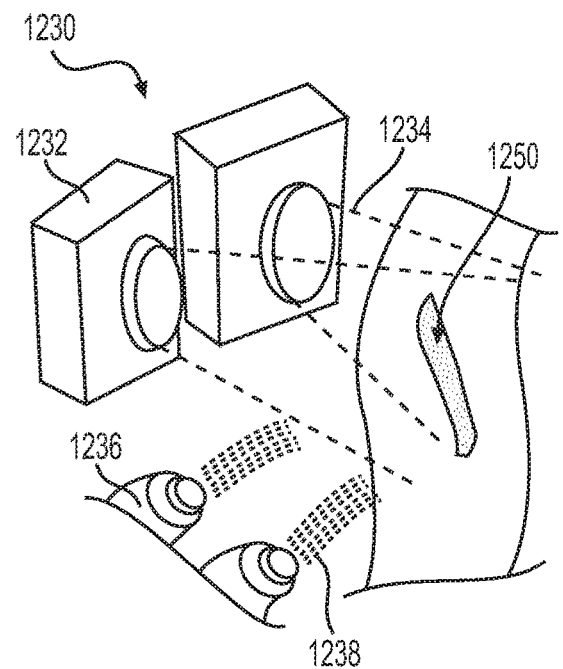

FIG. 12D depicts a system 1230 that comprises one or more emitters 1236 emitting beams 1238 of light with one or more receivers 1232 each having a field-of-view 1234. In an aspect, the receivers 1232 are image-forming cameras that optically detect the intensity of the light reaching the surface of the skin around wound 1250. In an aspect, the emitters 1236 emit different wavelengths of light. In an aspect, the emitters 1236 are activated at different and non-overlapping times and the receivers 1232 can detect the reflected light of either wavelength.

Figure 13:
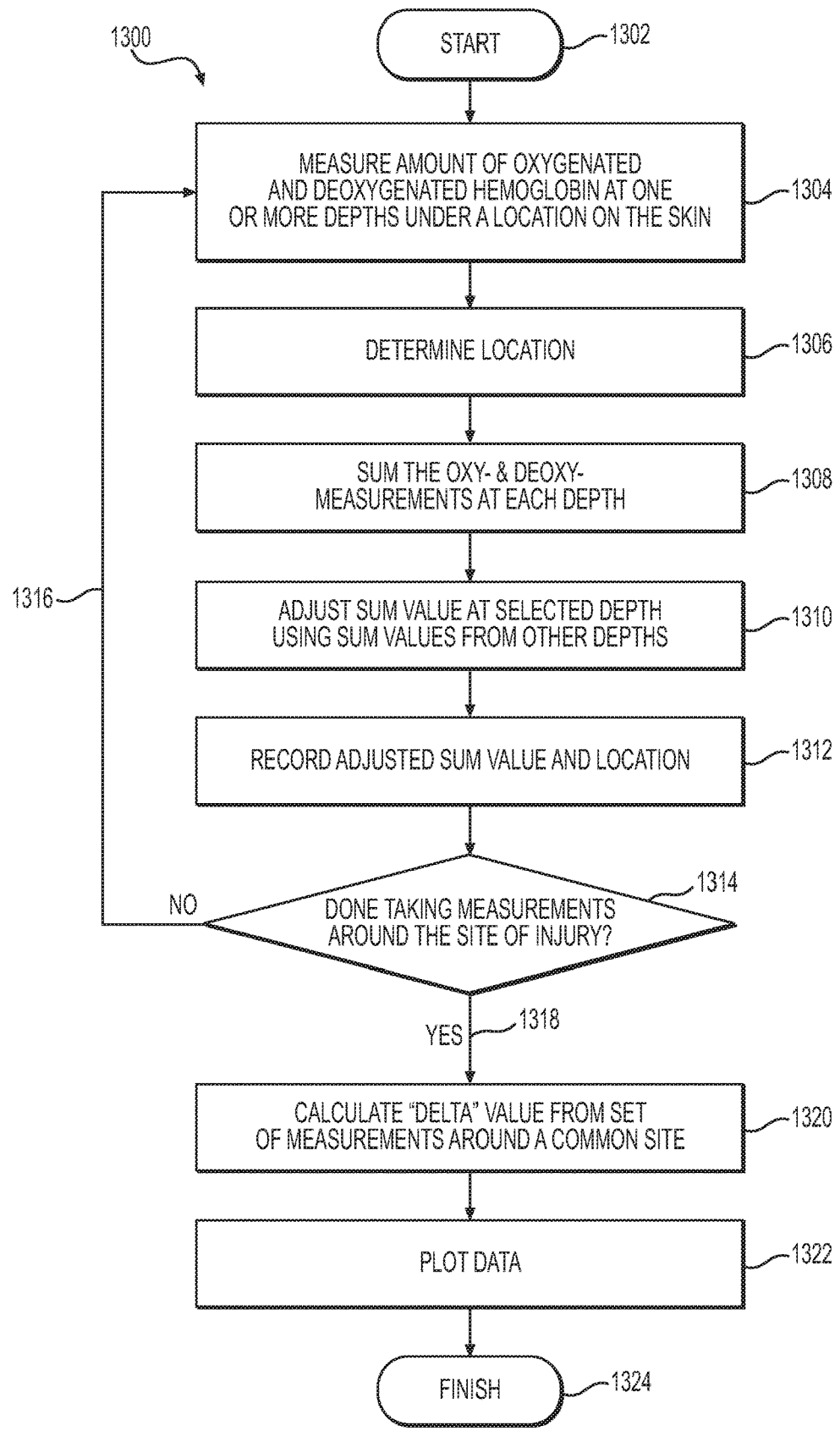
FIG. 13 is a flowchart of an exemplary method of perfusion measurement, in accordance with the present disclosure.

FIG. 13 is a flowchart 1300 of an exemplary method of perfusion measurement, in accordance with the present disclosure. The process progresses from the START step 1302 to step 1304 of measuring the amount of oxygenated and de-oxygenated hemoglobin at one or more depths below the skin. In an aspect, these measurements are derived from comparison of signals from a plurality of receivers arranged around a single emitter. In step 1306, which may precede or performed in parallel with step 1304, the location is determined. Step 1308 sums the measurements associated with oxygenated and de-oxygenated hemoglobin. Step 1310 optionally adjusts the summation value by comparison with information regarding light that reached the receivers via alternate paths through the tissue. The raw and adjusted values are recorded in step 1312. If more readings are to be taken around the site of injury, the process branches at step 1314 to the "NO" path 1316 and returns to step 1304. If all measurements are complete, the process branches at step 1314 to the "YES" path 1318 to step 1320 where a delta value is calculated as the difference between the highest perfusion value, which will be associated with healthy tissue, and the various other measurements around the common site. These delta values are plotted in step 1322 and represent a degration of perfusion as compared to the a baseline of healthy tissue for this patient at this time at this location with this instrument as operated by this user. The process terminates in step 1324 "FINISH."

Figure 14:
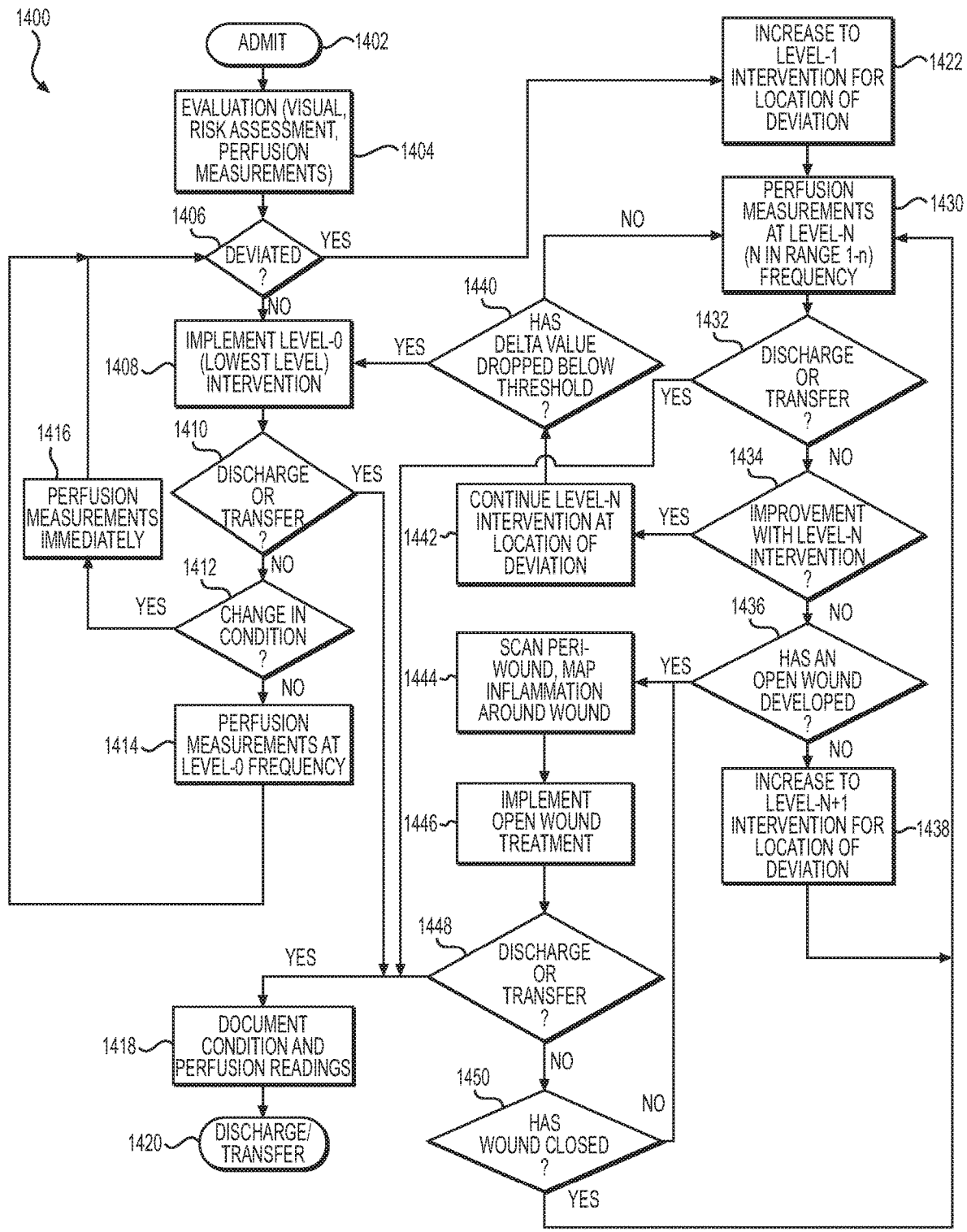
FIG. 14 depicts an example of an overall process for selecting a treatment for a wound based on perfusion measurements, where the process covers the time period from admission of a patient to a care facility until discharge of the patient from the care facility, in accordance with the present disclosure.

Selection of a Strategy for Tissue Damage Intervention Using Perfusion or Oxygenation Measurements FIG. 14 depicts an overall process 1400 for selecting a wound treatment strategy based on measured perfusion or oxygenation values of blood in tissue below a patient's skin in accordance with this disclosure, from admission to a care facility until discharge from the care facility. In an aspect, a wound is a pressure ulcer. In one aspect, a pressure ulcer is a pressure ulcer resulting from an extended period of use of a medical device such as, for example, a mask, a tubing, or a strap. In an aspect, a wound is a diabetic foot ulcer. In an aspect, a wound is a vascular ulcer. In an aspect, a wound is a burn wound. In an aspect, a care facility is selected from the group consisting of a hospital, a recovery facility, an assisted living facility, a residential care facility, a nursing home, a long-term care facility, a continuing care community, and an independent living community. In an aspect, a care facility may be a home or other residence of the patient, whereupon the "admit" step 1402 will be a first evaluation of a patient at their home by a nurse or other caregiver. In one aspect, the schedule of interventions and evaluation intervals used in a home setting may be different than the corresponding interventions and intervals used at a hospital.

In an aspect, in process 1400, a newly admitted patient receives an intake evaluation in step 1404 that includes one or more of a visual examination of a portion of the patient's skin, completion of at least a portion of a risk assessment protocol that evaluates one or more of nutrition, mobility, physical activity, physical strength, and ability to communicate, and blood perfusion measurements made in one or more locations on the patient's skin. In an aspect, the perfusion measurements may include making a plurality of perfusion measurements at a single "location" on the patient's skin. In an aspect, an $SpO_2$ value is determined from converting a ratio of the intensities of the oxygenated to the de-oxygenated wavelengths measured in the process of the prefusion measurements. In an aspect, an $SpO_2$ value In one aspect, "location" is considered as an area rather than a single point such that perfusion measurements may be made at spatially separated points within the location. For example, a "heel" location includes the medial, lateral, and posterior surfaces around the heel as well as the posterior portion of the sole of that foot.

In one aspect, once the evaluation step is complete, a determination is made in step 106 as to whether the patient's readings are abnormal, i.e., whether the combination of the results of the various elements of the evaluation indicate that the patient has, or is at risk of developing, further wound tissue damage. Each element of the evaluation may have an individual criterion for level of risk, for example a scoring system with threshold value that indicates an unacceptable risk. In an aspect, there is a protocol to combine the criteria to generate a composite parameter that can be used to select a level of intervention.

In an aspect, if the patient is determined to be at an acceptable level of risk, the process branches to step 1408 which implements the lowest level of intervention, designated herein as "level-zero" or "level-0." Progressing through steps 1410 and 1412, the patient will be reassessed using at least the perfusion or oxygenation measurement protocol in step 1414 at a frequency, or conversely a time interval, associated with level-0. The process 1400 then loops back to step 1406 to evaluate the results of the perfusion or oxygenation measurements made in step 1414.

In one aspect, if the patient is determined in step 1406 to have abnormal readings, then the process branches to step 1422, which implements a higher level of intervention. In an aspect, there is a defined hierarchy of intervention levels, with each level implementing a more intensive intervention than the next-lower level. In an aspect, each level also has a defined monitoring interval or frequency indicating how often a set of perfusion or oxygenation measurements should be made, where higher levels will generally have shorter intervals. In this example, the process has been defined by the hospital, or other administering organization, to step up one level to a level-1 intervention at this point. In another aspect, step 1422 may implement a level-2 or higher level of intervention. The process now enters a new loop starting at step 1430 where the patient will now be monitored at a level-N frequency where N is in the range of 1 to n, n being the highest defined level of intervention and monitoring.

In an aspect, at step 1434, the patient's history is evaluated to determine whether their condition is improving. If the patient's condition is improving, for example as evidenced by a decreasing delta value for perfusion measurements, then the process branches to step 1442. In this example, step 1442 continues to implement the current level of intervention and the process loops through step 1440 to steps 1430-1432-1434-1442-1440 until the delta value drops below the threshold. In an aspect, the level of intervention may be reduced in step 1442 based on the magnitude of the delta value as the delta value trends downward. In an aspect, the patient's condition is improving if oxygenation measurements are consistently at or above 95% oxygenated.

In one aspect, if the patient does not show improvement in step 1434, the process branches to an increase in the level of intervention in step 1438 provided that the skin is not broken, i.e., an open wound has not developed, in step 1436. If an open wound has developed, perfusion measurements will now be made around the periphery of the open wound in step 1444 to map inflammation or other precursor indication of the wound enlarging. The open wound itself is treated in step 1448 and this secondary loop 1444-1446-1448-1450 continues until the wound closes, whereupon the process returns to step 1430.

In an aspect, at any time in process 100, discharge of the patient branches to step 1418, where the condition of the patient upon discharge or transfer is documented. In an aspect, step 1418 comprises a final set of perfusion measurements at one or more locations on the patient's body. In one aspect, a final set of oxygenation measurements at one or more locations on the patient's body is made. In an aspect, these locations include areas that were not receiving an intervention and were not previously identified as at risk. In an aspect, this information is provided to the receiving caregiver. The patient is then discharged or transferred in step 120.

In an aspect, the present disclosure provides for, and includes, a method of identifying and treating a patient in need of wound intervention, the method comprising the steps of: evaluating a patient for a risk of tissue damage upon admission to a care facility, where the evaluating step comprises making a first plurality of perfusion measurements in the patient, calculating a first delta value from a portion of the first plurality of perfusion measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater.

In an aspect, the present disclosure provides for, and includes, a method of identifying and treating a patient in need of wound intervention, the method comprising the steps of: evaluating a patient for a risk of tissue damage upon admission to a care facility, where the evaluating step comprises making a first plurality of $SpO_2$ measurements in the patient, determining whether any of the first plurality of $SpO_2$ measurements is below a first threshold, administering a first intervention of level-0 if the first plurality of $SpO_2$ measurements are at or above the first threshold, and administering a first intervention of level-N if any of the first plurality of $SpO_2$ measurements is below the first threshold, where N is an integer and N has a value of 1 or greater. In an aspect, a first threshold for $SpO_2$ measurements is about 95%. In one aspect, a first threshold $SpO_2$ measurements is about 95.5%, about 96%, about 96.5%, about 97%, about 97.5%, or about 98%.

In one aspect, a first plurality of perfusion measurements is taken at and around one or more anatomical sites selected from the group consisting of a sternum, a sacrum, a heel, a scapula, an elbow, an ear, and other fleshy tissues of a patient. In an aspect, a first plurality of perfusion measurements is taken at and around one or more anatomical sites at risk of tissue injury. In an aspect, a first plurality of perfusion measurements is taken at and around all anatomical sites at risk of tissue injury. FIGS. 29A, 29B, 29C, and 29D illustrate locations of tissue injury risk in circles for patients in different positions. In an aspect, a first plurality of perfusion measurements is taken at and around one or more anatomical sites in long-term contact with a medical device, an anatomical site is selected from the group consisting of a cheek, a nose, a chest, a stomach, and a lower abdomen area. In an aspect, a first plurality of perfusion measurements is separated into sub-groups for analysis based on the general location at which a measurement is taken. In one aspect, a first plurality of perfusion measurements is taken at locations located on one or more concentric circles centered around an anatomical site. In an aspect, a first plurality of perfusion measurements is taken at locations located on a straight line at approximately equidistant from an anatomical site.

In one aspect, a first delta value is determined by the difference between the maximum perfusion value and the minimum perfusion value from the first plurality of perfusion measurements collected. In an aspect, a first delta value is determined by the difference between the maximum perfusion average of measurements taken at one location and the minimum perfusion average of measurements taken at a second location. In one aspect, a first delta value is determined for a portion of a first plurality of perfusion measurements made up of a sub-group as defined by location taken. In an aspect, an average perfusion value at a location is obtained from two, three, four, five, six, seven, eight, nine, ten, or more than ten perfusion values measured at that location. In one aspect, a first delta value is determined by the difference between perfusion values derived from measurements taken at two bisymmetric locations with respect to a centerline.

In an aspect, a delta value may be calculated from a plurality of perfusion measurements made at a certain location, or in close proximity around a specific location, in a plurality of methods. In an aspect, a plurality of perfusion measurements are made in a pre-determined pattern on the skin and the delta value is calculated by subtracting the perfusion value associated with a pre-determined position within the pattern from the largest perfusion value made at the other positions in the pattern. In an aspect, a plurality of perfusion measurements are made in a pre-determined pattern on the skin and the delta value is calculated by identifying the perfusion value associated with a pre-determined position within the pattern and subtracting the largest perfusion value made at the other positions in the pattern. In an aspect, an average perfusion value may be calculated from a portion of a set of perfusion values generated by a plurality of perfusion measurements at a single location and a delta value calculated as the largest difference between the average and a single perfusion value of the same set. In an aspect, a delta value may be calculated as a ratio of the largest perfusion value to the smallest perfusion value within a set of perfusion values.

In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein. It will be understood that a threshold is not limited by design, but rather, one of ordinary skill in the art would be capable of choosing a predetermined value based on a given unit of perfusion. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, N ranges from 1 to 50, such as from 1 to 2, from 1 to 3, from 1 to 4, from 1 to 5, from 1 to 6, from 1 to 7, from 1 to 8, from 1 to 9, from 1 to 10, from 1 to 15, from 1 to 20, from 1 to 25, from 1 to 30, from 1 to 35, from 1 to 40, or from 1 to 45.

In one aspect, N is determined by the amount by which the first delta value exceeds the first threshold. In an aspect, the amount by which a delta value exceeds a threshold established for (N+1) is greater than the amount by which a delta value exceeds a threshold established for N. In one aspect, the amount by which a delta value exceeds a threshold established for (N−1) is less than the amount by which a delta value exceeds a threshold established for N.

In an aspect, a level-1 (N=1) intervention is applied to a patient having a delta value exceeding the threshold by not more than 100% of the threshold value, such as not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-1 intervention is applied to a location at which a measurement was made.

In an aspect, a level-2 (N=2) intervention is applied to a patient having a delta value exceeding the threshold by not more than 150% of the threshold value, such as not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-2 intervention is applied to a location at which a measurement was made.

In one aspect, a level-3 (N=3) intervention is applied to a patient having a delta value exceeding the threshold by not more than 200% of the threshold value, such as not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-3 intervention is applied to a location at which a measurement was made.

In one aspect, a level-4 (N=4) intervention is applied to a patient having a delta value exceeding the threshold by not more than 250% of the threshold value, such as not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-4 intervention is applied to a location at which a measurement was made.

In one aspect, a level-5 (N=5) intervention is applied to a patient having a delta value exceeding the threshold by not more than 300% of the threshold value, such as not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-5 intervention is applied to a location at which a measurement was made.

In one aspect, a level-6 (N=6) intervention is applied to a patient having a delta value exceeding the threshold by not more than 350% of the threshold value, such as not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-6 intervention is applied to a location at which a measurement was made.

In one aspect, a level-7 (N=7) intervention is applied to a patient having a delta value exceeding the threshold by not more than 400% of the threshold value, such as not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-7 intervention is applied to a location at which a measurement was made.

In one aspect, a level-8 (N=8) intervention is applied to a patient having a delta value exceeding the threshold by not more than 450% of the threshold value, such as not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-8 intervention is applied to a location at which a measurement was made.

In one aspect, a level-9 (N=9) intervention is applied to a patient having a delta value exceeding the threshold by not more than 500% of the threshold value, such as not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-9 intervention is applied to a location at which a measurement was made.

In one aspect, a level-10 (N=10) intervention is applied to a patient having a delta value exceeding the threshold by not more than 550% of the threshold value, such as not more than 545%, not more than 540%, not more than 535%, not more than 530%, not more than 525%, not more than 520%, not more than 515%, not more than 510%, not more than 505%, not more than 500%, not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-10 intervention is applied to a location at which a measurement was made.

In one aspect, a level-N intervention is more intensive than a level-0 intervention. In an aspect, a level-(N+1) intervention is more intensive than a level-N intervention. In one aspect, a level-(N−1) intervention is less intensive than a level-N intervention.

In an aspect, the evaluating step of the present disclosure further comprises performing a visual assessment. In one aspect, the visual assessment is performed in accordance with the guidelines of the National Pressure Ulcer Advisory Panel (NPUAP).

In one aspect, the evaluating step of the present disclosure further comprises performing a risk assessment. In an aspect, the risk assessment is performed in accordance with a test selected from the group consisting of the Braden Scale, the Gosnell Scale, the Norton Scale, and the Waterlow Scale.

In an aspect, the evaluating step of the present disclosure further comprises performing an assessment using one or more objective measurements selected from the group consisting of: sub-epidermal moisture, bioimpedance, ultrasound, pressure measurement; capillary pressure, thermal imaging, spectral imaging, transcutaneous water loss, and detection of interleukin-1 alpha presence at one or more anatomic site of interest.

In an aspect, the present disclosure further provides for, and includes, making a second plurality of perfusion measurements in the patient at a first pre-determined frequency corresponding to the administered intervention level, calculating a second delta value from a portion of the second plurality of perfusion measurements, determining whether the second delta value exceeds a second threshold, continuing to administer the first intervention if the second delta value does not exceed the second threshold, continuing to make a plurality of perfusion measurements at the first pre-determined frequency if the second delta value does not exceed the second threshold, administering a second intervention of level-M if the second delta value exceeds the second threshold, where M is an integer and M is greater than N, and making a plurality of perfusion measurements at a second pre-determined frequency corresponding to level-M if the second delta value exceeds the second threshold.

In an aspect, the present disclosure further provides for, and includes, making a second plurality of $SpO_2$ measurements in the patient at a first pre-determined frequency corresponding to the administered intervention level, calculating a time delta value based on the differences between the first plurality and the second plurality of $SpO_2$ measurements, determining whether the time delta value is a decrease exceeding a second threshold, continuing to administer the first intervention if the time delta value does not exceed the second threshold, continuing to make a plurality of perfusion measurements at the first pre-determined frequency if the time delta value does not exceed the second threshold, administering a second intervention of level-M if the time delta value is a decrease exceeding the second threshold, where M is an integer and M is greater than N, and making a plurality of $SpO_2$ measurements at a second pre-determined frequency corresponding to level-M if the time delta value is a decrease exceeding the second threshold.

In one aspect, a pre-determined frequency is selected from the group consisting of at least once every 72 hours, at least once every 48 hours, at least once every 24 hours, at least once every 12 hours, at least once every 8 hours, at least once every 6 hours, at least once every 4 hours, at least once every 3 hours, at least once every 2 hours, at least once every hour, and at least once every half an hour.

In one aspect, a second plurality of perfusion measurements are taken in accordance with the description provided herein. In an aspect, a second plurality of perfusion measurements are made at the same locations where a first plurality of perfusion measurements were taken. In one aspect, a second plurality of perfusion measurements are made at some of the same locations where a first plurality of perfusion measurements were taken. In an aspect, a second plurality of perfusion measurements are made near the locations where a first plurality of perfusion measurements were taken. In one aspect, a second plurality of perfusion measurements are made at different locations than where a first plurality of perfusion measurements were taken.

In an aspect, a second delta value is determined by the difference between the maximum perfusion value and the minimum perfusion value from the second plurality of perfusion measurements collected. In one aspect, a second delta value is determined by the difference between the maximum average of perfusion measurements taken at one location and the minimum average of perfusion measurements taken at a second location. In one aspect, a second delta value is determined for a portion of a second plurality of perfusion measurements made up of a sub-group as defined by location taken.

In an aspect, a second threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a second threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In one aspect, a second threshold for $SpO_2$ measurements may be about 3%, 3.5%, 4%, 5%, 5.5%, 6%, 6.6%, or 7%. In an aspect, a second threshold can be scaled by a factor or a multiple based on the values provided herein. In one aspect, a second threshold can be the same as a first threshold. In an aspect, a second threshold can be greater than a first threshold. In one aspect, a second threshold can be less than a first threshold.

In an aspect, M ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In one aspect, M is determined by the amount by which the second delta value exceeds the second threshold. In an aspect, the amount by which a delta value exceeds a threshold established for (M+1) is greater than the amount by which a delta value exceeds a threshold established for M. In one aspect, the amount by which a delta value exceeds a threshold established for (M−1) is less than the amount by which a delta value exceeds a threshold established for M.

In an aspect, a level M intervention is chosen in accordance with the description provided herein, replacing N with M.

In one aspect, the present disclosure further provides for, and includes, determining whether the second delta value is less than a third threshold, administering a level-(N−1) intervention if the second delta value is less than the third threshold and if the first intervention is not of level-0, and making a plurality of perfusion measurements at a pre-determined frequency corresponding to level-(N−1) if the second delta value is less than the third threshold.

In an aspect, the present disclosure further provides for, and includes, determining whether the time delta value is an increase exceeding a third threshold, administering a level-(N−1) intervention if the time delta value is an increase exceeding the third threshold and if the first intervention is not of level-0, and making a plurality of $SpO_2$ measurements at a pre-determined frequency corresponding to level-(N−1) if the time delta value is an increase exceeding the third threshold.

In an aspect, a third threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a third threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In one aspect, a second threshold for $SpO_2$ measurements may be about 3%, 3.5%, 4%, 5%, 5.5%, 6%, 6.6%, or 7%. In an aspect, a third threshold can be scaled by a factor or a multiple based on the values provided herein. In one aspect, a third threshold can be the same as a second threshold. In an aspect, a third threshold can be greater than a second threshold. In one aspect, a third threshold can be less than a second threshold. In one aspect, a third threshold can be the same as a first threshold. In an aspect, a third threshold can be greater than a first threshold. In one aspect, a third threshold can be less than a first threshold.

In an aspect, a second delta value can be 0.1-99.5% of the third threshold, such as 0.1-1%, 0.1-5%, 1-5%, 5-15%, 10-20%, 15-25%, 20-30%, 25-35%, 30-40%, 35-45%, 40-50%, 0.1-25%, 15-35%, 25-50%, 25-75%, 45-55%, 50-60%, 55-65%, 60-70%, 65-75%, 40-55%, 50-75%, 50-99.5%, 70-80%, 75%-85%, 80-90%, 85-95%, 90-99.5%, 65-85%, or 75-99.5% of the third threshold.

In one aspect, the present disclosure provides for, and includes, a method of slowing the progression of skin and tissue damage in a patient in need thereof, the method comprising the steps of: identifying a current intervention of level-K received by the patient, making a plurality of perfusion measurements in the patient, calculating a delta value from a portion of the plurality of perfusion measurements, determining whether the delta value exceeds a first threshold, continuing to administer the current intervention if the delta value does not exceed the first threshold, continuing to make a plurality of perfusion measurements at a pre-determined frequency corresponding to level-K if the delta value does not exceed the first threshold, administering a new intervention of level-N if the delta value exceeds the first threshold, where N has a value greater than K, and making a plurality of perfusion measurements at a pre-determined frequency corresponding to level-N if the delta value exceeds the first threshold. In an aspect, a patient in need thereof is a patient experiencing a change of care, a change in mobility, a change in nutrition, a change in sensory perception, or a combination thereof. In one aspect, a patient in need thereof is a patient having developed an open wound. In an aspect, a patient in need thereof is a patient having recovered from an open wound. In one aspect, a patient in need thereof is a patient receiving surgery. In an aspect, a patient in need thereof is a patient recovering from surgery. In an aspect, a patient in need thereof is a patient receiving spinal analgesics or sacral analgesics during a surgery. In one aspect, a patient in need thereof is a patient receiving a surgery for a duration of four or more hours, such as five or more hours, six or more hours, seven or more hours, eight or more hours, nine or more hours, ten or more hours, eleven or more hours, or twelve or more hours. In an aspect, a surgery has a duration of one or more hours, such as two or more hours, or three or more hours.

In one aspect, a plurality of perfusion measurements are taken in accordance with the description provided herein. In an aspect, a delta value is determined in accordance with the description provided herein. In one aspect, a first threshold is determined in accordance with the description provided herein.

In an aspect, K ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In an aspect, K is determined by the amount by which the delta value exceeds the threshold. In an aspect, the amount by which a delta value exceeds a threshold established for (K+1) is greater than the amount by which a delta value exceeds a threshold established for K. In one aspect, the amount by which a delta value exceeds a threshold established for (K−1) is less than the amount by which a delta value exceeds a threshold established for K.

In an aspect, a level K intervention is chosen in accordance with the description provided herein, replacing N with K.

In an aspect, the present disclosure further provides for, and includes, determining whether the delta value is less than a second threshold, administering a level-L intervention if the delta value is less than the second threshold, where L has a non-negative value less than K, and making a plurality of perfusion measurements at a pre-determined frequency corresponding to level-L if the delta value is less than the second threshold.

In an aspect, a second threshold is determined in accordance with the description provided herein.

In one aspect, the present disclosure provides for, and includes, determining whether any of the plurality of $SpO_2$ measurements is above the threshold range corresponding to level-K, administering a level-L intervention if any of the plurality of $SpO_2$ measurements is above the threshold range corresponding to level-K, where L has a non-negative value less than K, and making a plurality of perfusion measurements at a pre-determined frequency corresponding to level-L if any of the plurality of $SpO_2$ measurements is above the threshold range corresponding to level-K. In an aspect, a threshold range is selected from the group consisting of below about 85%, between about 85% to about 95%, and above or equal to 95%.

In an aspect, L can be K−1, K−2, K−3, K−4, K−5, K−6, K−7, K−8, K−9, or K−10. In one aspect, L is K−1 if a delta value is 90-99.5% of the second threshold, such as 90-95%, 91-96%, 92-97%, 93-98%, 94-99%, or 95-99.5% of the second threshold, unless K−1 is less than 0, in which case L would be 0. In an aspect, L is K−2 if a delta value is 80-89.9% of the second threshold, such as 80-85%, 81-86%, 82-87%, 83-88%, 84-89%, or 85-89.9% of the second threshold, unless K−2 is less than 0, in which case L would be 0. In one aspect, L is K−3 if a delta value is 70-79.9% of the second threshold, such as 70-75%, 71-76%, 72-77%, 73-78%, 74-79%, or 75-79.9% of the second threshold, unless K−3 is less than 0, in which case L would be 0. In an aspect, L is K−4 if a delta value is 60-69.9% of the second threshold, such as 60-65%, 61-66%, 62-67%, 63-68%, 64-69%, or 65-69.9% of the second threshold, unless K−4 is less than 0, in which case L would be 0. In one aspect, L is K−5 if a delta value is 50-59.9% of the second threshold, such as 50-55%, 51-56%, 52-57%, 53-58%, 54-59%, or 55-59.9% of the second threshold, unless K−5 is less than 0, in which case L would be 0. In an aspect, L is K−6 if a delta value is 40-49.9% of the second threshold, such as 40-45%, 41-46%, 42-47%, 43-48%, 44-49%, or 45-49.9% of the second threshold, unless K−6 is less than 0, in which case L would be 0. In one aspect, L is K−7 if a delta value is 30-39.9% of the second threshold, such as 30-35%, 31-36%, 32-37%, 33-38%, 34-39%, or 35-39.9% of the second threshold, unless K−7 is less than 0, in which case L would be 0. In an aspect, L is K−8 if a delta value is 20-29.9% of the second threshold, such as 20-25%, 21-26%, 22-27%, 23-28%, 24-29%, or 25-29.9% of the second threshold, unless K−8 is less than 0, in which case L would be 0. In one aspect, L is K−9 if a delta value is 10-19.9% of the second threshold, such as 10-15%, 11-16%, 12-17%, 13-18%, 14-19%, or 15-19.9% of the second threshold, unless K−9 is less than 0, in which case L would be 0. In an aspect, L is K−10 if a delta value is 0.1-9.9% of the second threshold, such as 0.1-5%, 1-6%, 2-7%, 3-8%, 4-9%, or 5-9.9% of the second threshold, unless K−10 is less than 0, in which case L would be 0.

In an aspect, the present disclosure provides for, and includes, a method of stratifying groups of patients in a care facility based on risk of tissue damage, the method comprising the steps of: making a plurality of perfusion measurements in each of the patients, calculating a delta value from a portion of the plurality of perfusion measurements for each of the patients, determining whether each delta value exceeds any values in a set of threshold values corresponding to N care levels and assigning a care level to each of the patients, rearranging the group of patients based on each of the patient's assigned care levels.

In an aspect, the present disclosure provides for, and includes, a method of stratifying groups of patients in a care facility based on the risk of wound development, the method comprising the steps of: making a plurality of $SpO_2$ measurements in each of the patients, determining whether each of the plurality of $SpO_2$ measurements is below any values in a set of threshold values corresponding to N care levels and assigning a care level to each of the patients, and rearranging the group of patients based on each of the patient's assigned care levels.

In one aspect, the present disclosure provides for, and includes, a method of reducing incidence of tissue damage in patients admitted to a care facility, the method comprising the steps of: evaluating a patient for a risk of tissue damage upon admission to the care facility, where the evaluating step comprises making a first plurality of perfusion measurements in the patient, calculating a first delta value from a portion of the first plurality of perfusion measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater. In an aspect, the present disclosure provides for, and includes, a method of reducing the incidence of wound development in patients admitted to a care facility, the method comprising the steps of: evaluating a patient for a risk of tissue damage upon admission to the care facility, where the evaluating step comprises making a first plurality of $SpO_2$ measurements in the patient, determining whether any of the first plurality of SpO$_2$ measurements is below a first threshold, administering a first intervention of level-0 if the first plurality of SpO$_2$ measurements are above or equal to the first threshold, and administering an intervention of level-N if any of the first plurality of SpO$_2$ measurements is below a first threshold, where N is an integer and N has a value of 1 or greater. In an aspect, the incidence of ulcers in patients in the care facility is reduced to less than 1 in 100, less than 1 in 200, less than 1 in 300, less than 1 in 400, less than 1 in 500, less than 1 in 600, less than 1 in 700, less than 1 in 800, less than 1 in 900, or less than 1 in 1000.

In an aspect, the present disclosure provides for, and includes, a method of identifying and treating a patient in need of application of a barrier cream to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a barrier cream to the patient's heel if the delta value exceeds the threshold, and making a plurality of perfusion measurements every two hours if the delta value exceeds the threshold. In an aspect, a plurality of perfusion measurements are made at least once every hour or at least once every half an hour if the delta value exceeds the threshold.

In an aspect, the present disclosure provides for, and includes, a method of identifying and treating a patient in need of application of a barrier cream to the patient's heel, the method comprising the steps of: making a plurality of SpO$_2$ measurements at the patient's heel, determining whether any of the plurality of SpO$_2$ measurements is below a threshold corresponding to level N, where N is greater than or equal to 2, administering a barrier cream to the patient's heel if any of the plurality of SpO$_2$ measurements is below the threshold, and making a plurality of SpO$_2$ measurements every two hours if any of the plurality of SpO$_2$ measurements is below the threshold.

In one aspect, the present disclosure provides for, and includes, a method of identifying and treating a patient in need of application of a neuro-muscular stimulation to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a neuro-muscular stimulation to the patient's heel if the delta value exceeds the threshold, and making a plurality of perfusion measurements every hour if the delta value exceeds the threshold. In an aspect, a plurality of perfusion measurements are made at least once every half an hour if the delta value exceeds the threshold.

In an aspect, the present disclosure provides for, and includes, a method of identifying and treating a patient in need of application of a neuro-muscular stimulation to the patient's heel, the method comprising the steps of: making a plurality of SpO$_2$ measurements at the patient's heel, determining whether any of the plurality of SpO$_2$ measurements is below a threshold corresponding to level N, where N is greater than or equal to 2, administering a neuro-muscular stimulation to the patient's heel if any of the plurality of SpO$_2$ measurements is below the threshold, and making a plurality of SpO$_2$ measurements every hour if any of the plurality of SpO$_2$ measurements is below the threshold.

In an aspect, the present disclosure provides for, and includes, a method of identifying and treating a patient in need of application of a topical cream to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a topical cream to the patient's heel if the delta value exceeds the threshold, and making a plurality of perfusion measurements every half an hour if the delta value exceeds the threshold.

In an aspect, the present disclosure provides for, and includes, a method of identifying and treating a patient in need of application of a topical cream to the patient's heel, the method comprising the steps of: making a plurality of SpO$_2$ measurements at the patient's heel, determining whether any of the plurality of SpO$_2$ measurements is below a threshold corresponding to level N, where N is greater than or equal to 2, administering a topical cream to the patient's heel if any of the plurality of SpO$_2$ measurements is below the threshold, and making a plurality of SpO$_2$ measurements every half an hour if any of the plurality of SpO$_2$ measurements is below the threshold.

In an aspect, the present disclosure provides for, and includes, a method of identifying and treating a patient in need of application of a heel boot to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a heel boot to the patient's heel if the delta value exceeds the threshold, and making a plurality of perfusion measurements every half an hour if the delta value exceeds the threshold.

In an aspect, the present disclosure provides for, and includes, a method of identifying and treating a patient in need of application of a heel boot to the patient's heel, the method comprising the steps of: making a plurality of SpO$_2$ measurements at the patient's heel, determining whether any of the plurality of SpO$_2$ measurements is below a threshold corresponding to level N, where N is greater than or equal to 2, administering a heel boot to the patient's heel if any of the plurality of SpO$_2$ measurements is below the threshold, and making a plurality of SpO$_2$ measurements every half an hour if any of the plurality of SpO$_2$ measurements is below the threshold.

In one aspect, the present disclosure provides for, and includes, a method of identifying and treating a patient in need of application of a barrier cream to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a barrier cream to the patient's sacrum if the delta value exceeds the threshold, and making a plurality of perfusion measurements every six hours if the delta value exceeds the threshold. In an aspect, a plurality of perfusion measurements are made at least once every four hours, at least once every three hours, at least once every two hours, at least once an hour, or at least once every half an hour if the delta value exceeds the threshold.

In an aspect, the present disclosure provides for, and includes, a method of identifying and treating a patient in need of application of a barrier cream to the patient's sacrum, the method comprising the steps of: making a plurality of SpO$_2$ measurements at the patient's sacrum, determining whether any of the plurality of SpO$_2$ measurements is below a threshold corresponding to level N, where N is greater than or equal to 2, administering a barrier cream to the patient's sacrum if any of the plurality of SpO$_2$ measurements is below the threshold, and making a plurality of SpO$_2$ measurements every six hours if any of the plurality of SpO$_2$ measurements is below the threshold.

In an aspect, the present disclosure provides for, and includes, a method of identifying and treating a patient in need of application of a neuro-muscular stimulation to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a neuro-muscular stimulation to the patient's sacrum if the delta value exceeds the threshold, and making a plurality of perfusion measurements every four hours if the delta value exceeds the threshold. In an aspect, a plurality of perfusion measurements are made at least once every three hours, at least once every two hours, at least once an hour, or at least once every half an hour if the delta value exceeds the threshold.

In an aspect, the present disclosure provides for, and includes, a method of identifying and treating a patient in need of application of a neuro-muscular stimulation to the patient's sacrum, the method comprising the steps of: making a plurality of SpO$_2$ measurements at the patient's sacrum, determining whether any of the plurality of SpO$_2$ measurements is below a threshold corresponding to level N, where N is greater than or equal to 2, administering a neuro-muscular stimulation to the patient's sacrum if any of the plurality of SpO$_2$ measurements is below the threshold, and making a plurality of SpO$_2$ measurements every four hours if any of the plurality of SpO$_2$ measurements is below the threshold.

In one aspect, the present disclosure provides for, and includes, a method of identifying and treating a patient in need of application of a topical cream to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a topical cream to the patient's sacrum if the delta value exceeds the threshold, and making a plurality of perfusion measurements every two hours if the delta value exceeds the threshold. In an aspect, a plurality of perfusion measurements are made at least once an hour or at least once every half an hour if the delta value exceeds the threshold.

In an aspect, the present disclosure provides for, and includes, a method of identifying and treating a patient in need of application of a topical cream to the patient's sacrum, the method comprising the steps of: making a plurality of SpO$_2$ measurements at the patient's sacrum, determining whether any of the plurality of SpO$_2$ measurements is below a threshold corresponding to level N, where N is greater than or equal to 2, administering a topical cream to the patient's sacrum if any of the plurality of SpO$_2$ measurements is below the threshold, and making a plurality of SpO$_2$ measurements every two hours if any of the plurality of SpO$_2$ measurements is below the threshold.

In one aspect, the present disclosure provides for, and includes, a method of identifying and treating a patient in need of application of therapeutic ultrasound, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering therapeutic ultrasound to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of therapeutic ultrasound, the method comprising the steps of: making a plurality of SpO$_2$ measurements at an anatomic site of the patient, determining whether any of the plurality of SpO$_2$ measurements is below a threshold corresponding to level N, where N is greater than or equal to 2, administering therapeutic ultrasound to the anatomic site if any of the plurality of SpO$_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of application of shockwave therapy, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering shockwave therapy to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient. In one aspect, shockwave therapy is provided via electromagnetic pulse or pressurized air.

In an aspect, the present disclosure provides for, and includes, a method of identifying and treating a patient in need of application of shockwave therapy, the method comprising the steps of: making a plurality of SpO$_2$ measurements at an anatomic site of the patient, determining whether any of the plurality of SpO$_2$ measurements is below a threshold corresponding to level N, where N is greater than or equal to 2, administering shockwave therapy to the anatomic site if any of the plurality of SpO$_2$ measurements is below the threshold. In an aspect, an anatomical site is selected from the group consisting of a sternum, a sacrum, a heel, a scapula, an elbow, an ear, and other fleshy tissues over a bony prominence of a patient. In one aspect, shockwave therapy is provided via electromagnetic pulse or pressurized air.

In one aspect, the present disclosure provides for, and includes, a method of identifying and treating a patient in need of application of a 30-degree wedge, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering a 30-degree wedge to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a 30-degree wedge, the method comprising the steps of: making a plurality of $SpO_2$ measurements at an anatomic site of the patient, determining whether any of the plurality of $SpO_2$ measurements is below a threshold corresponding to level N, where N is greater than or equal to 2, administering a 30-degree wedge to the anatomic site if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of application of a composite dressing, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, administering a composite dressing to the anatomic site if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a composite dressing, the method comprising the steps of: making a plurality of $SpO_2$ measurements at an anatomic site of the patient, determining whether any of the plurality of $SpO_2$ measurements is below a threshold corresponding to level N, where N is greater than or equal to 2, administering a composite dressing to the anatomic site if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of a hybrid mattress, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, providing a hybrid mattress to support the patient if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a hybrid mattress, the method comprising the steps of: making a plurality of $SpO_2$ measurements at an anatomic site of the patient, determining whether any of the plurality of $SpO_2$ measurements is below a threshold corresponding to level N, where N is greater than or equal to 2, providing a hybrid mattress to support the patient if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In one aspect, the present disclosure provides for, and includes, a method of identifying and treating a patient in need of a dynamic mattress, the method comprising the steps of: making a plurality of perfusion measurements at an anatomic site of the patient, calculating a delta value from a portion of the plurality of perfusion measurements, determining whether the delta value exceeds a threshold corresponding to level N, where N is greater than or equal to 2, providing a dynamic mattress to support the patient if the delta value exceeds the threshold, and making a plurality of perfusion measurements every two hours if the delta value exceeds the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and treating a patient in need of application of a dynamic mattress, the method comprising the steps of: making a plurality of $SpO_2$ measurements at an anatomic site of the patient, determining whether any of the plurality of $SpO_2$ measurements is below a threshold corresponding to level N, where N is greater than or equal to 2, providing a dynamic mattress to support the patient if any of the plurality of $SpO_2$ measurements is below the threshold. In an aspect, an anatomical site is selected from the group consisting of a sternum, a sacrum, a heel, a scapula, an elbow, an ear, and other fleshy tissues over a bony prominence of a patient.

In an aspect, the present disclosure provides for, and includes, a method of identifying and moving a bedridden patient in need thereof, the method comprising the steps of: providing a mobility sensor comprising an accelerometer and a gyro sensor; monitor frequency and range of mobilization of the patient; providing an alert when the mobility sensor does not sense a movement more than a quarter turn for a specified period of time; and moving the patient upon the alert.

In an aspect, the present disclosure further provides for, and includes, providing targeted treatment to an anatomical location of a patient identified as being damaged by a combination of a visual assessment and perfusion measurements. In one aspect, a targeted treatment is provided to a common site for wound development selected from the group consisting of: toes, heels, a sacrum, a spine, elbows, shoulder blades, occiput, and ischial tuberosity. In an aspect, a targeted treatment is concurrently provided to a second common site for wound development selected from the group consisting of: toes, heels, a sacrum, a spine, elbows, shoulder blades, occiput, and ischial tuberosity. In one aspect, a first site receiving a targeted treatment is known to cause a development of a wound at a second site.

Comparison of Bisymmetric Perfusion Measurements to Identify Damaged Tissue

Figure 22A:
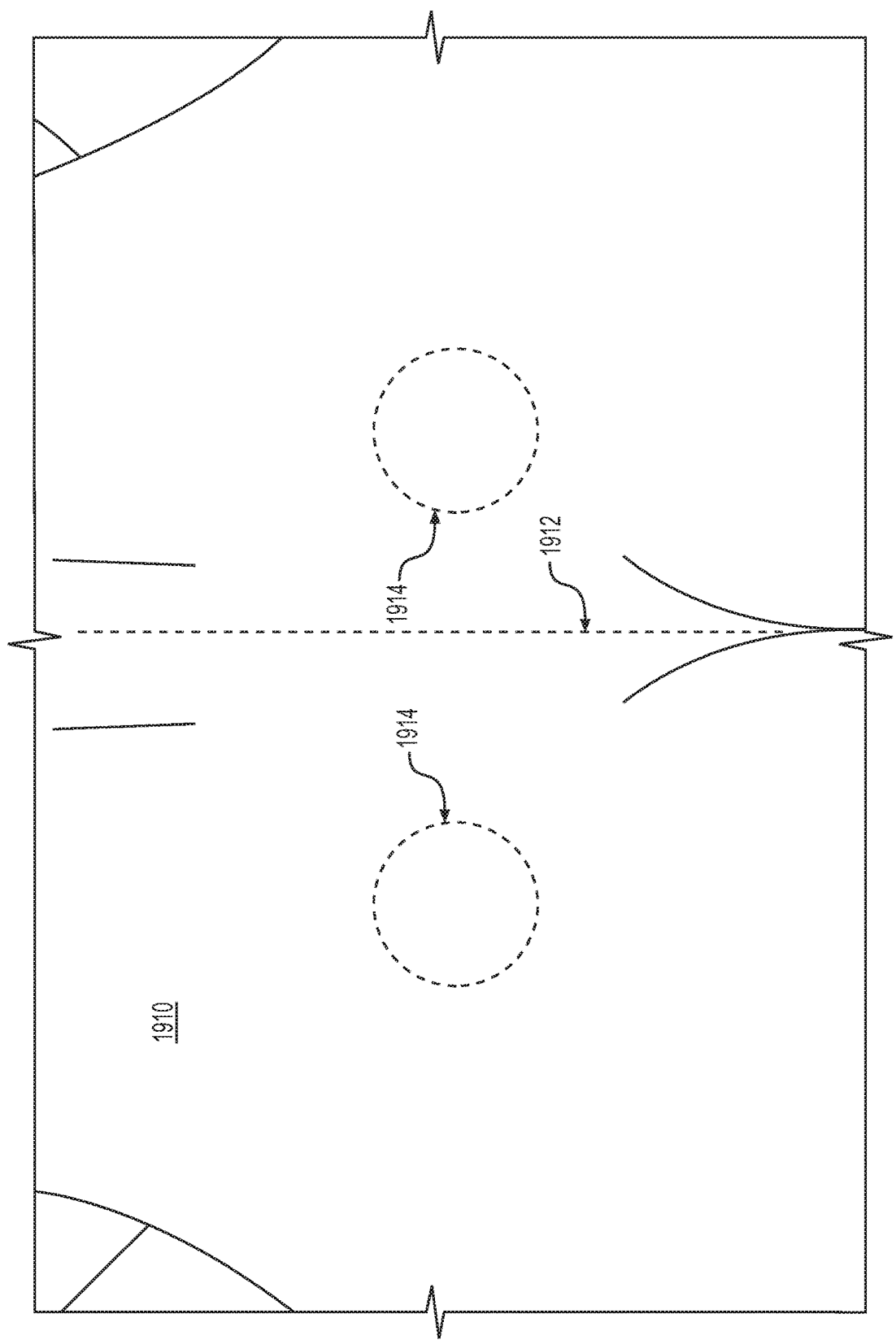
FIG. 22A provides an example of a pair of bisymmetric locations on a sacral region according to the present disclosure.

FIG. 22A depicts the sacral region of the back of a patient 1910. A line of symmetry 1912 can be drawn down the center of the back, dividing the back into left and right mirror images. Locations 1914 are approximately the same distance from line of symmetry 1912 and approximately at the same height and are, therefore, considered to be bisymmetric locations on the back of patient 1910.

Figure 22B:
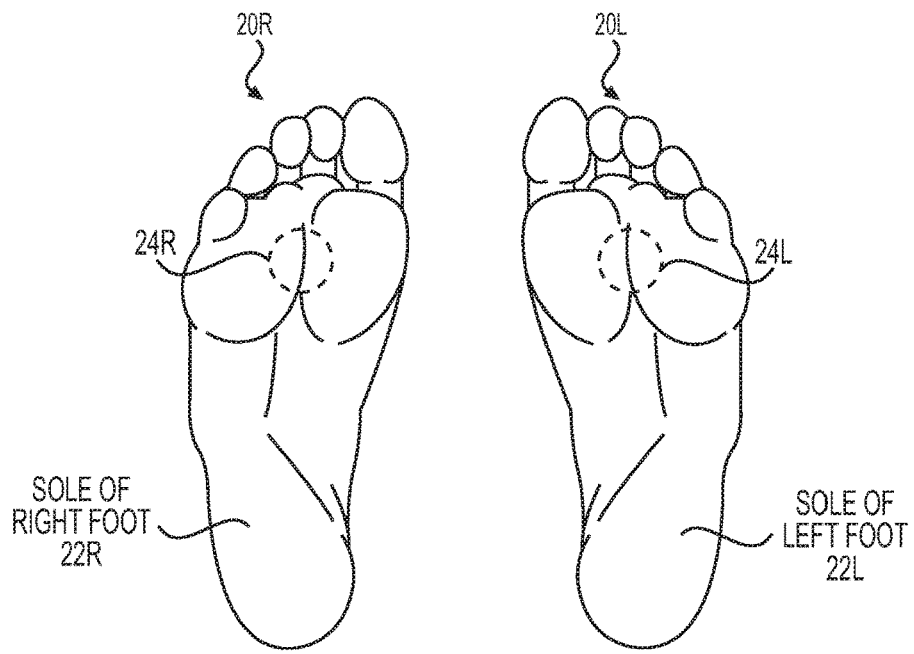
FIG. 22B provides an example of a pair of bisymmetric locations on the bottom side of both feet according to the present disclosure.

FIG. 22B depicts left foot 20L and right foot 20R of a patient 10, as seen if patient 10 were lying on the back on a bed (not shown) and an observer were standing at the foot of the bed. With respect to soles 22L and 22R of feet 20L and 20R, locations 24L and 24R are located at approximately equivalent locations, e.g. the same distance from the posterior surface, i.e. the heel, and the same distance from the medial side of respective foot 20L or 20R and are considered to be bisymmetric locations.

Figure 22C:
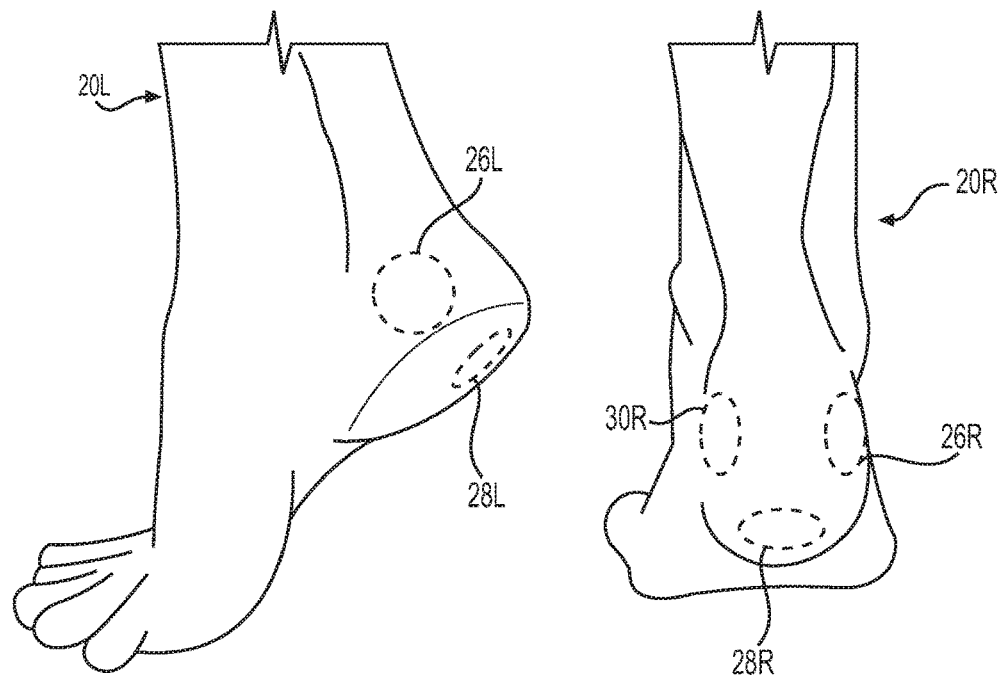
FIG. 22C provides an example of a pair of bisymmetric locations on the lateral sides and soles of both feet according to the present disclosure.

FIG. 22C depicts additional exemplary bisymmetric locations 26L and 26R located on the lateral sides of feet 20L and 20R, and bisymmetric locations 28L and 28R located on respective soles 22L and 22R of feet 20L and 20R. In an aspect, locations 26R and 30R are considered bisymmetric with respect to foot 20R when considered alone without reference to foot 20L.

Without being limited to a particular theory, comparison of perfusion measurements taken at bisymmetric locations can compensate for an offset of readings of a particular patient from a population of patients. For example, a patient may be dehydrated on a particular day when measurements are being made. A comparison of the perfusion value of healthy tissue from the same patient, while in a dehydrated condition, may be shifted from the perfusion value of the same tissue at the same location when the patient is fully hydrated. If the tissue at one location is healthy while the tissue at the bisymmetric location is damaged, a comparison of the readings taken at the bisymmetric locations will exclude the "common mode" effect of dehydration variation at both locations and provide a more robust indication that tissue is damaged at one location.

A perfusion measurement apparatus 400 as provided in FIG. 4 may be used to take measurements at multiple locations, for example a first measurement at a first location and a second measurement at a second location that is bisymmetric relative to the first location. In an aspect, apparatus 400 comprises a processor that can be configured by instructions stored on a non-transitory computer-readable medium to determine a characteristic of the measurements taken at multiple locations or parameters associated with or derived from the measurements, for example one or more of a difference between, an average of, or a difference of each from a common average of perfusion values respectively derived from multiple measurements. In one aspect, apparatus 400 comprises a display configured to show one or more parameters associated with the measurements, for example a delta between perfusion values derived from measurements taken at two bisymmetric locations.

In an aspect, apparatus 400 takes the measurements with two receivers 430A and 430B essentially simultaneously. In one aspect, apparatus 400 takes the measurements in sequence with a time interval between the measurements that ranges from zero to one second or more. In an aspect, a measurement by apparatus 400 is triggered by actuation of a button or an actuator. In one aspect, a measurement by apparatus 400 is triggered automatically based on input from a switching element that is part of apparatus 400, for example a contact sensor, a pressure sensor, an optical sensor, or other type of proximity-detecting device that is positioned, in an aspect, proximate to one or more of receivers 430A and 430B. In one aspect, multiple switching elements have to be simultaneously activated to provide the input to take the measurement. In an aspect, apparatus 400 comprises a processor that is coupled to a circuit and receives information about measured reflected light from the circuit. In one aspect, information is in the form of an analog signal, e.g., an electrical voltage, or a digital signal. In an aspect, a processor is coupled directly to a plurality of receivers and is configured to measure reflected light directly. In one aspect, a processor is configured to convert the plurality of received reflected light measurement into a plurality of perfusion values. In an aspect, a processor is configured by machine-readable instructions that are stored on a non-transitory, computer-readable medium that is electronically coupled to the processor. In one aspect, instructions are loaded from a medium into a processor when apparatus 400 is powered on.

In an aspect, a measured reflected light parameter is related to the perfusion of blood in the epidermis of a patient at a depth that is determined by the spatial geometry of receivers 430A and 430B, the wavelength or wavelengths of light emitted by emitter 420, and other operating characteristics of apparatus 400. In one aspect, the magnitude of reflected light detected by a receiver 430 is equivalent to the perfusion with a value on a predetermined scale. In an aspect, a predetermined scale may range from 0 to 20, such as from 0 to 1, from 0 to 2, from 0 to 3, from 0 to 4, from 0 to 5, from 0 to 6, from 0 to 7, from 0 to 8, from 0 to 9, from 0 to 10, from 0 to 11, from 0 to 12, from 0 to 13, from 0 to 14, from 0 to 15, from 0 to 16, from 0 to 17, from 0 to 18, from 0 to 19. In one aspect, a predetermined scale can be scaled by a factor or a multiple based on the values provided herein. In an aspect, multiple measurements are taken while varying one or more of operating characteristics between readings, thereby providing information related to the perfusion at various depths of the skin.

In one aspect, a difference between perfusion values is determined, where a difference that exceeds a predetermined threshold is indicative of tissue damage at one of the locations where the corresponding perfusion measurements were taken. In an aspect, means of perfusion values obtained at each bisymmetric locations are determined and compared. In one aspect, medians or modes of perfusion values obtained at each bisymmetric locations are determined and compared. In an aspect, the damage is indicated to be at the location associated with the larger of the perfusion values. In one aspect, the damage is indicated to be at the location associated with the smaller of the perfusion values. In an aspect, determination of whether there is tissue damage comprises one or more of comparison of individual perfusion values with one or more predetermined ranges or thresholds and comparison of the difference with one or more predetermined ranges or thresholds. In an aspect, a predetermined range may be from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined range may be from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined range may be from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a predetermined threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined range or threshold can be scaled by a factor or a multiple based on the values provided herein. It will be understood that a predetermined value is not limited by design, but rather, one of ordinary skill in the art would be capable of choosing a predetermined value based on a given unit of perfusion. In one aspect, ranges and thresholds of the present disclosure are varied according to the specific bisymmetric locations, the portion of a patient's body on which measurements are being made, or one or more characteristics of the patient such as age, height, weight, family history, ethnic group, and other physical characteristics or medical conditions.

One or more regions may be defined on a body. In an aspect, measurements made within a region are considered comparable to each other. A region may be defined as an area on the skin of the body wherein measurements may be taken at any point within the area. In an aspect, a region corresponds to an anatomical region (e.g., heel, ankle, lower back). In an aspect, a region may be defined as a set of two or more specific points relative to anatomical features wherein measurements are taken only at the specific points. In an aspect, a region may comprise a plurality of non-contiguous areas on the body. In an aspect, the set of specific locations may include points in multiple non-contiguous areas.

In an aspect, a region is defined by surface area. In an aspect, a region may be, for example, between 5 and 200 $cm^2$, between 5 and 100 $cm^2$, between 5 and 50 $cm^2$, or between 10 and 50 $cm^2$, between 10 and 25 $cm^2$, or between 5 and 25 $cm^2$.

In an aspect, measurements may be made in a specific pattern or portion thereof. In an aspect, the pattern of readings is made in a pattern with the target area of concern in the center. In an aspect, measurements are made in one or more circular patterns of increasing or decreasing size, T-shaped patterns, a set of specific locations, or randomly across a tissue or region. In an aspect, a pattern may be located on the body by defining a first measurement location of the pattern with respect to an anatomical feature with the remaining measurement locations of the pattern defined as offsets from the first measurement position.

In an aspect, a plurality of measurements are taken across a tissue or region and the difference between the lowest measurement value and the highest measurement value of the plurality of measurements is recorded as a delta value of that plurality of measurements. In an aspect, 3 or more, 4 or more, 5 or more, 6 or more, 7 or more, 8 or more, 9 or more, or 10 or more measurements are taken across a tissue or region.

In an aspect, a threshold may be established for at least one region. In an aspect, a threshold of 0.2, 0.3, 0.4, 0.5, 0.6, 0.7, 0.8, 0.9, or other value may be established for the at least one region. In an aspect, a delta value is identified as significant when the delta value of a plurality of measurements taken within a region meets or exceeds a threshold associated with that region. In an aspect, each of a plurality of regions has a different threshold. In an aspect, two or more regions may have a common threshold.

In an aspect, a threshold has both a delta value component and a chronological component, wherein a delta value is identified as significant when the delta value is greater than a predetermined numerical value for a predetermined portion of a time interval. In an aspect, the predetermined portion of a time interval is defined as a minimum of X days wherein a plurality of measurements taken that day produces a delta value greater than or equal to the predetermined numerical value within a total of Y contiguous days of measurement. In an aspect, the predetermined portion of a time interval may be defined as 1, 2, 3, 4, or 5 consecutive days on which a plurality of measurements taken that day produces a delta value that is greater than or equal to the predetermined numerical value. In an aspect, the predetermined portion of a time interval may be defined as some portion of a different specific time period (weeks, month, hours etc.).

In an aspect, a threshold has a trending aspect wherein changes in the delta values of consecutive pluralities of measurements are compared to each other. In an aspect, a trending threshold is defined as a predetermined change in delta value over a predetermined length of time, wherein a determination that the threshold has been met or exceeded is significant. In an aspect, a determination of significance will cause an alert to be issued. In an aspect, a trend line may be computed from a portion of the individual measurements of the consecutive pluralities of measurements. In an aspect, a trend line may be computed from a portion of the delta values of the consecutive pluralities of measurements.

In an aspect, the number of measurements taken within a single region may be less than the number of measurement locations defined in a pattern. In an aspect, a delta value will be calculated after a predetermined initial number of readings, which is less than the number of measurement locations defined in a pattern, have been taken in a region and after each additional reading in the same region, wherein additional readings are not taken once the delta value meets or exceeds the threshold associated with that region.

In an aspect, the number of measurements taken within a single region may exceed the number of measurement locations defined in a pattern. In an aspect, a delta value will be calculated after each additional reading.

In an aspect, a quality metric may be generated for each plurality of measurements. In an aspect, this quality metric is chosen to assess the repeatability of the measurements. In an aspect, this quality metric is chosen to assess the skill of the clinician that took the measurements. In an aspect, the quality metric may include one or more statistical parameters, for example an average, a mean, or a standard deviation. In an aspect, the quality metric may include one or more of a comparison of individual measurements to a predefined range. In an aspect, the quality metric may include comparison of the individual measurements to a pattern of values, for example comparison of the measurement values at predefined locations to ranges associated with each predefined location. In an aspect, the quality metric may include determination of which measurements are made over healthy tissue and one or more evaluations of consistency within this subset of "healthy" measurements, for example a range, a standard deviation, or other parameter.

In an aspect, apparatus 400 is capable of storing multiple measurement and computation results. In one aspect, an apparatus in accordance with the present disclosure may also comprise other components, for example a barcode scanner, and may be capable of storing the output of that component. In an aspect, apparatus 400 comprises components to transfer the stored data, for example via a Bluetooth, WiFi, or Ethernet connection, to another device, for example a personal computer, server, tablet, or smart phone such as depicted in FIG. 13.

In an aspect, apparatus 400 comprises two receivers 430A and 430B which are located at separate locations on the apparatus body. An example usage would be to place apparatus 400 against a patient's body so as to simultaneously position first receiver 430A at a first body location, and position second receiver 430B at a second body location, where both body locations are on the surface of a patient's skin. In an aspect, the apparatus body is rigid and maintains receivers 430A and 430B at a fixed separation distance and fixed orientation to each other. In an aspect, receivers 430A and 430B are aligned on a common plane.

In an aspect, the apparatus body of apparatus 400 is flexible such that receivers 430A and 430B may be oriented at an angle to each other. In an aspect, one or more of receivers 430 are movable such that the angle between a movable receiver and the other receiver may be varied, for example to match the orientation of the skin. In an aspect, both receivers are movable In an aspect, all receivers are movable. In an aspect, apparatus 400 comprises a hinge such the separation distance between receivers 430A and 430B may be varied. In an aspect, the apparatus body of apparatus 400 is rigid such that the angle and the separation distance between the receivers are immovable.

In an aspect, apparatus 400 comprises a plurality of emitters 420 and a plurality of receivers 430 to form a planar array. In an aspect, the planar array may take the form of a mat on which emitters 420 and receivers 430 are disposed. In one aspect, the emitters 420 and receivers 430 are embedded within the mat. In an aspect, the emitters 420 and receivers 430 are located on the top surface the mat. In an aspect, the emitters 420 and receivers 430 have a cover layer over them. In an aspect, the emitters 420 are of a single type and configuration within the array. In an aspect, the receivers 430 are of a single type and configuration within the array. In an aspect, the emitters 420 vary in size and type within the array. In an aspect, the receivers 430 vary in size and type within the array. In an aspect, the emitters 420 and receivers 430 of the array are disposed in a regular geometric pattern, such as a grid-like pattern. In an aspect, the emitters 420 and receivers 430 of the array are disposed in an irregular pattern. In an aspect, the mat is coupled to an electronics assembly either directly or through a cable. In one aspect, an electronics assembly comprises a circuit coupled to receivers 430 and a processor is coupled to the circuit. In an aspect, the mat comprises one or more of pressure sensors, temperature sensors, optical sensors, and contact sensors disposed at one or more respective locations across the mat. In one aspect, one or more measurements using receivers 430 are triggered by input from one or more of the pressure, temperature, optical, and contact sensors. In an aspect, the mat is configured as a floor mat and actuation of one or more of the pressure, temperature, optical, and contact sensors, for example detection of a person standing on the mat due to detection of the weight of a person by a pressure sensor, initiates a measurement by one or more of receivers 430. In one aspect, receivers 430 are operated in a "detection mode" that is capable of detecting when a person steps onto mat and transitions into a "measurement mode" upon determination that a person is standing on the mat. In an aspect, the mat is configured as a portable apparatus that can be placed against a surface of a patient's skin, for example against a patient's back or against the soles of one or both of their feet while the patient is lying in bed. In one aspect, the mat comprises one or more of a support tray, stiffening element, and conformal pad to aid in placing receivers 430 against a surface of a patient's skin.

In an aspect, two emitters may overlap 0-50%, such as 0-10%, 5-15%, 10-20%, 15-25%, 20-30%, 25-35%, 30-40%, 35%-45%, 40-50%, 0-25%, 15-35%, or 25-50%. In one aspect, two emitters may overlap 25-75%, such as 25-35%, 30-40%, 35%-45%, 40-50% 45-55%, 50-60%, 55-65%, 60-70%, 65-75%, 25-50%, 40-55%, or 50-75%. In one aspect, two emitters may overlap 50-100%, such as 50-60%, 55-65%, 60-70%, 65-75%, 70-80%, 75%-85%, 80-90%, 85-95%, 90-100%, 50-75%, 65-85%, or 75-100%.

In an aspect, two receivers may overlap 0-50%, such as 0-10%, 5-15%, 10-20%, 15-25%, 20-30%, 25-35%, 30-40%, 35%-45%, 40-50%, 0-25%, 15-35%, or 25-50%. In one aspect, two receivers may overlap 25-75%, such as 25-35%, 30-40%, 35%-45%, 40-50% 45-55%, 50-60%, 55-65%, 60-70%, 65-75%, 25-50%, 40-55%, or 50-75%. In one aspect, two receivers may overlap 50-100%, such as 50-60%, 55-65%, 60-70%, 65-75%, 70-80%, 75%-85%, 80-90%, 85-95%, 90-100%, 50-75%, 65-85%, or 75-100%.

In one aspect, the planar array of may further comprise a plurality of contact sensors on the same planar surface as, and surrounding, each of the receivers to ensure complete contact of each of the emitters and receivers to the skin surface. The plurality of contact sensors may be a plurality of pressure sensors, a plurality of light sensors, a plurality of temperature sensors, a plurality of pH sensors, a plurality of perspiration sensors, a plurality of ultrasonic sensors, a plurality of bone growth stimulator sensors, or a plurality of a combination of these sensors. In an aspect, the plurality of contact sensors may comprise four, five, six, seven, eight, nine, or ten or more contact sensors surrounding each emitter or receiver.

Figure 23A:
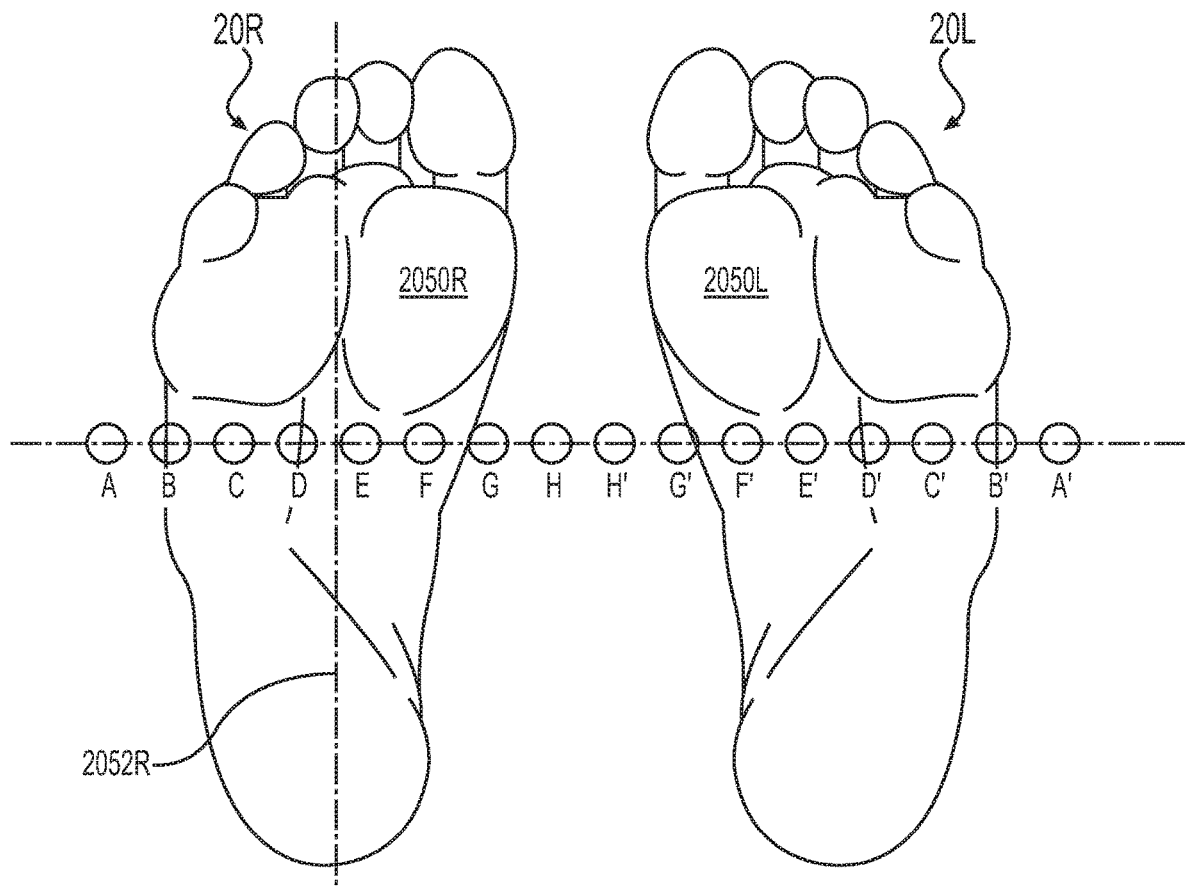
FIG. 23A illustrates locations on the left and right feet for perfusion measurements according to the present disclosure.
Figure 23B:
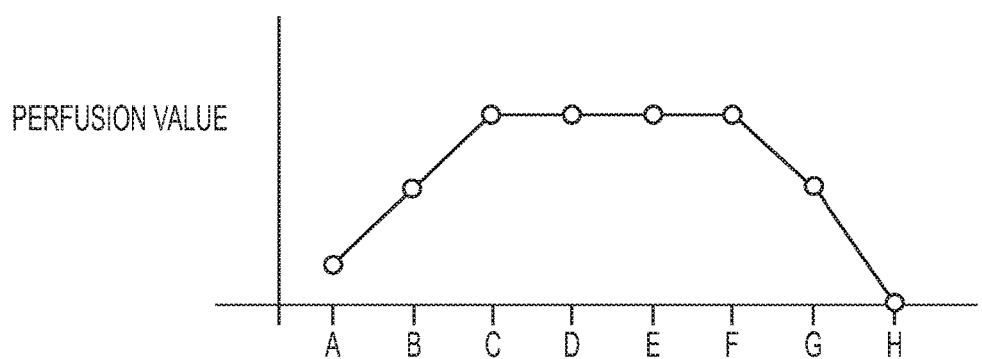
FIG. 23B is a plot of perfusion values associated with known relative locations for identifying bisymmetric locations according to the present disclosure.

FIGS. 23A and 23B depict an example of how comparison of perfusion values associated with receivers in known relative locations can identify bisymmetric locations, according to the present disclosure. In this example, a receiver 430 is presented at non-overlapping locations, marked "A" to "H" in FIG. 23A, across a contact area 2050R of a right foot 20R. The perfusion values measured at each location are plotted in the graph of FIG. 23B. In this example, the perfusion value of locations "A" and "H" are low or zero, reflecting the non-overlap of the receiver 430 with contact area 2050R in those locations. The perfusion values associated with locations "B" and "G" are higher, as the receiver 430 overlaps a portion of contact area 2050R in those positions. The perfusion values for locations C-D-E-F are higher and, in this example, approximately the same, indicating that the receiver 430 is completely within contact area 2050R at those locations. In one aspect, a perfusion measurement apparatus such as apparatus 400 may determine that certain locations, for example locations "C" and "F," are bisymmetric with respect to a centerline 2052R of right foot 20R. In an aspect, where a similar set of measurements is made at locations A'-H' on left foot 20L, a location on each foot 20L and 20R, for example locations E and E', may be determined to be approximately bisymmetric.

Figure 24:
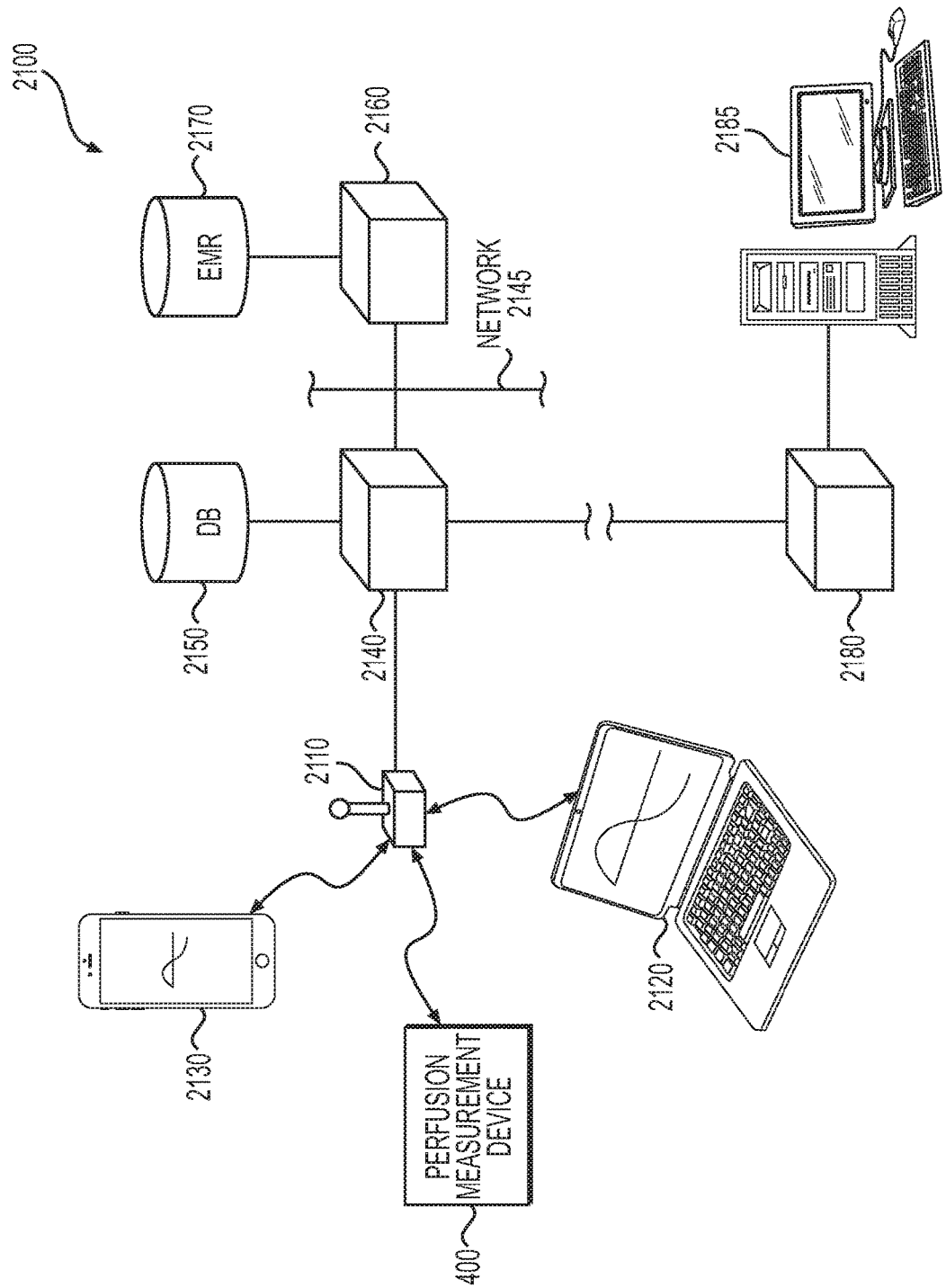
FIG. 24 depicts an integrated system for measurement, evaluation, storage, and transfer of perfusion values, according to the present disclosure.

FIG. 24 depicts a schematic depiction of an integrated system 2100 for measurement, evaluation, storage, and transfer of perfusion values, according to the present disclosure. In this example, system 2100 comprises a perfusion measurement apparatus 400, as discussed with respect to FIG. 4, that comprises the capability to wirelessly communicate with a WiFi access point 2110. Apparatus 400 communicates with one or more of a perfusion application running on a server 2140, an application running on a laptop computer 2120, a smart phone 2130, or other digital device. In one aspect, laptop computer 2120 and smart phone 2130 are carried by a user of apparatus 400, for example a nurse, and an application provides feedback and information to the user. In an aspect, information received from apparatus 400 for a patient is stored in a database 2150. In one aspect, information received from apparatus 400 is transferred over a network 2145 to another server 2160 that stores a portion of information in an electronic medical record (EMR) 2170 of a patient. In one aspect, information from apparatus 400 or retrieved from database 2150 or EMR 2170 is transferred to an external server 2180 and then to a computer 2185, for example a computer at the office of a doctor who is providing care for a patient.

Perfusion Measurement Trend Analysis to Detect Tissue Damage

Figure 25:
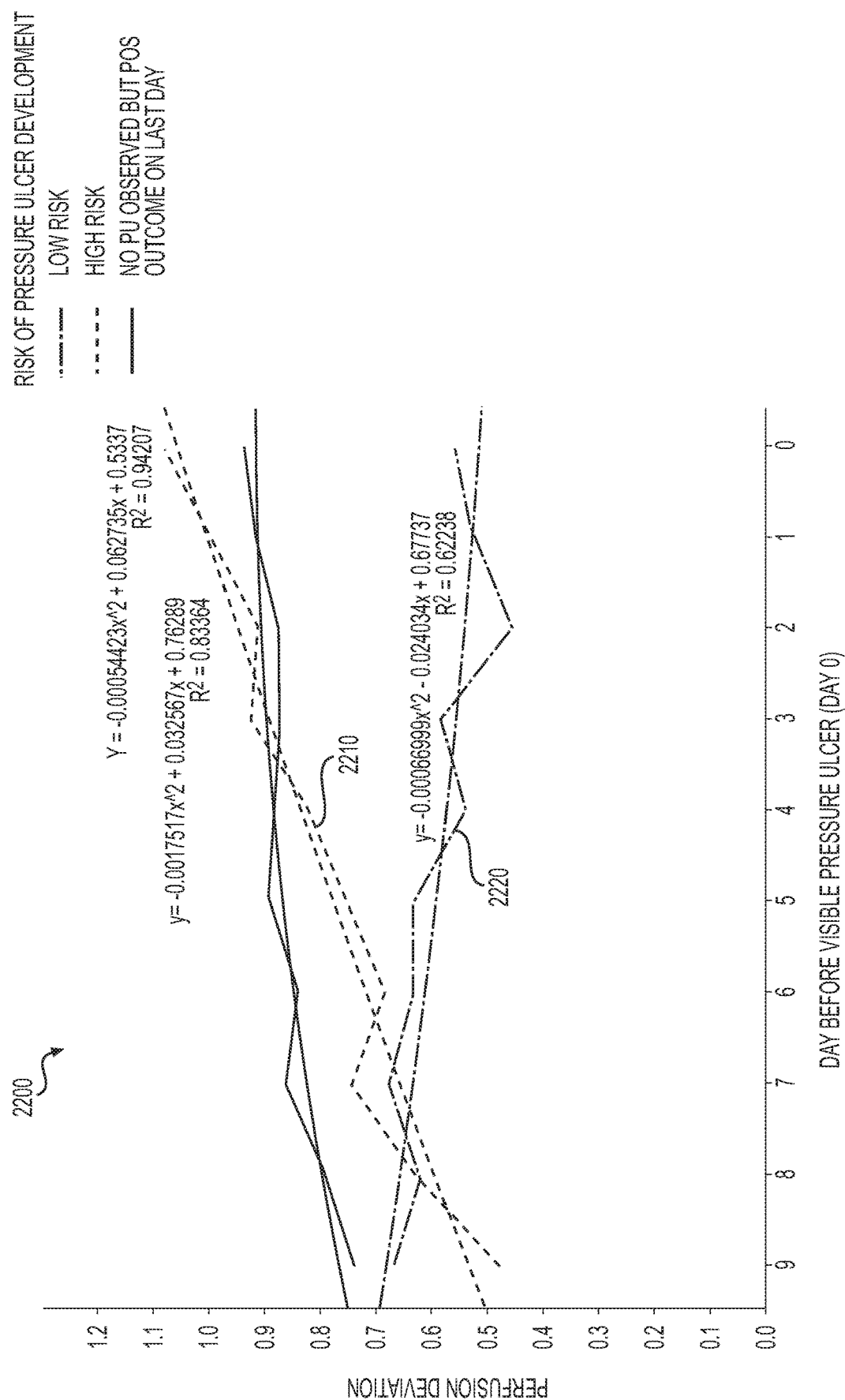
FIG. 25 depicts perfusion values over time for patients who are at risk of developing pressure ulcers, in accordance with the present disclosure.

FIG. 25 depicts perfusion values over time for patients who are at risk of developing pressure ulcers, in accordance with the present disclosure. In an aspect, a perfusion value is a single perfusion measurement. In an aspect, a perfusion value is an average perfusion measurement generated from perfusion measurement values taken at approximately the same location on a patient's skin within a 24-hour period, such as within a 18-hour period, within a 12-hour period, within a 8-hour period, within a 6-hour period, within a 4-hour period, within a 3-hour period, within a 2-hour period, within an hour, within 45 minutes, within 30 minutes, within 15 minutes, within 10 minutes, within 5 minutes, within 1 minute, or within 30 seconds.

Curve 2210 represents average perfusion values for a set of patients having a high risk of developing pressure ulcers over the days leading up to the development of a pressure ulcer on Day 0. The overlaid straight line is a linear approximation. Curve 2220 represents average perfusion values for a set of patients having a low risk of developing pressure ulcers over the days leading up to Day 0, where no pressure ulcer develops on Day 0. In both cases, there was no sign of damage or indication of a future pressure ulcer on the skin. The perfusion values were indicative of subsurface damage that was invisible to visual and tactile examination (e.g. change in elasticity or temperature). The overlaid straight line is a linear approximation.

Figure 26:
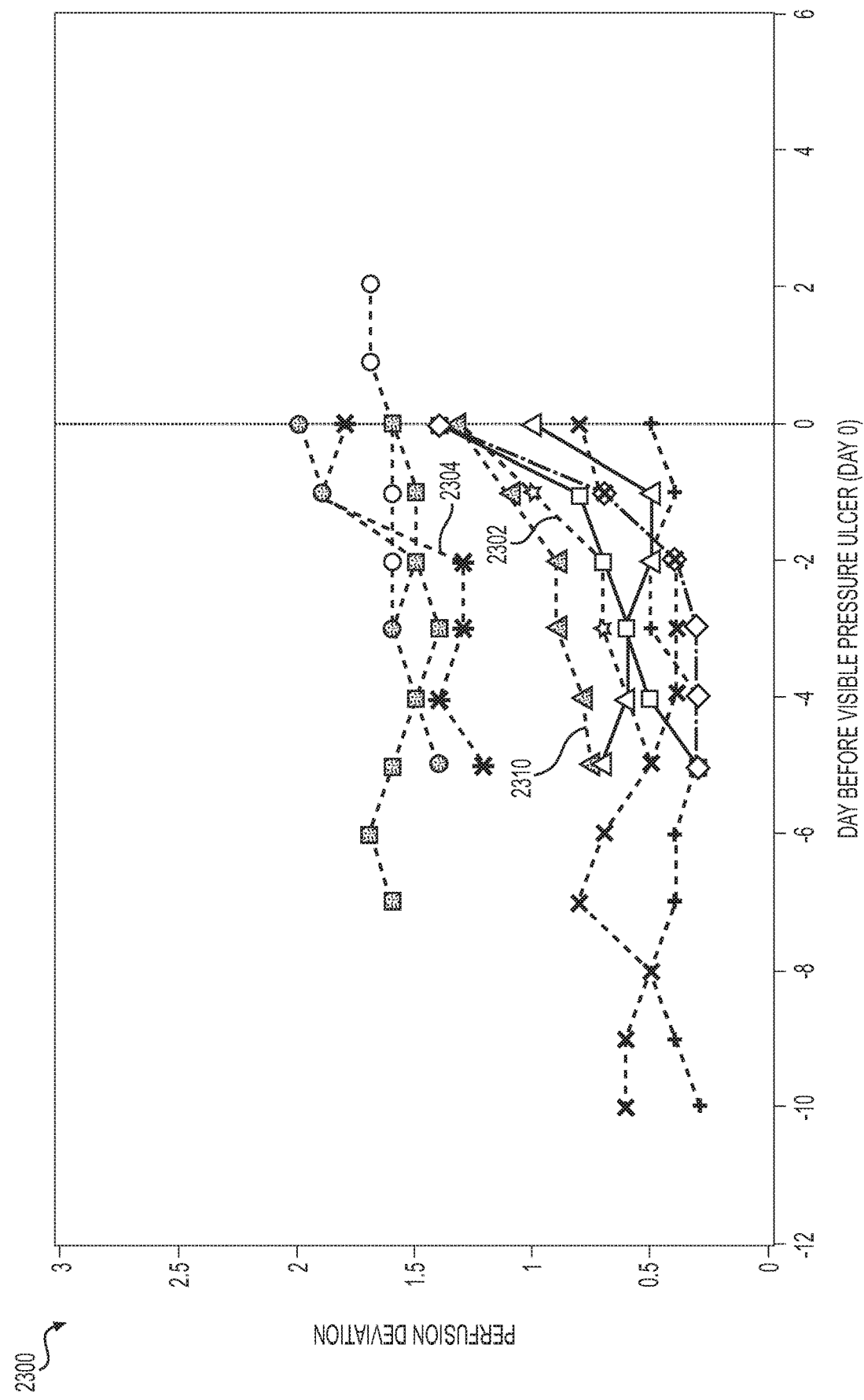
FIG. 26 depicts perfusion delta values over time for patients that develop pressure ulcers, in accordance with the present disclosure.

FIG. 26 depicts perfusion delta values over time for patients that develop pressure ulcers, in accordance with the present disclosure. Curves 2302 and 2304 illustrate the acceleration of the rate of increase, i.e. the slope, of the curve as time gets closer to the point at which a visual examination leads to a clinical diagnosis. Curve 2310 is an average of the other curves and shows the upward curve, i.e. acceleration of the rate of increase.

Figure 27:
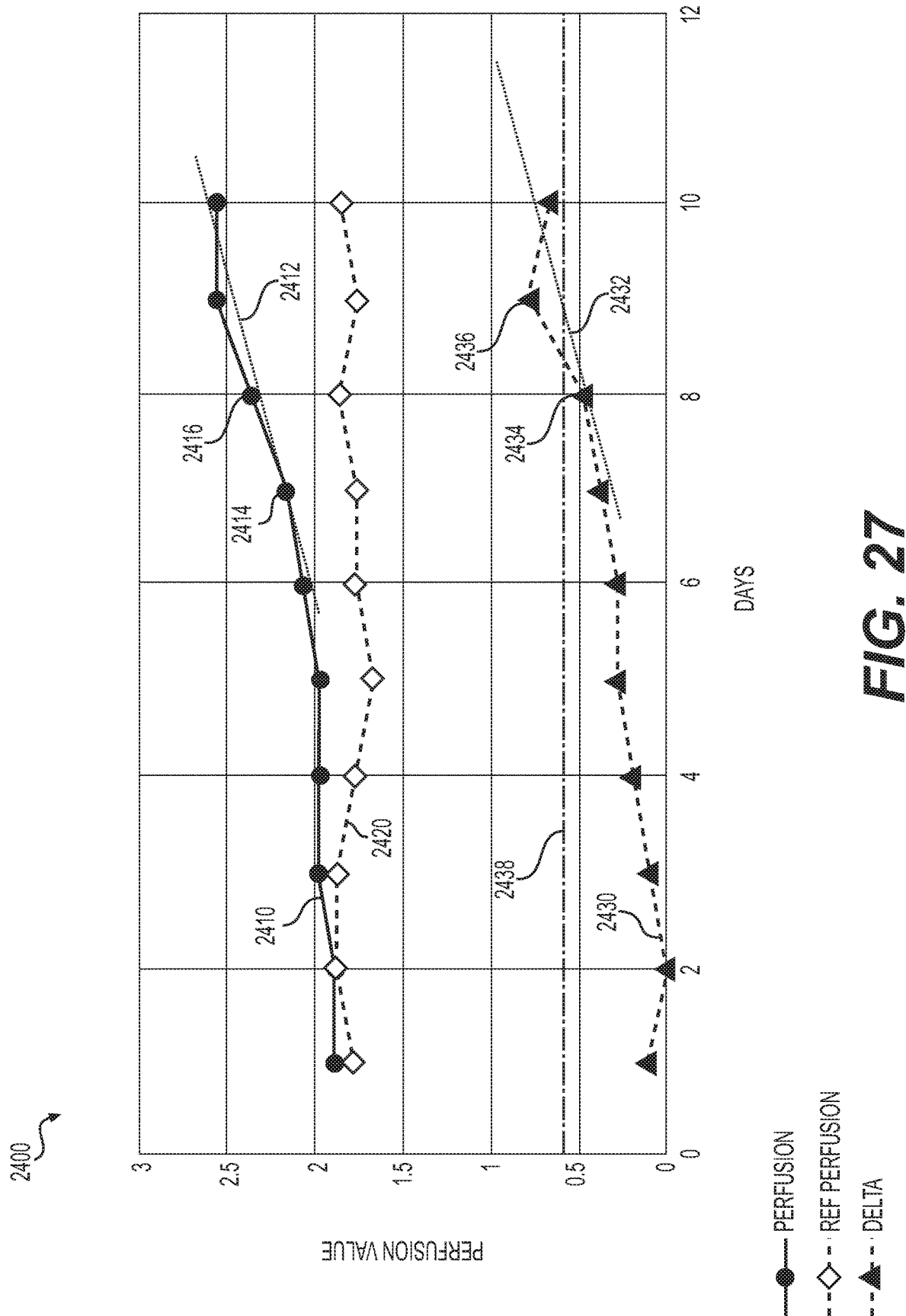
FIG. 27 depicts illustrative perfusion values and delta values over time for patients that develop pressure ulcers, in accordance with the present disclosure.

FIG. 27 is an example plot of measured and computed perfusion values, in accordance with the present disclosure. Curve 2410 is a set of perfusion values for a skin area that is prone to development of a pressure ulcer. Curve 2420 is a matching set of perfusion values for a second skin area that is near the first area but not at risk for a pressure ulcer. Curve 2420 serves as a reference. Curve 2430 is a "delta" perfusion value calculated by subtracting the reference value of curve 2420 from the matching perfusion value of curve 2410.

Tissue damage may be detected in several ways. In one aspect, the slope of the perfusion curve 2410, for example the slope between points 2414 and 2416, is compared against a threshold slope, indicated by line 2412. If the slope of the curve 2410 exceeds the slope of line 2412, this indicates a degree of damage. There may be multiple slopes used to evaluate multiple degrees of tissue damage. In one aspect, a slope is determined with respect to any two points on perfusion curve 2410, and is compared to the slope of line 2412 to indicate a degree of damage. In an aspect, a slope is determined by taking the derivative of the perfusion curve 2410. In an aspect, the slope of line 2412 is determined by the health history of the subject. In one aspect, the curvature of a perfusion curve is compared to a threshold curvature, where an over-curvature indicates a degree of damage.

In an aspect, tissue damage may be detected before it is visible on a patient's skin by: measuring a plurality of $SpO_2$ values at a single location at incremental times, calculating a slope between the latest $SpO_2$ value and the immediately prior $SpO_2$ value, comparing this slope to a threshold value, and determining that there is tissue damage if the slope exceeds the threshold value.

In an aspect, tissue damage may be detected before it is visible on a patient's skin by: measuring a plurality of $SpO_2$ values at a single location at incremental times, calculating a derivative between the latest $SpO_2$ value and the immediately prior $SpO_2$ value, comparing this derivative to a threshold value, and determining that there is tissue damage if the derivative exceeds the threshold value.

In an aspect, the value of the delta curve 2430 is compared to a threshold level 2438. When curve 2430 exceeds threshold 2438, for example at point 2436, this indicates a degree of damage. There may be multiple thresholds used to evaluate multiple levels of tissue damage.

In an aspect, tissue damage may be detected before it is visible on a patient's skin by: measuring a plurality of $SpO_2$ values at a single location at each of a plurality of incremental times, calculating an average value for each incremental time, fitting a curve to a predetermined number of the most-recent $SpO_2$ average values, calculating a curvature of the fitted curve, comparing this curvature to a threshold value, and determining that there is tissue damage if the curvature exceeds the threshold value.

In an aspect, a threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value based on a given unit of perfusion. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In one aspect, the slope of the delta curve 2430, for example the slope between points 2434 and 2436, is compared against a threshold slope, indicated by line 2432. If the slope of the curve 2430 exceeds the slope of line 2432, this indicates a degree of damage. There may be multiple slopes used to evaluate multiple degrees of tissue damage. In one aspect, a slope is determined with respect to any two points on delta curve 2430, and is compared to the slope of line 2432 to indicate a degree of damage. In an aspect, the slope of line 2432 is determined by the health history of the subject. In one aspect, the curvature of a delta curve is compared to a threshold curvature, where an over-curvature indicates a degree of damage.

In an aspect, a perfusion delta value above a predefined threshold value is an indication of sub-epidermal damage that may lead to a pressure ulcer. The time interval between the time when the perfusion delta value first equals or exceeds this threshold and the development of visible symptoms of a pressure ulcer may be a first duration when the perfusion delta value increases linearly. A first duration may be 5 or more days, such as 6 or more days, 7 or more days, 8 or more days, 9 or more days, or 10 or more days.

In another aspect, when the perfusion delta curve shows an upward curvature or other deviation above a linear progression, the visible symptoms may be present within a shorter amount of time, for example 2-3 days, 1-4 days. 1-3 days, 1-2 days, or 2-4 days. In an aspect, the perfusion measurement apparatus 400, which includes a receiver 430 and electronics to measure reflected light and convert this reflected light measurement to a perfusion value and store a plurality of these perfusion values then calculate and display a perfusion delta value from the plurality of perfusion values and transmit a portion of the measurements and delta values to a remote computer, is used to generate a perfusion delta value for a particular location on the patient's skin, for example the heel. These perfusion delta values are tracked and the trend of the perfusion delta values, i.e. the slope and curvature of a curve connecting these perfusion delta values, is analyzed. In an aspect, the amount by which an incremental perfusion delta value is above a linear prediction based on prior perfusion delta values is compared to a predetermined threshold. In an aspect, the amount by which an incremental perfusion delta value is above the most recent prior perfusion delta value is compared to a predetermined threshold. In an aspect, a curvature of the best-fit curve fitted to a predefined number of the most-recent perfusion delta values is compared to a predetermined threshold. In an aspect, the number of sequential perfusion delta values that exceeds a predetermined value threshold is compared to a number-of-readings threshold. In each of these aspects, the perfusion scanner provides a notification when the comparison parameter exceeds the respective threshold.

In an aspect, the trend analysis may ignore a single perfusion delta value that is below a threshold if both the prior and subsequent perfusion delta values are above the threshold.

In an aspect, the trend curve of the perfusion delta values is a point-to-point linear connection. In an aspect, the trend curve is a best-fit curve fitted to the perfusion delta values. In an aspect, the fitted curve is required to intersection the most-recent perfusion delta value.

Having now generally described the invention, the same will be more readily understood through reference to the following examples that are provided by way of illustration, and are not intended to be limiting of the present disclosure, unless specified.

EXAMPLES

Example 1: Intervention Levels for Treating Pressure Ulcers in the Heel

Subjects identified as being at risk for pressure ulcers in the heel are treated in accordance with the following scheme:

TABLE 1

EXAMPLE INTERVENTION SCHEME FOR TREATING A PRESSURE ULCER IN THE HEEL

| Risk Level | Intervention | Frequency of Subsequent Perfusion Measurement Monitoring | Corresponding Perfusion delta Ranges |
| --- | --- | --- | --- |
| 0 | provide good nutrition, standard mattress, and/or turn every 24 hours | every 24 hours | perfusion delta ≤ threshold |
| 1 | provide a heel boot | every 10 hours | threshold < perfusion delta ≤ 105% threshold |
| 2 | change of support surface | at the beginning of each nursing shift | 105% threshold < perfusion delta ≤ 110% threshold |
| 3 | apply dressing to back or sides of heel | every 12 hours | 110% threshold < perfusion delta ≤ 115% threshold |
| 4 | change to low-friction sheet cover | every 8 hours | 115% threshold < perfusion delta ≤ 120% threshold |
| 5 | provide a low-friction padded mattress surface for lower leg | every 6 hours | 120% threshold < perfusion delta ≤ 125% threshold |
| 6 | turn patient at a shorter interval | every 4 hours | 125% threshold < perfusion delta ≤ 130% threshold |
| 7 | apply barrier cream | every 2 hours | 130% threshold < perfusion delta ≤ 135% threshold |

TABLE 1-continued

EXAMPLE INTERVENTION SCHEME FOR TREATING A PRESSURE ULCER IN THE HEEL

| Risk Level | Intervention | Frequency of Subsequent Perfusion Measurement Monitoring | Corresponding Perfusion delta Ranges |
|---|---|---|---|
| 8 | apply neuro-muscular stimulation | every 1 hour | 135% threshold < perfusion delta ≤ 145% threshold |
| 9 | apply topical cream to enhance perfusion | every 30 minutes | 145% threshold < perfusion delta ≤ 150% threshold |
| 10 | provide silicone pad for lower leg | every 15 minutes | 150% threshold < perfusion delta |

Example 2: Intervention Levels for Treating Pressure Ulcers in the Sacrum

Subjects identified as being at risk for pressure ulcers in the sacrum are treated in accordance with the following scheme:

TABLE 2

EXAMPLE INTERVENTION SCHEME FOR TREATING A PRESSURE ULCER IN THE SACRUM

| Risk Level | Intervention | Frequency of Subsequent Perfusion Measurement Monitoring | Corresponding Perfusion delta Ranges |
|---|---|---|---|
| 0 | provide good nutrition, standard mattress, and/or turn every 24 hours | every 24 hours | perfusion delta ≤ threshold |
| 1 | reposition patient with wedge and/or keep sacrum dry | every 10 hours | threshold < perfusion delta ≤ 110% threshold |
| 2 | change mattress to pressure-alleviating mattresses | at the beginning of each nursing shift | 110% threshold < perfusion delta ≤ 120% threshold |
| 3 | apply dressing over sacrum | every 12 hours | 120% threshold < perfusion delta ≤ 130% threshold |
| 4 | change to dynamic mattress | every 8 hours | 130% threshold < perfusion delta ≤ 140% threshold |
| 5 | apply barrier cream | every 6 hours | 140% threshold < perfusion delta ≤ 150% threshold |
| 6 | apply neuro-muscular stimulation | every 4 hours | 150% threshold < perfusion delta ≤ 160% threshold |
| 7 | apply topical cream to enhance perfusion | every 2 hours | 160% threshold < perfusion delta ≤ 170% threshold |
| 8 | provide silicone pad under the patient's body | every 1 hour | 170% threshold < perfusion delta ≤ 180% threshold |

Example 3: Example Process for Selecting a Level of Intervention and Monitoring

Figure 15:
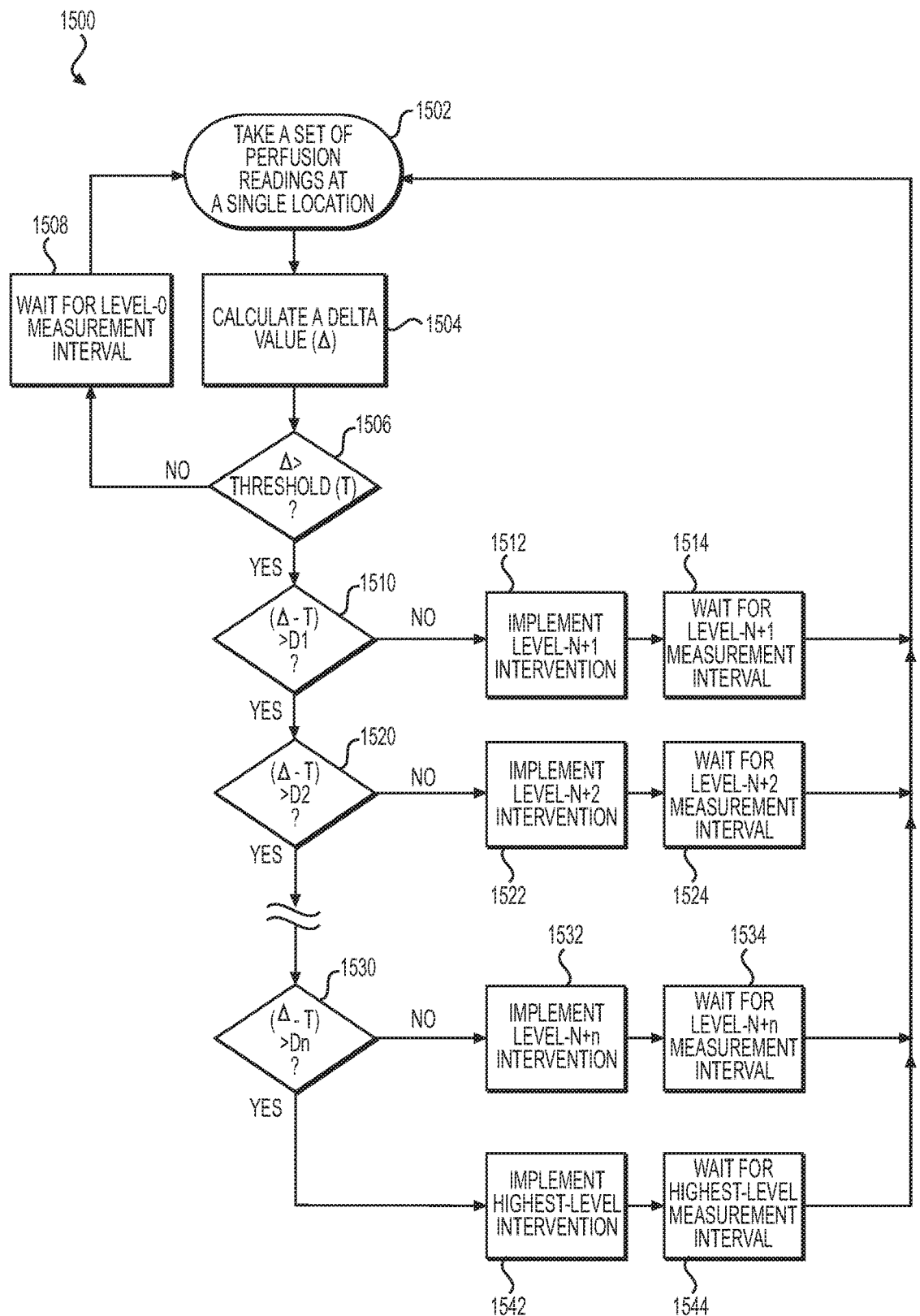
FIG. 15 is an illustration of a process for selecting a level of intervention and monitoring based on the amount by which a delta value derived from perfusion measurements exceeds a threshold value in accordance with the present disclosure.

FIG. 15 is an illustration of a process 1500 for selecting a level of intervention and monitoring based on the amount by which a delta value derived from perfusion measurements exceeds a threshold value. Here, a caregiver takes a plurality of perfusion measurements at a location on the skin of a patient in step 1502, where each measurement generates a perfusion value. Using a portion of these perfusion values, a delta value "Δ" is calculated in step 1504. The delta value is calculated by subtracting the smallest perfusion value from the largest perfusion value generated from the plurality of perfusion measurements.

The calculated delta value is compared to a threshold value "T" in step 1506. If the delta value is less than or equal to the threshold value, step 1508 is executed and the caregiver waits until the monitoring interval associated with the current level of care transpires, then repeats the perfusion measurements in step 1502. If the delta value is greater than the threshold value, the amount by which the delta value exceeds the threshold value is compared to a cascading series of difference values.

In some instances, the delta value is positive and the comparison executed by subtracting the threshold value from the delta value, which produced a positive difference, and then a determination is made regarding whether the difference exceeded the first difference D1 in step 1510. If the difference is less than D1, the process branched to step 1512 and then step 1514 to implement an intervention and measurement interval, respectively, associated with level-N+1. In this example, N has a value of zero or greater.

In some instances, the delta value is negative. In that case, the differences D1, D2 through Dn are selected to have negative values that can have different absolute values than the corresponding difference values D1, D2 through Dn used for a positive delta value. Alternatively, the comparisons in steps 1510, 1520, and 1530 are changed to "≤" in place of the "≥" shown in FIG. 15.

Example 4: Workflow Guidance Matrix

FIG. 16 is an example of a workflow guidance matrix 1600 where the current level of intervention 1602 and the new delta value 1604 are used to select the new level of intervention 1606. Here, a caregiver monitors the condition of a patient by periodically taking a plurality of perfusion measurements at one or more locations on the patient's skin. At the time of these measurements, the patient receives care associated with a level of intervention and monitoring. In this example, level-0 (zero) is associated with a patient who was not considered to be at significant risk for development of tissue damage. Higher levels of intervention and monitoring are identified with the gradations of intervention ranked, for example, according to cost, difficulty to implement, or other parameter identified by the care facility. When a caregiver is making a new set of perfusion measurements, they consult this matrix by identifying the row of the current level of intervention 1602, the delta value determined from the latest set of perfusion measurements 1604, and identifies the level of intervention in the cell 1606 at the intersection of the row 1602 and column 1604. The caregiver can consider the identified level of intervention as well as the current level of intervention and the value of the delta in selecting a level of intervention for the next time period.

In some instances, the values of the new levels of intervention in the cells 1606 are similar from row to row. In some instances, the values of the new levels of intervention in adjacent cells 1606 differed by a single level or by more than one level. In some instances, the values of the new levels of intervention in adjacent cells 1606 are the same in adjacent cells.

Example 5: Progression of Tissue Condition Leading to Development of a Wound

Figure 17:
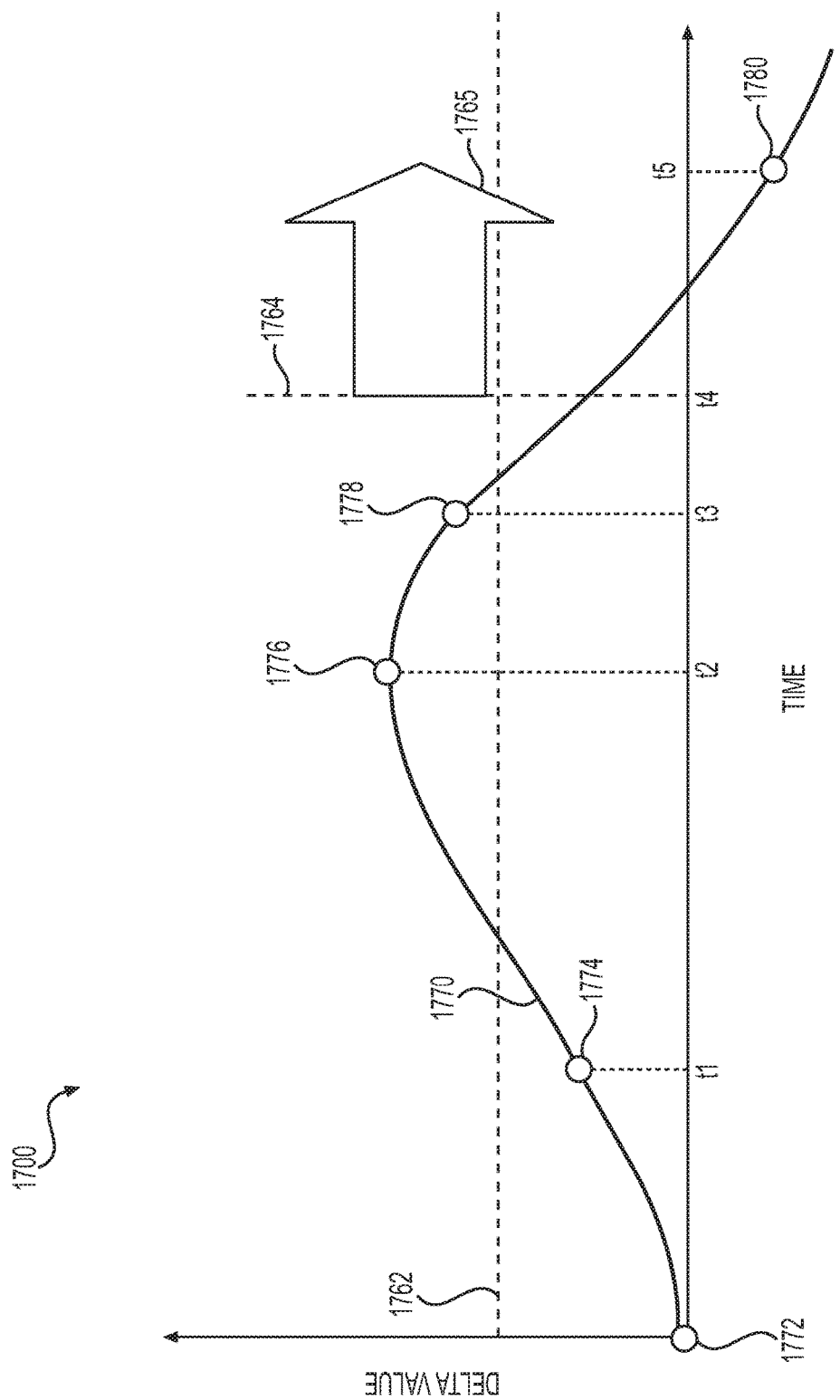
FIG. 17 is an example plot of a delta value change over time for a single patient at a single wound location in accordance with the present disclosure.

FIG. 17 shows an illustrative plot 1700 of a delta value for a single patient at a single location where a wound develops. The perfusion values are measured by an apparatus of for assessing perfusion of blood in tissue below a patient's skin. A delta value is generated from sets of perfusion measurements taken at incremental times. Point 1772 is a measurement at time=zero where all the perfusion values had a baseline value associated with healthy tissue and the delta value is zero. At time t1, another set of perfusion measurements is made and the associated delta value is indicated at point 1774. This delta value is below the threshold 1762 and, therefore, there is no indication of significant sub-surface damage.

At time t2, the damage progresses and the delta value 1776 is greater than the threshold 1762, indicating that there is significant damage. This damage is still not visible on the skin. Nonetheless, a delta value greater than the threshold 1762 indicates that there is cellular damage at a depth less than the sensitive depth of the perfusion measurement apparatus.

At time t3, the damage continues but the amount of fluid in the intercellular space is decreased due to mechanical expulsion. This reduced the perfusion value taken over the damaged area, which reduced the computed delta value 1778 since the perfusion value of the healthy tissue remains much the same as during previous measurements.

At time t4, the damage progresses to the point where it was visible on the skin surface. In some instances, time t4 may occur before one or both of t2 and t3. In some instances, time t4 may occur after the delta value has reached zero again along curve 1770 after time t3 and before t5. Arrow 1765 indicates that after time t4, the damage remains visible.

At time t5, the damage progresses to the point where sufficient fluid has been expelled from the local tissue that the perfusion value of a measurement made over the damaged area is lower than the perfusion value of healthy tissue. This results in the delta value 1780 being negative. In some instances, the negative delta would indicate that the tissue is seriously damaged. In some instances, the negative delta would indicate that a portion of the tissue at the location of the lowest perfusion value is necrotic.

Example 6: Method of Mapping an Area of Possible Damage I

Figure 18A:
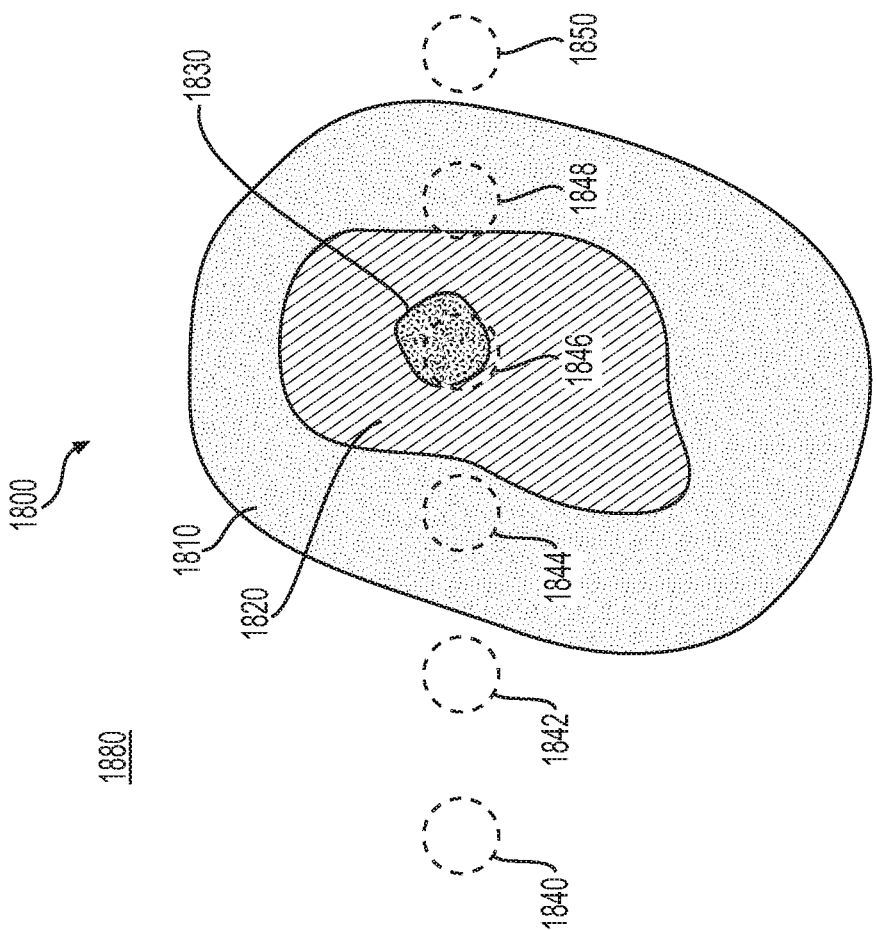
FIGS. 18A and 18B are examples of methods of mapping areas of tissue damage in accordance with the present disclosure.

FIG. 18A is an example of a method of mapping an area of possible damage. The area of damage 1800 is surrounded by healthy tissue 1808. The center area 1830 is significantly damaged. The first surrounding area 1820 is less damaged, and the second surrounding area 1810 is less damaged but still not healthy tissue. The skin over all of these areas have the same appearance and texture, with no indication of the subsurface damage. The series of dashed-line circles 1840, 1842, 1844, 1846, 1848, and 1850 indicate an example set of location where perfusion measurements were taken. Perfusion measurements taken at locations 1840, 1842, and 1850 generally produce a perfusion value associated with healthy tissue, identified within this example as "H." Perfusion measurements taken at locations 1844 and 1848 generally produce a perfusion value "J" that is slightly higher than H. A perfusion measurement taken at location 1846 generally produces a perfusion value "P" that is greater than J. All of these measurements are considered to be taken at a single "location" on the patient's body, for example the sacrum, even though the individual locations are spatially dispersed over this location. For this set of perfusion values, the delta is the difference between the highest perfusion value, which likely occurred at location 1846, and the lowest perfusion value, which likely occurred at one of locations 1840, 1842, and 1850, within this set. If the delta is greater than a threshold value "T," this is an indication that there is significant damage at this location. The exact location of the greatest damage is likely to be proximate to the measurement location 1846 where the greatest perfusion value is produced.

Example 7: Method of Mapping an Area of Possible Damage II

Figure 18B:
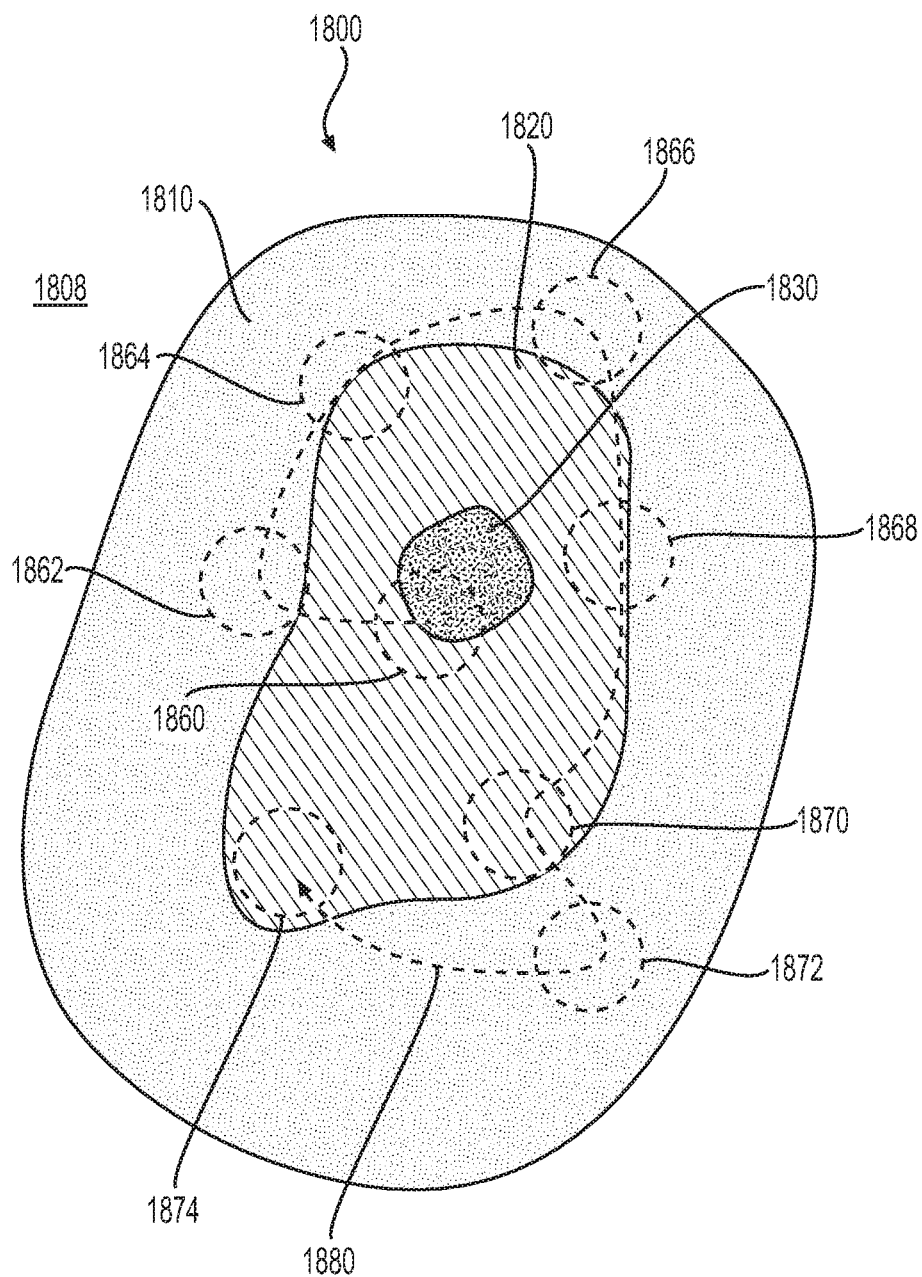

FIG. 18B depicts a second example of mapping an area of possible damage. In this example, the approximate location of the greatest damage is known, for example from prior application of the method illustrated in FIG. 18A. The intent of this method is to map the boundary between area 1810 and area 1820 to determine the extent of the damage. For simplicity, the perfusion values produced by measurements in each area were the same and the perfusion values increased from area 1810 to area 1820 and then to area 1830. The first perfusion measurement is taken at location 1860, which is known to be the approximate location of the greatest damage. Subsequent measurements are taken at locations 1862, 1864, 1866, and 1868 in the order indicated by path 1880. The perfusion value produced at location 1864 is slightly higher than the perfusion values produced at locations 1862 and 1866, indicating that location 1864 was partially within the area 1820 while locations 1862 and 1866 were fully within the lesser-damaged area 1810. The boundary can be approximated by interpolating between the various measurement locations. For example, the perfusion value produced at location 1870 is high enough to suggest that it is fully within the area 1820 and therefore does not help identify the boundary between areas 1810 and 1820. The subsequent location 1872 is therefore directly away from the starting location 1860. As location 1860, in this example, is now fully within area 1810, the boundary between areas 1810 and 1820 can be interpolated to be between locations 1870 and 1872. The perfusion value produced from a measurement at location 1874 is similar to the perfusion value from location 1870 and it can be sufficient to identify the boundary as outside the location 1874 without taking another measurement at a location corresponding to location 1872.

This set of measurements enable the creation of a map of a certain level of damage, for example the area 1820. Repeating this mapping process at regular time intervals would provide an indication of whether the area 1820 is growing, which may indicate that an increased level of intervention is appropriate, or shrinking, which may indicate that the current level of intervention is allowing the damage to heal.

Example 8: Treatment Decision Pathway for Stratifying Patients and Providing Appropriate Treatments FIG. 19A outlines a currently recommended treatment decision pathway for preventing pressure ulcers in hospital patients as presented by The National Institute for Health and Care Excellence (NICE) in their clinical guideline *Pressure ulcers: prevention and management*, published 23 Apr. 2014. The guidelines recommend that a risk analysis be performed for every patient admitted to a care facility that exhibits one or more risk factors such as significantly limited mobility, a significant loss of sensation, a previous or current pressure ulcer, a nutritional deficiency, an inability to reposition themselves, or a significant cognitive impairment. Risk assessment is commonly done using a scored checklist, such as the Braden Scale, that assesses the severity of specific risk factors.

Upon completion of the risk assessment, the patient is identified as (i) having a low risk of developing a pressure ulcer, (ii) being at risk of developing a pressure ulcer, or (iii) being at high risk of developing a pressure ulcer. Depending on the level of risk the patient is classified as having, the patient undergoes different sequences of treatment and evaluation by visual assessment.

All patients are potentially at risk of developing a pressure ulcer. They are more likely to occur in people who are seriously ill or have a neurological condition, impaired mobility, impaired nutrition, poor posture, or a deformity.

Pressure ulcers are categorized as stage-1 through stage-4, with stage-1 being the lowest condition. The National Pressure Ulcer Advisory Panel (NPUAP) has defined a "stage-1" ulcer as intact skin with a localized area of non-blanchable erythema, where "blanchable" indicates that the tissue loses all redness when pressed and "non-blanchable" tissue remains red when pressed due to the presence of red blood cells outside of blood vessels (extravasation). In some patients, blanchable erythema or changes in sensation, temperature, or firmness may precede visual changes.

Visual skin assessment (VSA) is the current method of identifying a pressure ulcer. A trained healthcare professional assesses the appearance of the skin, visually and tactilely, looking for redness or variations in tissue firmness, tissue temperature, or moisture.

If a patient is identified as having a low risk of developing a pressure ulcer, the patient is simply monitored for a change in clinical status such as undergoing surgery, worsening of an underlying condition, or a change in mobility. A patient who uses a wheelchair or sits for prolonged periods may be provided with a high-specification foam cushion or equivalent pressure-distributing cushion. If there is no change in clinical status, a low-risk patient will not be reassessed under this set of guidelines and stays within the same treatment and evaluation pathway until he or she is discharged from the care facility.

If a patient is identified as being at risk of developing a pressure ulcer, the patient will be scheduled to be turned, or "rounded," every 6 hours. As with the low-risk patient, a high-spec foam cushion may be provided if the patient uses a wheelchair or sits for prolonged periods of time. No other monitoring or intervention is recommended by the NICE guidelines.

A high-risk patient receives a high-spec foam mattress as a preventative measure, provided with a high-spec cushion if they are in a wheelchair or sit for prolonged periods of time, and will be turned every 4 hours. The patient will receive a daily VSA for all areas of the body. If an area is found to have non-blanchable erythema, an appropriate intervention will be implemented and that area re-checked by VSA every 2 hours. Areas that do not exhibit non-blanchable erythema are re-checked daily by VSA. A personalized care plan will be developed for each high-risk patient.

It can be seen from this flow chart that the majority of the time spent by caregivers will be on the high-risk patients. While this may be appropriate, it leaves the at-risk patients unmonitored and they may develop a stage-1 ulcer before the condition is observed by a caregiver. Furthermore, the consequence of relying on VSA to detect a problem necessarily means that patients will develop a stage-1 ulcer before an intervention is selected or implemented. By the time that the damage has progressed to stage-1, it is likely that the skin will break and become a stage-2 ulcer despite intervention. There is a clear need to identify tissue damage earlier so that interventions can prevent progression of the subepidermal damage to stage-1 and beyond.

Figure 19A:
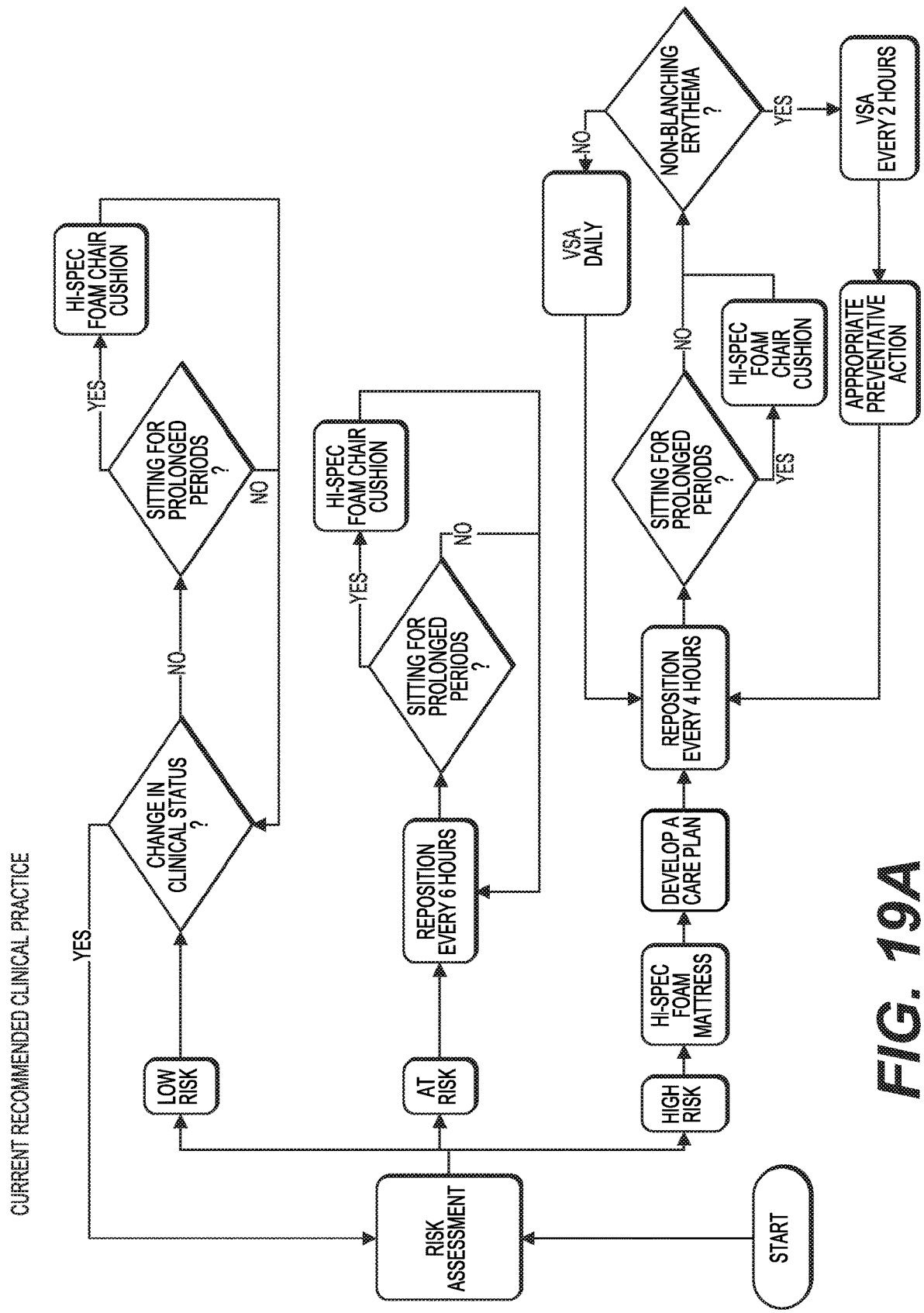
FIG. 19A is an example of a currently recommended treatment decision pathway for preventing pressure ulcers in hospital patients using a combination of risk assessment and visual assessment.
Figure 19B:
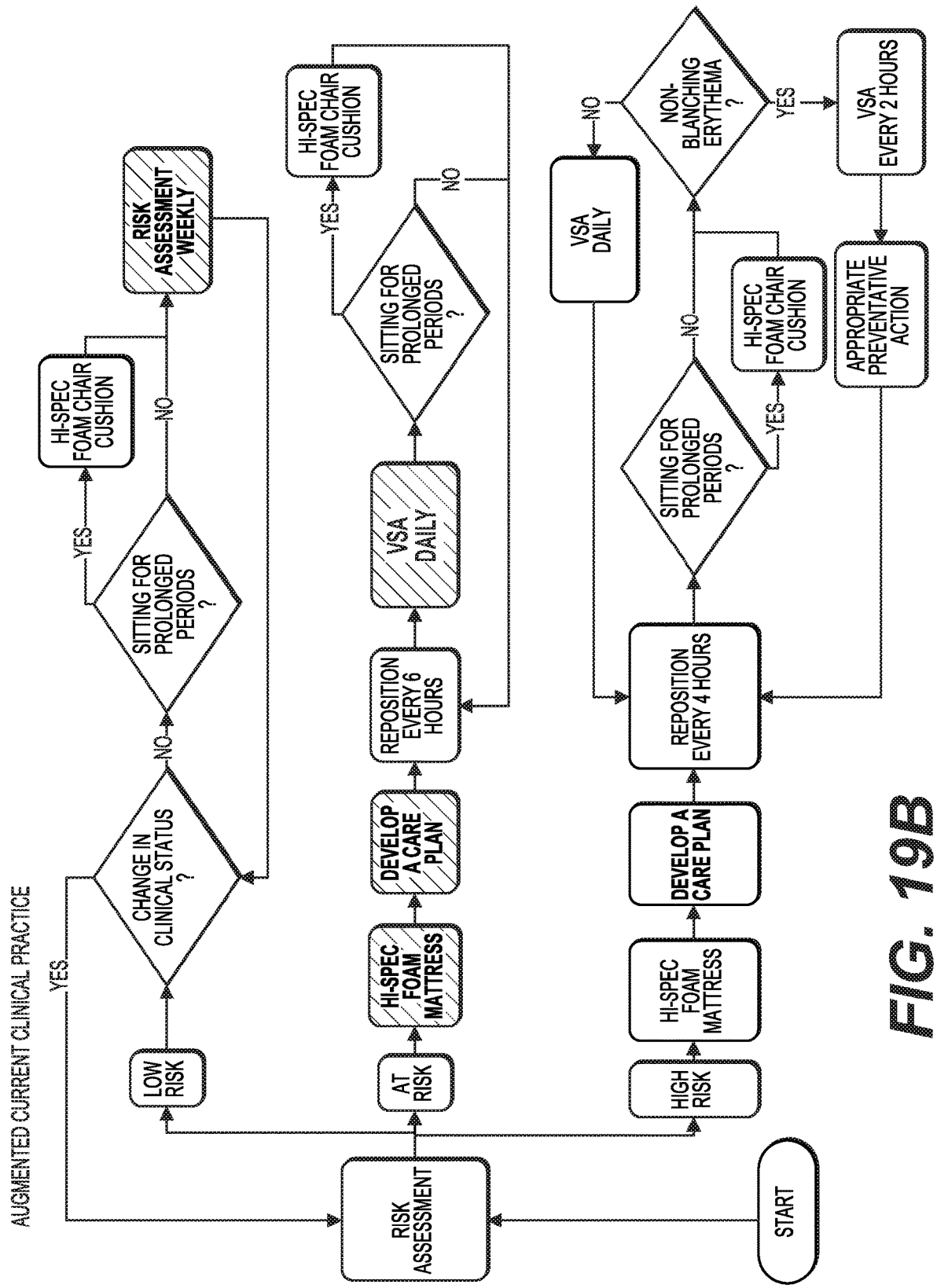
FIG. 19B is an example of a current augmented treatment decision pathway for preventing pressure ulcers as currently implemented at some health care facilities.

FIG. 19B is an example of a current augmented treatment decision pathway for preventing pressure ulcers as currently implemented at some health care facilities. The augmented pathway adds monitoring steps to both the at-risk and the low-risk paths. A low-risk patient received a weekly risk assessment, for example completion of the Braden Scale assessment. A patient identified as at-risk in the initial assessment will receive a high-spec foam mattress as a preventative measure and will be evaluated daily by VSA. A care plan will be developed for the monitoring and treatment of the at-risk patient. No change is made in the care if a high-risk patient.

The augmented plan has the benefit of providing basic monitoring of all patients for pressure ulcers. The additional steps require additional time, however, either by adding staff or further burdening the existing staff. While superior to the recommended care pathway of FIG. 19A, the care pathway of FIG. 19B requires more resources and still suffers from the limitation that a patient must develop a stage-1 ulcer before VSA identifies the damage.

Various hospitals and care facilities use different numbers of risk categories, ranging from two categories, low-risk and at-risk, to four or more categories, adding categories such as "very-high-risk" to the categories of the example of FIG. 19B. Patients are assigned to the various categories based on the results of the initial risk assessment.

Figure 20:
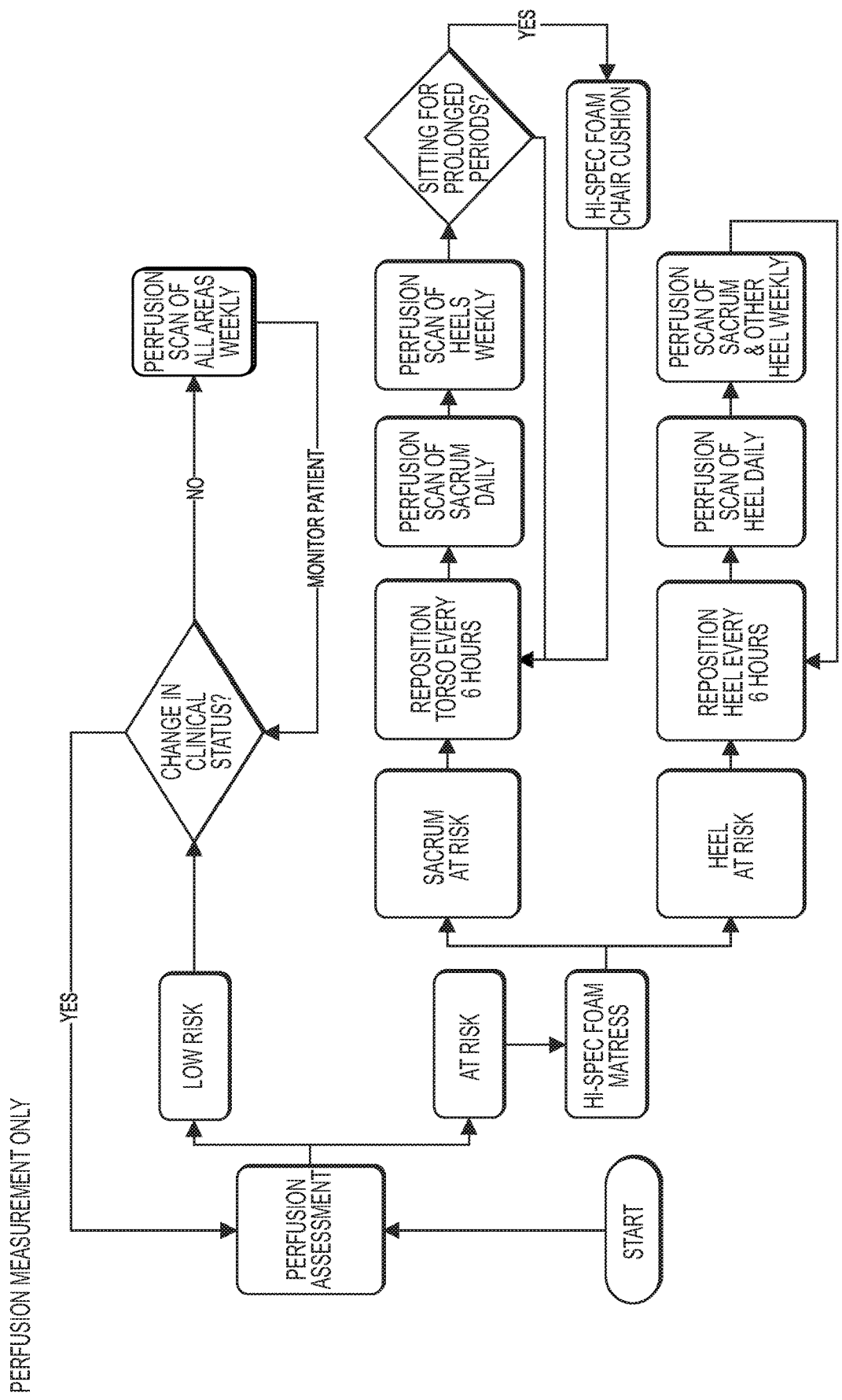
FIG. 20 is an example flowchart of how an apparatus for assessing perfusion of blood in tissue below a patient's skin may be used in a stand-alone process to prevent pressure ulcers, in accordance with the present disclosure.

FIG. 20 is an example flowchart of how an apparatus of for assessing perfusion of blood in tissue below a patient's skin may be used in a stand-alone process to prevent pressure ulcers, in accordance with the present disclosure. Every incoming patient receives a complete perfusion assessment of all body locations that are selected for monitoring. These selected locations may include areas recommended in the Instructions For Use (IFU) of the perfusion measurement apparatus, such as the sacrum and the heels. Additional locations may be identified by the hospital and integrated into their in-house practice. Multiple perfusion measurements are taken at and around each body location at positions that are separated from each other, although this is generally referred to as taking multiple measurements at the body location. The perfusion measurement apparatus calculates a "delta" value for each location from the set of measurements taken at and around that location. The delta value is then compared to one or more threshold values to categorize a patient. In this example, the patient is assigned to one of two risk categories: low-risk and at-risk.

In an aspect, the clinician will take perfusion measurements of a body location identified as having possible damage in the initial set of perfusion measurements at a first time interval. The clinician will also take perfusion measurements of all other body locations selected for monitoring at a second time interval that is longer than the first time interval. In an aspect, the values of the first and second time intervals are different depending on the risk category to which the patient has been assigned. For example, a high-risk patient will have a first time interval of 4 hours and a second time interval of 1 day while an at-risk patient will have a first time interval of 1 day and a second time interval of 1 week. In an aspect, the time interval may be event-based, for example upon a change of attending staff or shift change, rather than strictly based on time. In general, body locations that have elevated delta values are scanned more often than other body locations that are monitored but having normal delta values in previous perfusion measurements.

In an aspect, the interval at which perfusion measurements are performed is determined by the delta values from the prior perfusion measurements. For example, a perfusion measurement of a body location that had a delta value greater than or equal to a first threshold in a previous perfusion scan is performed at a first time interval, while a perfusion measurement is performed at a second time interval that is shorter than the first time interval when the prior perfusion measurement of a body location had a delta value greater than or equal to a second threshold that is higher than the first threshold.

In this example, low-risk patients receive a weekly perfusion scan of all body locations that are selected for monitoring. This is a small effort that provides basic protection for even the healthiest patients, as a weekly perfusion scan is likely to detect tissue damage before it becomes visible to VSA.

At-risk patients, which will include patients that would be identified as high-risk in the current care pathways of FIGS. 19A and 19B, will receive specialized care based on the body location that exhibits a delta value above a threshold. For example, if the sacrum body location has a delta value above a threshold, the patient will be repositioned every 6 hours and receive perfusion measurements of the sacrum every day and perfusion measurements of the other body locations every week.

Figure 21:
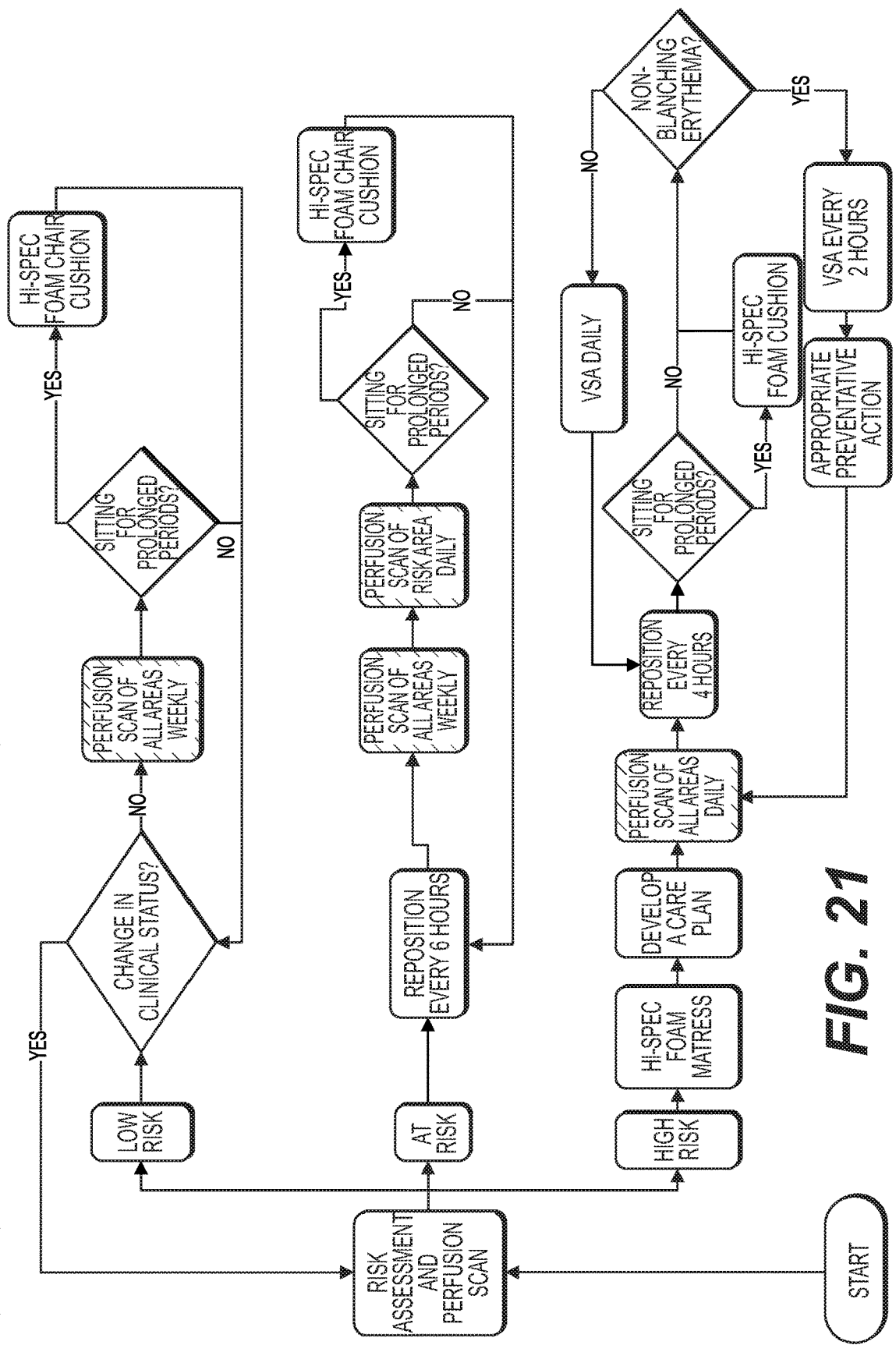
FIG. 21 is an example flowchart of how an apparatus for assessing perfusion of blood in tissue below a patient's skin may be used as an adjunct to further improve the augmented treatment decision pathway of FIG. 19B, in accordance with the present disclosure.

FIG. 21 is an example flowchart of how an apparatus of for assessing perfusion of blood in tissue below a patient's skin may be used as an adjunct to further improve the augmented treatment decision pathway of FIG. 19B, in accordance with the present disclosure. An incoming patient receives both a risk assessment and a perfusion scan of all body locations identified by the hospital for monitoring and the assignment of a patient to a risk category is based partially on the risk assessment and partially on the perfusion scan results. An initial delta value that is greater than a threshold is an indication that there is possible damage at that body location. In an aspect, the assignment is based solely on the largest initial delta value found during the initial perfusion scan.

A decision whether to implement an intervention, for example turning the patient at a first interval, is currently based on the VSA and risk assessment despite the uncertainty of whether there is early stage damage below the skin. In an aspect, the decision to implement an intervention for a particular body site, or a general intervention such as a high-spec mattress, is based on the delta value found for that site in the perfusion scan. If the delta value is less than a predetermined threshold, no intervention is required. If the delta value is greater than the predetermined threshold, then an intervention is selected and implemented based partially on the body location and partially on the delta value for that body location. The predetermined threshold for whether or not to select and implement an intervention may be higher or lower than the threshold for determination that there is possible damage at the body location.

A comparison of the costs of provided the care pathways of FIGS. 19A, 19B, 20, and 21 reveals one of the benefits of utilizing a perfusion measurement apparatus to monitor patients. Note that the costs cited herein are for patients who do not have or develop pressure ulcers, in which case the estimated treatment cost jumps to $2000 for a stage-1 ulcer.

The baseline for this comparison is the augmented current practice of FIG. 19B, which represents a current "best practice" for hospitals striving to reduce the incidence rate of pressure ulcers. Providing the care of the low-risk care pathway is expected to cost an average of $26 per patient for the average hospital stay of 5.6 days, the care for an at-risk patient is estimated to cost an average of $121, and a high-risk patient is expected to cost $165. All of the care pathways rely on a VSA to detect a pressure ulcer and are otherwise implementing interventions based on "typical" patient progression rather than the particular patient's condition.

Integrating a perfusion measurement apparatus into the current "best practice" workflow, as shown in FIG. 21, does not lower the cost of any of the care pathways as no work element is being eliminated. The benefit is in the ability to detect tissue damage at an earlier stage at a minimal incremental cost. The incremental cost of adding a perfusion scan to the no-risk care pathway is $2, raising the cost from approximately $26 to $28. The expected cost of caring for an at-risk patient who does not have any elevated perfusion delta values, i.e. does not have subepidermal tissue damage, is also increased by only $2. If an at-risk patient is found to have an elevated perfusion delta value, however, the patient is escalated to the high-risk category, where the expected cost of care increases from $165 to $169. While this may seem like a small additional cost at first glance, it represents an increase in the level of protection provided to at-risk patients.

FIG. 20 represents an example workflow that relies solely on a perfusion measurement apparatus to monitor patients value obtained from another body part of the same patient that is not experiencing external pressure or mechanical forces. The resulting perfusion delta values in a single day are averaged and plotted for each patient.

Figure 28:
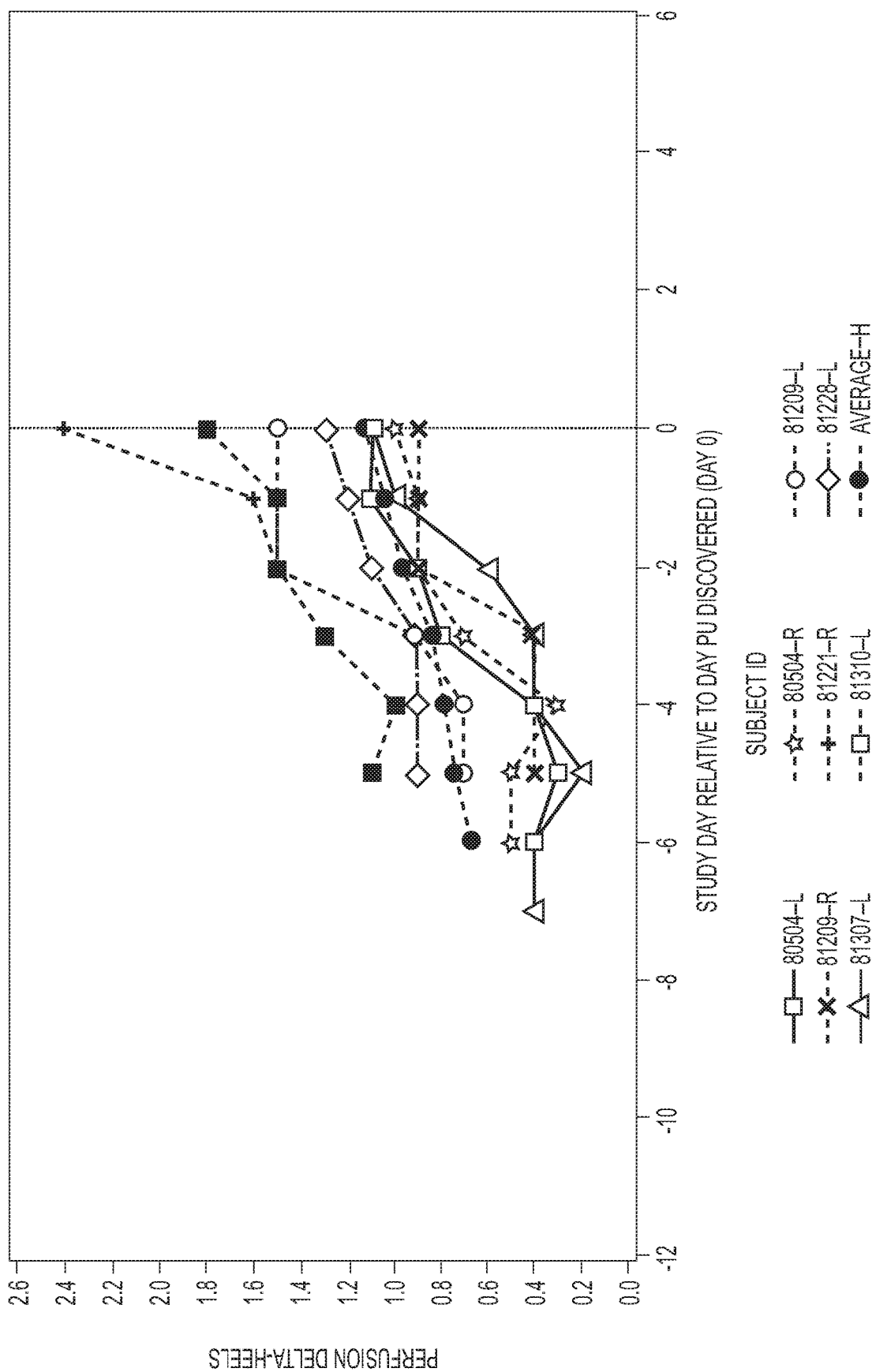
FIG. 28 depicts example perfusion delta values over time for patients that develop pressure ulcers in the heels, in accordance with the present disclosure.
Figure 29A:
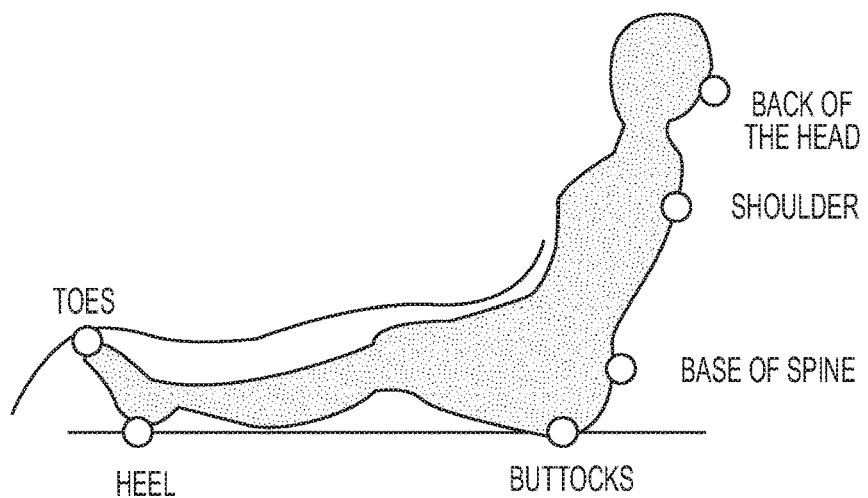
FIGS. 29A, 29B, 29C, and 29D illustrate various pressure points on a patient's body at different positions.
Figure 29B:
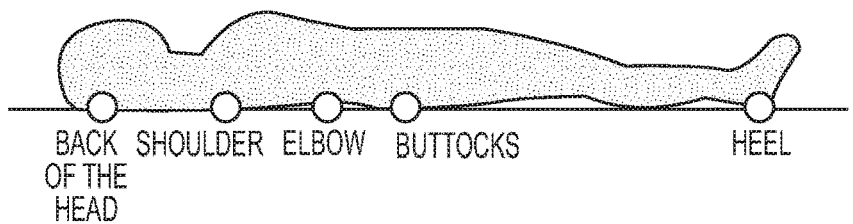
Figure 29C:
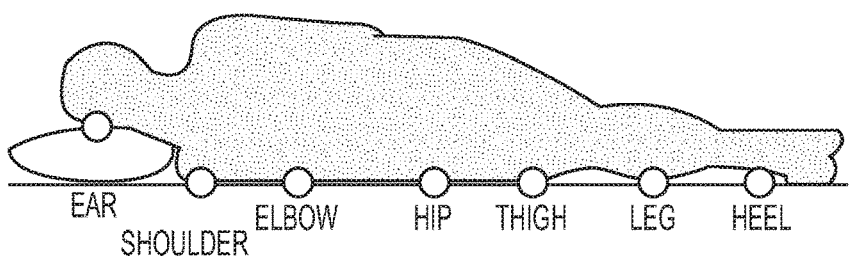
Figure 29D:
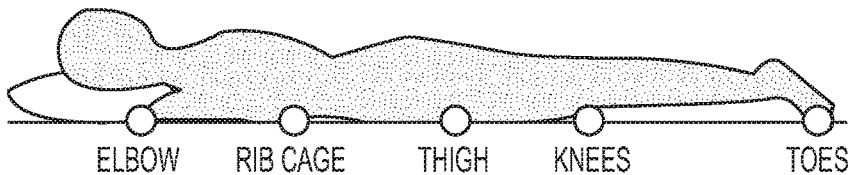

FIG. 28 illustrates trends of perfusion delta values for seven (7) patients prior to a pressure ulcer diagnosis at one or both of their heels. Trends across different patients are time-shifted to align to Day 0 as the pressure ulcer diagnosis event. A reference perfusion delta curve ("AVERAGE-H") is generated by averaging the perfusion delta values trends of all patients (n=20) that are eventually visually diagnosed with a heel pressure ulcer. As shown in FIG. 28, the perfusion delta values of these seven patients exhibit a spike in magnitude two (−2) to four (−4) days prior to the visual diagnosis compared to the reference curve. For these patients, a steeper slope of the perfusion delta value trend compared to the reference curve is indicative of early onset of a pressure ulcer before any visual detection.

Example 10: Intervention Levels Based on Oxygenation Measurements

Subjects identified as being at risk for pressure ulcers are treated in accordance with the following scheme:

TABLE 3

EXAMPLE INTERVENTION SCHEME FOR TREATING A PATIENT AT RISK FOR PRESSURE ULCER

| Risk Level | Intervention | Frequency of Subsequent Oxygenation Monitoring | Corresponding $SpO_2$ Ranges |
|---|---|---|---|
| 0 | provide good nutrition, standard mattress, and/or turn every 24 hours | every 24 hours | $SpO_2 \geq 95\%$ |
| 1 | provide a heel boot; apply dressing to back or sides of anatomic sites at risk; change of support surfaces; turn patient at a shorter interval | every 4 hours | $85\% \leq SpO_2 < 95\%$ |
| 2 | provide a low-friction padded mattress surface; keep patient's body dry; turn every 1-2 hours | every 1 hour | $SpO_2 < 85\%$ | and forgoes the routine VSA. The expected cost of preventative care for a low-risk patient is $4, compared to the $28 cost for the integrated low-risk care pathway of FIG. 21. For an at-risk patient, which is the only other category for the perfusion measurement apparatus care pathway of FIG. 20, the expected cost is $97, compared to the $123-$169 costs for the at-risk and high-risk patients of the integrated care pathway of FIG. 21.

Example 9: Perfusion Delta Trends in Heels of Patients is Indicative of Pressure Ulcer Onset Perfusion measurements are taken over time at the heels of patients using an apparatus according to the present disclosure, prior to any visual diagnosis of pressure ulcers at the heel. At each time point, each of the patients is directed to have toes pointed away from the body and rotated outwards toward the lateral side of the body. A receiver of the perfusion detection apparatus is placed on the medial side of the heel. The receiver is adjusted for full contact with the heel, and multiple measurements are taken around the back of the heel in a curve. Each of the reflected light measurements is converted to a perfusion delta value by subtracting from the measurement a reference perfusion From the foregoing, it will be appreciated that the present invention can be embodied in various ways, which include but are not limited to the following:

Embodiment 1. An apparatus for assessing perfusion of blood in tissue below a patient's skin, comprising: an emitter configured to emit light at a first wavelength and a second wavelength when activated, a first receiver configured to measure a first intensity of received light at the first wavelength and a second intensity of received light at the second wavelength and provide a first signal comprising information about the first and second intensities of the received light, a substrate coupled to the emitter and the first receiver and configured such that the emitter and first receiver can be placed in simultaneous contact with the patient's skin, and a processor coupled to the first receiver and configured to: receive the first signal, determine a first summation value of the first and second intensities of the received light, and determine a level of perfusion of the tissue from the first summation value.

Embodiment 2. The apparatus of embodiment 1, wherein the first receiver is spaced apart from the emitter by a first distance selected so that the light emitted by the emitter and received by the first receiver is reflected from a first depth below the patient's skin.

Embodiment 3. The apparatus of embodiment 1 or 2, further comprising a second receiver, wherein: the second receiver is spaced apart from the emitter by a second distance selected so that the light emitted by the emitter and received by the second receiver is reflected from a second depth below the patient's skin, the second receiver is configured to: measure a third intensity of received light at the first wavelength, measure a fourth intensity of received light at the second wavelength, and provide a second signal comprising information about the third and fourth intensities of the received light, and the processor is coupled to the second receiver and configured to: receive the second signal, determine a fifth intensity of the received light by subtracting the third intensity from the first intensity, determine a sixth intensity of the received light by subtracting the fourth intensity from the second intensity, determine a second summation value of the fifth and sixth intensities, and determine a level of perfusion of the tissue between the first depth and the second depth based on the second summation value.

Embodiment 4. The apparatus of any one of embodiments 1 to 3, wherein the first wavelength is associated with a peak absorption wavelength of oxygenated hemoglobin and the second wavelength is associated with a peak absorption wavelength of de-oxygenated hemoglobin.

Embodiment 5. The apparatus of any one of embodiments 1 to 4, wherein the emitter comprises a first source that emits light at the first wavelength and a second source that emits light at the second wavelength.

Embodiment 6. The apparatus of embodiment 5, wherein the first source and second source can be individually activated.

Embodiment 7. The apparatus of any one of embodiments 1 to 6, wherein the receiver comprises a first detector that senses light at the first wavelength and a second detector that senses light at the second wavelength.

Embodiment 8. The apparatus of embodiment 7, wherein: the processor is individually coupled to each of the first detector and the second detector, and the first signal comprises individual signals from the first and second detectors.

Embodiment 9. The apparatus of any one of embodiments 1 to 8, wherein: the processor is coupled to the emitter, the emitter is configured to emit light upon receipt of a strobe pulse, the processor is configured to provide the strobe pulse to the emitter and to the first receiver, the first receiver is further configured to measure a first time period between receipt of the strobe pulse and receipt of light from the emitter, and the first signal comprises information about the first time period.

Embodiment 10. The apparatus of any one of embodiments 1 to 9, further comprising a memory coupled to the processor, wherein the processor is configured to store in the memory a series of summation values associated with sequential activations of the emitter.

Embodiment 11. The apparatus of embodiment 10, wherein the processor is further configured to determine a range between a smallest summation value and a largest summation value of the series of summation values.

Embodiment 12. The apparatus of embodiment 10, wherein the processor is further configured to determine a percentage value for each summation value relative to a largest summation value in the series of summation values.

Embodiment 13. The apparatus of any one of embodiments 1 to 12, further comprising an accelerometer that is configured to provide a third signal comprising information regarding the acceleration of the apparatus in three spatial dimensions, wherein: the processor is coupled to the accelerometer and configured to receive the third signal, and the processor is further configured to determine a spatial position of the emitter when the emitter is activated.

Embodiment 14. A method of assessing perfusion of blood in tissue below a patient's skin, the method comprising the steps of: emitting light into the patient's skin at a first location on the patient's skin, the light comprising a first wavelength and a second wavelength, receiving a portion of the emitted light that has been reflected from the tissue, measuring a first intensity of received light at the first wavelength and a second intensity of received light at the second wavelength, determining a first summation value of the first and second intensities of the received light.

Embodiment 15. The method of embodiment 14, further comprising the steps of: repeating the steps of emitting light, receiving a portion of the emitted light, and measuring the first and second intensities of the received light at a second location on the patient's skin, determining a second summation value of the first and second intensities of the received light associated with the second location, and determining a delta value between the first summation value and the second summation value.

Embodiment 16. The method of embodiment 14, further comprising the steps of: repeating the steps of emitting light, receiving a portion of the emitted light, and measuring the first and second intensities of the received light at a plurality of locations on the patient's skin, determining a plurality of summation values of the first and second intensities of the received light associated with the respective plurality of locations, identifying a largest summation value from the plurality of summation values, and determining a delta value between the largest summation value and at least one of the plurality of summation values.

Embodiment 17. An apparatus for assessing perfusion of blood in tissue below a patient's skin, comprising: an emitter configured to selectably emit light at a first wavelength or emit light at a second wavelength, a camera configured to form a first image of reflected light at the first wavelength and a second image of reflected light at the second wavelength, a substrate coupled to the emitter and the camera and configured such that substrate can be placed such that the light emitted by the emitter illuminates a portion of the skin of the patient that is within a field of view of the camera, a display, and a processor coupled to the camera and the display and configured to: receive the first and second images, form a third image that is a summation of the first and second images, and provide the third image on the display.

Embodiment 18. The apparatus of embodiment 17, wherein: the processor is coupled to the emitter, the processor is further configured to cause the emitter to emit only light at the first wavelength at a first time and emit only light at the second wavelength at a second time, and the camera forms the first image at the first time and forms the second image at the second time.

Embodiment 19. A method of identifying and treating a patient in need of wound treatment, the method comprising the steps of: evaluating a patient for a risk of tissue damage in a patient upon admission to a care facility, where the evaluating comprises making a first plurality of perfusion measurements in the patient, calculating a first delta value from a portion of the first plurality of perfusion measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater.

Embodiment 20. The method of embodiment 19, where the step of making a first plurality of perfusion measurements comprises using a perfusion measurement apparatus to make each perfusion measurement and produce a respective perfusion value, and the step of calculating the first delta value comprises comparing the perfusion values produced by a portion of the first plurality of perfusion measurements.

Embodiment 21. The method of embodiment 19, where the step of making a first plurality of perfusion measurements comprises making a first sub-set of perfusion measurements at the first location and at least one additional sub-set of perfusion measurements at a second location, the step of calculating a first delta value comprises calculating a first-location first delta value from a portion of the first sub-set of measurements and calculating a second-location first delta value from a portion of the second sub-set of measurements, the step of determining whether the first delta value exceeds a first threshold comprises determining whether the first-location first delta value exceeds a first-location first threshold and determining whether the second-location first delta value exceeds a second-location first threshold, the step of administering a first intervention of level-0 comprises administering a first-location-specific level-0 intervention if the first-location first delta does not exceed the first-location first threshold and administering a second-location-specific level-0 intervention if the second-location first delta does not exceed the second-location first threshold, and the step of administering a first intervention of level-N comprises administering a first-location-specific level-N intervention if the first-location first delta exceeds the first-location first threshold and administering a second-location-specific level-N intervention if the second-location first delta exceeds the second-location first threshold.

Embodiment 22. The method of embodiment 19, where the evaluating step further comprises performing a visual assessment.

Embodiment 23. The method of embodiment 22, where the patient has no visible symptom of a wound.

Embodiment 24. The method of embodiment 19, where the evaluating step further comprises performing a risk assessment.

Embodiment 25. The method of embodiment 19, where N has a value equal to 1.

Embodiment 26. The method of embodiment 19, where the value of N is 2 or greater based on an amount by which the first delta value exceeds the first threshold.

Embodiment 27. The method of embodiment 19, where N has a value not exceeding 10.

Embodiment 28. The method of embodiment 19, where the first intervention of level-N is an intervention that is more intensive than the first intervention of level-0.

Embodiment 29. The method of embodiment 19, further comprising the steps of: making a second plurality of perfusion measurements in the patient at a first pre-determined frequency corresponding to the administered intervention level, calculating a second delta value from a portion of the second plurality of perfusion measurements, determining whether the second delta value exceeds a second threshold, continuing to administer the first intervention if the second delta value does not exceed the second threshold, continuing to make a plurality of perfusion measurements at the first pre-determined frequency if the second delta value does not exceed the second threshold, administering a second intervention of level-M if the second delta value exceeds the second threshold, where M is an integer and M is greater than N, and making a plurality of perfusion measurements at a second pre-determined frequency corresponding to level-M if the second delta value exceeds the second threshold.

Embodiment 30. The method of embodiment 29, where the second threshold is the same as the first threshold.

Embodiment 31. The method of embodiment 29, where the second threshold is greater than the first threshold.

Embodiment 32. The method of embodiment 29, where M has a value equal to N+1, but not exceeding 10.

Embodiment 33. The method of embodiment 29, where the value of M is proportional to an amount by which the second delta value exceeds the second threshold.

Embodiment 34. The method of embodiment 29, further comprising the steps of: determining whether the second delta value is less than a third threshold, administering a level-(N−1) intervention if the second delta value is less than the third threshold and if the first intervention is not of level-0, and making a plurality of perfusion measurements at a pre-determined frequency corresponding to level-(N−1) if the second delta value is less than the third threshold.

Embodiment 35. The method of embodiment 19, where a level-0 intervention is selected from the group consisting of providing good nutrition, standard mattress, turning every 24 hours, and a combination thereof.

Embodiment 36. The method of embodiment 19, where the first delta value exceeding the first threshold is calculated from the portion of the first plurality of perfusion measurements taken at the patient's heel.

Embodiment 37. The method of embodiment 36, where a level-1 intervention is providing a heel boot to the patient.

Embodiment 38. The method of embodiment 36, where a level-2 intervention is changing the patient's support surface.

Embodiment 39. The method of embodiment 36, where a level-3 intervention is applying dressing to the back or sides of patient's heel.

Embodiment 40. The method of embodiment 36, where a level-4 intervention is changing the patient's sheet cover to a low-friction sheet cover.

Embodiment 41. The method of embodiment 36, where a level-5 intervention is providing a low-friction padded mattress surface for the patient's lower leg.

Embodiment 42. The method of embodiment 36, where a level-6 intervention is turning the patient at a shorter interval than currently provided for.

Embodiment 43. The method of embodiment 36, where a level-7 intervention is applying a barrier cream to the patient's heel.

Embodiment 44. The method of embodiment 36, where a level-8 intervention is applying a neuro-muscular stimulation to the patient's heel.

Embodiment 45. The method of embodiment 36, where a level-9 intervention is applying a topical cream to the patient's heel to enhance perfusion.

Embodiment 46. The method of embodiment 36, where a level-10 intervention is providing a silicon pad for the patient's lower leg.

Embodiment 47. The method of embodiment 19, where the first delta value exceeding the first threshold is calculated from the portion of the first plurality of perfusion measurements taken at the patient's sacrum.

Embodiment 48. The method of embodiment 47, where a level-1 intervention is selected from the group consisting of repositioning the patient with a wedge, keeping the patient's sacrum dry, and a combination thereof.

Embodiment 49. The method of embodiment 47, where a level-2 intervention is changing the patient's mattress to a pressure-alleviating mattress.

Embodiment 50. The method of embodiment 47, where a level-3 intervention is applying a dressing over the patient's sacrum.

Embodiment 51. The method of embodiment 47, where a level-4 intervention is changing the patient's mattress to a dynamic mattress.

Embodiment 52. The method of embodiment 47, where a level-5 intervention is applying a barrier cream to the patient's sacrum.

Embodiment 53. The method of embodiment 47, where a level-6 intervention is applying a neuro-muscular stimulation to the patient's sacrum.

Embodiment 54. The method of embodiment 47, where a level-7 intervention is applying a topical cream to the patient's sacrum to enhance perfusion.

Embodiment 55. The method of embodiment 47, where a level-8 intervention is providing a silicone pad under the patient's body.

Embodiment 56. The method of embodiment 19, where a level-0 pre-determined frequency is every 24 hours.

Embodiment 57. The method of embodiment 19, where a level-1 pre-determined frequency is every 10 hours.

Embodiment 58. The method of embodiment 19, where a level-2 pre-determined frequency is at the beginning of each nursing shift.

Embodiment 59. The method of embodiment 19, where a level-3 pre-determined frequency is every 12 hours.

Embodiment 60. The method of embodiment 19, where a level-4 pre-determined frequency is every 8 hours.

Embodiment 61. The method of embodiment 19, where a level-5 pre-determined frequency is every 6 hours.

Embodiment 62. The method of embodiment 19, where a level-6 pre-determined frequency is every 4 hours.

Embodiment 63. The method of embodiment 19, where a level-7 pre-determined frequency is every 2 hours.

Embodiment 64. The method of embodiment 19, where a level-8 pre-determined frequency is every 1 hour.

Embodiment 65. The method of embodiment 19, where a level-9 pre-determined frequency is every 0.5 hour.

Embodiment 66. A method of slowing the progression of skin and tissue damage in a patient in need thereof, the method comprising the steps of: identifying a current intervention of level-K received by the patient, making a plurality of perfusion measurements in the patient, calculating a delta value from a portion of the plurality of perfusion measurements, determining whether the delta value exceeds a first threshold, continuing to administer the current intervention if the delta value does not exceed the first threshold, continuing to make a plurality of perfusion measurements at a pre-determined frequency corresponding to level-K if the delta value does not exceed the first threshold, administering a new intervention of level-N if the delta value exceeds the first threshold, where N has a value greater than K, and making a plurality of perfusion measurements at a pre-determined frequency corresponding to level-N if the delta value exceeds the first threshold.

Embodiment 67. The method of embodiment 66, where N has a value equal to K+1, but not exceeding 10.

Embodiment 68. The method of embodiment 66, where the value of N is proportional to an amount by which the delta value exceeds the first threshold.

Embodiment 69. The method of embodiment 66, further comprising the steps of: determining whether the delta value is less than a second threshold, administering a level-L intervention if the delta value is less than the second threshold, where L has a non-negative value less than K, and making a plurality of perfusion measurements at a pre-determined frequency corresponding to level-L if the delta value is less than the second threshold.

Embodiment 70. The method of embodiment 69, where L has a value equal to L−1.

Embodiment 71. The method of embodiment 69, where the value of L is selected based on an amount by which the delta value is lower than the second threshold.

Embodiment 72. The method of embodiment 66, where the patient in need thereof is a patient experiencing a change of care.

Embodiment 73. The method of embodiment 66, where the patient in need thereof is a patient experiencing a change in mobility.

Embodiment 74. The method of embodiment 66, where the patient in need thereof is a patient experiencing a change in nutrition.

Embodiment 75. The method of embodiment 66, where the patient in need thereof is a patient experiencing a change in sensory perception.

Embodiment 76. The method of embodiment 66, where the patient in need thereof is a patient developing an open ulcer.

Embodiment 77. The method of embodiment 66, where the patient in need thereof is a patient recovering from an open ulcer.

Embodiment 78. The method of embodiment 66, where the patient in need thereof is a patient receiving surgery.

Embodiment 79. The method of embodiment 66, where the patient receives spinal analgesics during the surgery.

Embodiment 80. The method of embodiment 78, where the patient receives sacral analgesics during the surgery.

Embodiment 81. The method of embodiment 78, where the surgery has a duration of more than 4 hours.

Embodiment 82. A method of selecting a wound treatment for a patient, the method comprising the steps of: evaluating a patient for a risk of tissue damage in a patient upon admission to a care facility, where the evaluating step comprises making a first plurality of perfusion measurements in the patient, calculating a first delta value from a portion of the first plurality of perfusion measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater.

Embodiment 83. A method of stratifying groups of patients in a care facility based on risk of wound development, the method comprising the steps of: making a plurality of perfusion measurements in each of the patients, calculating a delta value from a portion of the plurality of perfusion measurements for each of the patients, determining whether each delta value exceeds any values in a set of threshold values corresponding to N care levels and assigning a care level to each of the patients, rearranging the group of patients based on each of the patient's assigned care levels.

Embodiment 84. A method of reducing incidence of wound development in patients admitted to a care facility, the method comprising the steps of: evaluating a patient for a risk of tissue damage upon admission to the care facility, where the evaluating step comprises making a first plurality of perfusion measurements in the patient, calculating a first delta value from a portion of the first plurality of perfusion measurements, determining whether the first delta value exceeds a first threshold, administering a first intervention of level-0 if the first delta value does not exceed the first threshold, and administering a first intervention of level-N if the first delta value exceeds the first threshold, where N is an integer and N has a value of 1 or greater.

Embodiment 85. The method of embodiment 84, where the incidence of wound development in patients in the care facility is reduced to 1 in 100.

Embodiment 86. A method of identifying and treating a patient in need of application of a barrier cream to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a barrier cream to the patient's heel if the delta value exceeds the threshold, and making a plurality of perfusion measurements every two hours if the delta value exceeds the threshold.

Embodiment 87. A method of identifying and treating a patient in need of application of a neuro-muscular stimulation to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a neuro-muscular stimulation to the patient's heel if the delta value exceeds the threshold, and making a plurality of perfusion measurements every hour if the delta value exceeds the threshold.

Embodiment 88. A method of identifying and treating a patient in need of application of a topical cream to the patient's heel, the method comprising the steps of: making a plurality of perfusion measurements at the patient's heel, calculating a delta value from a portion of the plurality of perfusion measurements, determining whether the delta value exceeds a threshold corresponding to level N, where N is greater than or equal to 2, administering a topical cream to the patient's heel if the delta value exceeds the threshold, and making a plurality of perfusion measurements every half an hour if the delta value exceeds the threshold.

Embodiment 89. A method of identifying and treating a patient in need of application of a barrier cream to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a barrier cream to the patient's sacrum if the delta value exceeds the threshold, and making a plurality of perfusion measurements every six hours if the delta value exceeds the threshold.

Embodiment 90. A method of identifying and treating a patient in need of application of a neuro-muscular stimulation to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a neuro-muscular stimulation to the patient's sacrum if the delta value exceeds the threshold, and making a plurality of perfusion measurements every four hours if the delta value exceeds the threshold.

Embodiment 91. A method of identifying and treating a patient in need of application of a topical cream to the patient's sacrum, the method comprising the steps of: making a plurality of perfusion measurements at the patient's sacrum, calculating a delta value from a portion of the plurality of perfusion measurements, determining whether the delta value exceeds a threshold corresponding to level N, where N is greater than or equal to 2, administering a topical cream to the patient's sacrum if the delta value exceeds the threshold, and making a plurality of perfusion measurements every two hours if the delta value exceeds the threshold.

Embodiment 92. An apparatus for identifying damaged tissue, the apparatus comprising: an emitter and two receivers, where each of the emitter and two receivers is configured to be placed against a patient's skin, a processor electronically coupled to the receivers and configured to receive the information from a receiver and convert the information into a perfusion value, and a non-transitory computer-readable medium electronically coupled to the processor and comprising instructions stored thereon that, when executed on the processor, perform the step of: determining a difference between a first perfusion value corresponding to reflected light as measured by the first receiver at a first location on the patient's skin and a second perfusion value corresponding to reflected light as measured by the second receiver at a second location on the patient's skin, where the second location is bisymmetric relative to the first location.

Embodiment 93. The apparatus according to embodiment 92, where the difference being greater than a predetermined threshold is indicative of damaged tissue at one of the first and second locations.

Embodiment 94. The apparatus according to embodiment 93, further comprising: a substrate configured to be placed in a known position on the patient's skin, and the first and second receivers are disposed on the substrate such that the first and second receivers are positioned at bisymmetric locations on the patient's skin when the substrate is placed in the known position on the patient's skin.

Embodiment 95. The apparatus according to embodiment 92, further comprising a gap between the first and second receivers.

Embodiment 96. An apparatus for identifying damaged tissue, the apparatus comprising: a substrate configured to be placed against a surface of a patient's skin, a plurality of emitters that are disposed on the substrate at a respective plurality of positions and a plurality of receivers that are disposed on the substrate at a respective plurality of positions, where each receiver is configured to measure the reflected light and provide information regarding blood perfusion, a processor electronically coupled to the receivers and configured to receive the information regarding reflected light and convert the plurality of reflected light measurements into a respective plurality of perfusion values, and a non-transitory computer-readable medium electronically coupled to the processor and comprising instructions stored thereon that, when executed on the processor, perform the steps of: identifying from the plurality values a first receiver and a second receiver that are located at first and second positions that are bisymmetric with respect to the patient's skin, and comparing a first perfusion value that is associated with the first receiver with a second perfusion value that is associated with the second receiver.

Embodiment 97. The apparatus according to embodiment 96, where the instructions further comprise the steps of: determining a difference between the first and second perfusion values, and providing an indication that tissue is damaged at one of the first and second locations if the difference is greater than a predetermined threshold.

Embodiment 98. The apparatus according to embodiment 96, where the instructions further comprise the steps of: determining a difference between the first and second perfusion values, determining which of the first and second perfusion values is larger than the other, and providing an indication that tissue is damaged at the location associated with the larger perfusion value if the difference is greater than a predetermined threshold.

Embodiment 99. An apparatus for identifying damaged tissue, the apparatus comprising: an apparatus body; an emitter; a first receiver and a second receiver, where the two receivers are disposed on the apparatus body to allow simultaneous positioning of the first receiver on a first location on a patient's skin and the second receiver on a second location bisymmetric relative to the first location; a circuit electronically coupled to each of the two receivers and configured to measure the reflected light detected by each of the two receivers; a processor electronically coupled to the circuit that is configured to receive a first reflected light measurement from a first location and a second reflected light measurement from a second location, and to convert the first reflected light measurement to a first perfusion value and the second reflected light measurement to a second perfusion value; a non-transitory computer-readable medium electronically coupled to the processor and contains instructions that, when executed on the processor, perform the step of determining a difference between the first perfusion value and the second perfusion value.

Embodiment 100. The apparatus according to embodiment 99, where each of the two receivers are disposed on two ends of the apparatus body while being aligned on a common plane.

Embodiment 101. The apparatus according to embodiment 99, where the apparatus body is rigid and maintains the two receivers at a fixed separation distance and fixed orientation to each other.

Embodiment 102. The apparatus according to embodiment 99, where the apparatus body is flexible and allows the two receivers to be oriented at an angle to each other.

Embodiment 103. The apparatus according to embodiment 102, where the apparatus body comprises a hinge.

Embodiment 104. The apparatus according to embodiment 99, where the first reflected light measurement and the second reflected light measurement are measured simultaneously.

Embodiment 105. The apparatus according to embodiment 104, where the apparatus further comprises a contact sensor positioned proximate to one of the two receivers, and where the simultaneous measurements are triggered by the actuation of the contact sensor.

Embodiment 106. The apparatus according to embodiment 105, where the contact sensor is a pressure sensor or an optical sensor.

Embodiment 107. The apparatus according to embodiment 99, where the instructions further comprise the step of providing an indication that tissue is damaged at one of the first and second locations if the difference is greater than a predetermined threshold.

Embodiment 108. The apparatus according to embodiment 99, where the instructions further comprise the steps of: determining the greater of the first and second perfusion values, and providing an indication that tissue is damaged at the location associated with the greater perfusion value if the difference exceeds a predetermined threshold.

Embodiment 109. A method for identifying damaged tissue, the method comprising: obtaining a first perfusion value from a first location on a patient's skin; obtaining a second perfusion value from a second location that is bisymmetric relative to the first location; determining a difference between the first perfusion value and the second perfusion value.

Embodiment 110. The method according to embodiment 109, further comprising providing an indication that tissue is damaged at one of the first and second locations if the difference is greater than a predetermined threshold.

Embodiment 111. The method according to embodiment 109, further comprising: determining the greater of the first and second perfusion values, and providing an indication that tissue is damaged at the location associated with the greater perfusion value if the difference exceeds a predetermined threshold.

Embodiment 112. A method of detecting tissue damage before it is visible on a patient's skin, comprising: measuring a plurality of perfusion values at a single location at incremental times, calculating a slope between the latest perfusion value and the immediately prior perfusion value, comparing this slope to a threshold value, and determining that there is tissue damage if the slope exceeds the threshold value.

Embodiment 113. A method of detecting tissue damage before it is visible on a patient's skin, comprising: measuring a plurality perfusion values at a plurality of locations at incremental times, calculating a delta value for the plurality of perfusion values for each time, calculating a slope between the latest delta value and the immediately prior delta value, comparing this slope to a threshold value, and determining that there is tissue damage if the slope exceeds the threshold value.

Embodiment 114. A method of detecting tissue damage before it is visible on a patient's skin, comprising: measuring a plurality of perfusion values at a single location at each of a plurality of incremental times, calculating a perfusion delta value for each incremental time, fitting a curve to a predetermined number of the most-recent perfusion delta values, calculating a curvature of the fitted curve, comparing this curvature to a threshold value, and determining that there is tissue damage if the curvature exceeds the threshold value.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

We claim:

1. An apparatus for assessing blood perfusion, said apparatus comprising:
   an emitter configured to emit light at a first wavelength and a second wavelength when activated,
   a first receiver and a second receiver, wherein said first receiver is configured to be placed at a first location on a patient's skin and said second receiver is configured to be placed at the same time against a second location on said patient's skin, wherein said second location is bisymmetric relative to said first location,
   a circuit electronically coupled to said first receiver and said second receiver and configured to measure a first reflected light property of said first receiver and to measure a second reflected light property of said second receiver and provide information regarding said first and second reflected light properties, a processor electronically coupled to said circuit and configured to receive said information, and a non-transitory computer-readable medium electronically coupled to said processor and comprising instructions stored thereon that, when executed on said processor, perform the steps of:

converting said first reflected light property into a first perfusion value and said second reflected light property into a second perfusion value, and determining a difference between said first perfusion value and said second perfusion value.

2. The apparatus according to claim 1, wherein said instructions further comprise a step of providing a signal if said difference is greater than a predetermined threshold.

3. The apparatus according to claim 1, further comprising a switching element configured to detect when said first and second receivers are in proper contact with said patient's skin wherein:

said circuit is electronically coupled to said switching element and configured to measure said first and second reflected light properties when said first and second receivers are in proper contact with said patient's skin.

4. The apparatus according to claim 2, further comprising:

a substrate configured to be placed in a known position on said patient's skin, and said first and second receivers are disposed on said substrate such that said first and second receivers are positioned at bisymmetric locations on said patient's skin when said substrate is placed in said known position on said patient's skin.

5. An apparatus for assessing blood perfusion, said apparatus comprising:

an apparatus body;

an emitter configured to emit light at a first wavelength and a second wavelength when activated;

a first receiver and a second receiver, wherein said two receivers are disposed on said apparatus body to allow simultaneous positioning of said first receiver on a first location on a patient's skin and said second receiver on a second location bisymmetric relative to said first location;

a circuit electronically coupled to each of said two receivers and configured to measure reflected light detected by each of said two receivers;

a processor electronically coupled to said circuit and is configured to receive a first reflected light measurement from a first location and a second reflected light measurement from a second location, and to convert said first reflected light measurement to a first perfusion value and said second reflected light measurement to a second perfusion value; and a non-transitory computer-readable medium electronically coupled to said processor and contains instructions that, when executed on said processor, perform the step of determining a difference between said first perfusion value and said second perfusion value.

6. The apparatus according to claim 5, wherein each of said two receivers are disposed on two ends of said apparatus body while being aligned on a common plane.

7. The apparatus according to claim 5, wherein said apparatus body is rigid and maintains said two receivers at a fixed separation distance and fixed orientation to each other.

8. The apparatus according to claim 5, wherein said apparatus body is flexible and allow said two receivers to be oriented at an angle to each other.

9. The apparatus according to claim 8, wherein said apparatus body comprises a hinge.

10. The apparatus according to claim 5, wherein said first reflected light measurement and said second reflected light measurement are measured simultaneously.

11. The apparatus according to claim 10, wherein said apparatus further comprises a contact sensor positioned proximate to one of said two receivers, and wherein said simultaneous measurements are triggered by the actuation of said contact sensor.

12. The apparatus according to claim 11, wherein said contact sensor is a pressure sensor or an optical sensor.

13. The apparatus according to claim 5, wherein said instructions further comprise the step of providing an indication that tissue is damaged at one of said first and second locations if the difference is greater than a predetermined threshold.

14. The apparatus according to claim 5, wherein said instructions further comprise the steps of:

determining the greater of said first and second perfusion values, and providing an indication that tissue is damaged at the location associated with the greater perfusion value if the difference exceeds a predetermined threshold.

15. An apparatus for assessing perfusion of blood in tissue below a patient's skin, comprising:

an emitter configured to emit light at a first wavelength and a second wavelength when activated, wherein the emitter comprises a first source that emits light at the first wavelength and a second source that emits light at the second wavelength, a first receiver configured to measure a first intensity of received light at the first wavelength and a second intensity of received light at the second wavelength and provide a first signal comprising information about the first and second intensities of the received light, wherein the first receiver comprises a first detector that senses light at the first wavelength and a second detector that senses light at the second wavelength, a substrate coupled to the emitter and the first receiver and configured such that the emitter and first receiver can be placed in simultaneous contact with the patient's skin, and a processor coupled to each of the first detector and the second detector of the first receiver and configured to:

receive the first signal, wherein the first signal comprises individual signals from the first and second detector, determine a first summation value of the first and second intensities of the received light, and determine a level of perfusion of the tissue from the first summation value.

16. An apparatus for assessing perfusion of blood in tissue below a patient's skin, comprising:

an emitter configured to emit light at a first wavelength and a second wavelength when activated, a first receiver configured to measure a first intensity of received light at the first wavelength and a second intensity of received light at the second wavelength and provide a first signal comprising information about the first and second intensities of the received light, a substrate coupled to the emitter and the first receiver and configured such that the emitter and first receiver can be placed in simultaneous contact with the patient's skin, and a processor coupled to the first receiver and configured to:
receive the first signal,
determine a first summation value of the first and second intensities of the received light, and
determine a level of perfusion of the tissue from the first summation value,
wherein:
the processor is coupled to the emitter,
the emitter is configured to emit light upon receipt of a strobe pulse,
the processor is configured to provide the strobe pulse to the emitter and to the first receiver,
the first receiver is further configured to measure a first time period between receipt of the strobe pulse and receipt of light from the emitter, and
the first signal comprises information about the first time period.

17. An apparatus for assessing blood perfusion, said apparatus comprising:
a substrate configured to be placed against a surface of a patient's skin,
a plurality of emitters that are disposed on said substrate at a respective plurality of positions,
where each of said plurality of emitters is configured to emit light at a first wavelength and a second wavelength when activated,
a plurality of receivers that are disposed on said substrate at a respective plurality of positions, a circuit electronically coupled to said plurality of receivers and configured to measure reflected light of a portion of said plurality of receivers and provide a plurality of information regarding said reflected light,
a processor electronically coupled to said circuit and configured to receive said plurality of information regarding said reflected light from said circuit and convert said plurality of said information regarding said reflected light into a respective plurality of perfusion values, and
a non-transitory computer-readable medium electronically coupled to said processor and comprising instructions stored thereon that, when executed on said processor, perform the steps of:
identifying from said plurality of perfusion values a first receiver and a second receiver that are located at first and second positions that are bisymmetric with respect to said patient's skin, and
comparing a first perfusion value that is associated with said first receiver with a second perfusion value that is associated with said second receiver.

18. The apparatus according to claim 17, wherein said instructions further comprise the steps of:
determining a difference between said first and second perfusion values, and
providing an indication that tissue is damaged at one of said first and second locations if said difference is greater than a predetermined threshold.

19. The apparatus according to claim 17, wherein said instructions further comprise the steps of:
determining a difference between said first and second perfusion values,
determining which of said first and second perfusion values is larger than the other, and
providing an indication that tissue is damaged at the location associated with the larger perfusion value if said difference is greater than a predetermined threshold.

* * * * *